US012751780B2

United States Patent
(12) United States Patent
Garcia Kilroy et al.

(10) Patent No.: US 12,751,780 B2
(45) Date of Patent: Oct. 6, 2026

(54) TOOL DRIVER WITH REACTION TORQUE SENSOR FOR USE IN ROBOTIC SURGERY

(71) Applicant: Verb Surgical Inc., Santa Clara, CA (US)

(72) Inventors: Pablo E. Garcia Kilroy, Menlo Park, CA (US); Jose Luis Cordoba, Malaga (ES); Berk Gonenc, Cupertino, CA (US); Xin Liu, Milpitas, CA (US)

(73) Assignee: Auris Health, Inc., Santa Clara, CA (US)

( * ) Notice: Subject to any disclaimer, the term of this patent is extended or adjusted under 35 U.S.C. 154(b) by 54 days.

(21) Appl. No.: 18/907,081

(22) Filed: Oct. 4, 2024

(65) Prior Publication Data

US 2025/0090249 A1 Mar. 20, 2025

Related U.S. Application Data

(63) Continuation of application No. 17/561,369, filed on Dec. 23, 2021, now Pat. No. 12,114,940, which is a (Continued)

(51) Int. Cl.

*A61B 34/30* (2016.01)
*A61B 17/00* (2006.01)

(Continued)

(52) U.S. Cl.

CPC ........ *A61B 34/30* (2016.02); *A61B 17/00234* (2013.01); *A61B 17/3423* (2013.01);

(Continued)

(58) Field of Classification Search

CPC ......... A61B 34/30; A61B 34/32; A61B 34/71; A61B 90/03; A61B 90/06;

(Continued)

(56) References Cited

U.S. PATENT DOCUMENTS 5,780,751 A * 7/1998 Nomerange ............ E05F 15/41 73/862.321
5,807,378 A 9/1998 Jensen et al.

(Continued)

OTHER PUBLICATIONS

Corrected Notice of Allowability received for U.S. Appl. No. 15/803,665, mailed on Dec. 22, 2021, 2 pages.

(Continued)

*Primary Examiner* — Mohamad O El Sayah
(74) *Attorney, Agent, or Firm* — Aikin & Gallant, LLP

(57) ABSTRACT

A tool driver for use in robotic surgery includes a base configured to couple to a distal end of a robotic arm, and a tool carriage slidingly engaged with the base and configured to receive a surgical tool. In one variation, the tool carriage may include a plurality of linear axis drives configured to actuate one or more articulated movements of the surgical tool. In another variation, the tool carriage may include a plurality of rotary axis drives configured to actuate one or more articulated movements of the surgical tool. Various sensors, such as a capacitive load cell for measuring axial load, a position sensor for measuring linear position of the guide based on the rotational positions of gears in a gear transmission, and/or a capacitive torque sensor based on differential capacitance, may be included in the tool driver.

20 Claims, 62 Drawing Sheets

Related U.S. Application Data continuation of application No. 15/803,665, filed on Nov. 3, 2017, now Pat. No. 11,259,881.

(60) Provisional application No. 62/417,205, filed on Nov. 3, 2016.

(51) Int. Cl.

| | |
|---|---|
| ***A61B 17/29*** | (2006.01) |
| ***A61B 17/32*** | (2006.01) |
| ***A61B 17/34*** | (2006.01) |
| ***A61B 34/00*** | (2016.01) |
| ***A61B 34/32*** | (2016.01) |
| ***A61B 90/00*** | (2016.01) |
| ***B25J 13/08*** | (2006.01) |
| ***B25J 15/00*** | (2006.01) |
| ***G01L 1/14*** | (2006.01) |
| ***G01L 3/14*** | (2006.01) |
| ***G01L 5/22*** | (2006.01) |
| ***H02K 7/116*** | (2006.01) |
| ***H02K 11/215*** | (2016.01) |
| ***H02K 11/24*** | (2016.01) |
| ***H02K 29/08*** | (2006.01) |
| ***H02P 6/08*** | (2016.01) |
| ***H02P 6/16*** | (2016.01) |

(52) U.S. Cl.

CPC .............. *A61B 34/32* (2016.02); *A61B 34/71* (2016.02); *A61B 90/03* (2016.02); *A61B 90/06* (2016.02); *B25J 13/085* (2013.01); *B25J 15/0019* (2013.01); *G01L 1/142* (2013.01); *G01L 3/1428* (2013.01); *G01L 3/1442* (2013.01); *G01L 5/226* (2013.01); *H02K 7/1163* (2013.01); *H02K 11/215* (2016.01); *H02K 11/24* (2016.01); *H02K 29/08* (2013.01); *A61B 2017/00119* (2013.01); *A61B 2017/00398* (2013.01); *A61B 2017/00477* (2013.01); *A61B 2017/00853* (2013.01); *A61B 2017/00991* (2013.01); *A61B 17/29* (2013.01); *A61B 17/320016* (2013.01); *A61B 2034/302* (2016.02); *A61B 2090/031* (2016.02); *A61B 2090/066* (2016.02); *A61B 2090/0807* (2016.02); *A61B 2090/0809* (2016.02); *A61B 2090/0811* (2016.02); *H02P 6/08* (2013.01); *H02P 6/16* (2013.01)

(58) Field of Classification Search

CPC .......... A61B 17/00234; A61B 17/3423; A61B 2034/302; A61B 2090/031; A61B 2090/066; A61B 2090/0807; A61B 2090/0809; A61B 2090/0811; A61B 17/29; A61B 17/320016; A61B 2017/00119; A61B 2017/00398; A61B 2017/00477; A61B 2017/00853; A61B 2017/00991; H02K 11/215; H02K 11/24; H02K 7/1163; H02K 29/08; B25J 13/085; B25J 15/0019; G01L 1/142; G01L 3/1428; G01L 3/1442; G01L 5/226; H02P 6/08; H02P 6/16

See application file for complete search history.

(56) References Cited

U.S. PATENT DOCUMENTS

| | | | | |
|---|---|---|---|---|
| 6,955,097 | B1 | 10/2005 | Madni et al. | |
| 7,918,230 | B2 | 4/2011 | Whitman et al. | |
| 7,942,874 | B2 | 5/2011 | Eder et al. | |
| 8,941,392 | B1 | 1/2015 | Reese | |
| 9,895,813 | B2 | 2/2018 | Blumenkranz et al. | |
| 10,239,213 | B1 | 3/2019 | Reich | |
| 10,434,643 | B1 * | 10/2019 | Berkowitz | B25J 13/085 |
| 10,903,725 | B2 | 1/2021 | Covington et al. | |
| 11,259,881 | B2 | 3/2022 | Garcia Kilroy et al. | |
| 2007/0024387 | A1 | 2/2007 | Sandacci et al. | |
| 2008/0009838 | A1 | 1/2008 | Schena et al. | |
| 2010/0016114 | A1 | 1/2010 | Chang | |
| 2010/0094312 | A1 | 4/2010 | Ruiz et al. | |
| 2011/0290855 | A1 | 12/2011 | Moore et al. | |
| 2012/0198945 | A1 | 8/2012 | Yoneyama | |
| 2012/0205421 | A1 | 8/2012 | Shelton, IV | |
| 2013/0324993 | A1 | 12/2013 | Mccarthy et al. | |
| 2014/0060223 | A1 * | 3/2014 | Tanaka | B25J 9/02 901/23 |
| 2014/0228862 | A1 * | 8/2014 | Inoue | A61B 34/37 606/130 |
| 2014/0343567 | A1 * | 11/2014 | Morash | A61B 17/16 606/130 |
| 2015/0105799 | A1 * | 4/2015 | Lohmeier | A61B 34/71 606/130 |
| 2015/0188452 | A1 | 7/2015 | Herzer et al. | |
| 2015/0209035 | A1 | 7/2015 | Zemlok | |
| 2015/0316431 | A1 | 11/2015 | Collins et al. | |
| 2016/0256225 | A1 * | 9/2016 | Crawford | A61B 90/98 |
| 2016/0288338 | A1 | 10/2016 | Murphy et al. | |
| 2016/0314710 | A1 * | 10/2016 | Jarc | G09B 23/28 |
| 2017/0007254 | A1 | 1/2017 | Jaworek et al. | |
| 2017/0016756 | A1 | 1/2017 | Dewald | |
| 2017/0273749 | A1 | 9/2017 | Grover et al. | |
| 2018/0116737 | A1 | 5/2018 | Bajo et al. | |
| 2018/0116738 | A1 | 5/2018 | Bajo et al. | |
| 2018/0116741 | A1 | 5/2018 | Garcia et al. | |
| 2018/0132959 | A1 | 5/2018 | Marshall et al. | |
| 2018/0133894 | A1 | 5/2018 | Choi et al. | |
| 2018/0348074 | A1 | 12/2018 | Okada et al. | |
| 2018/0370045 | A1 * | 12/2018 | Kan | A61B 34/71 |
| 2019/0142537 | A1 | 5/2019 | Covington | |

OTHER PUBLICATIONS

Non-Final Office Action of the U.S. Patent Office dated Nov. 1, 2019 for related U.S. Appl. No. 15/803,659.

Non-Final Office Action received for U.S. Appl. No. 15/803,665, mailed on Dec. 4, 2020, 16 pages.

Non-Final Office Action received for U.S. Appl. No. 15/803,665, mailed on May 27, 2020, 12 pages.

Non-Final Office Action received for U.S. Appl. No. 17/561,369, mailed on Mar. 11, 2024,32 pages.

Notice of Allowance of the U.S. Patent Office dated Feb. 26, 2020 for related U.S. Appl. No. 15/803,659.

Notice of Allowance of the US Patent Office dated Mar. 25, 2020 for related U.S. Appl. No. 15/803,668.

Notice of Allowance received for U.S. Appl. No. 15/803,665 , mailed on Jun. 28, 2021, 5 pages.

Notice of Allowance received for U.S. Appl. No. 15/803,665 , mailed on Sep. 15, 2021, 5 pages.

Notice of Allowance received for U.S. Appl. No. 17/561,369, mailed on Jul. 31, 2024, 8 pages.

Office action dated Nov. 14, 2019 for related U.S. Appl. No. 15/803,668.

U.S. Appl. No. 62/436,957, filed Dec. 20, 2016.

U.S. Appl. No. 62/436,965, filed Dec. 20, 2016.

U.S. Appl. No. 62/436,974, filed Dec. 20, 2016.

U.S. Appl. No. 62/436,981, filed Dec. 20, 2016.

U.S. Appl, No. 62/526,871, filed Jun. 29, 2017.

U.S. Appl. No. 62/548,292, filed Aug. 21, 2017.

* cited by examiner

FIG. 32A
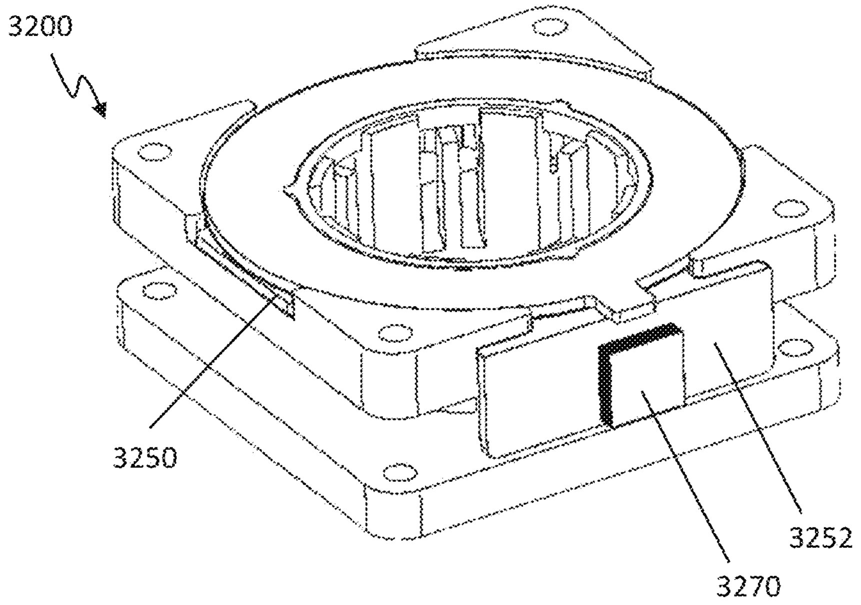
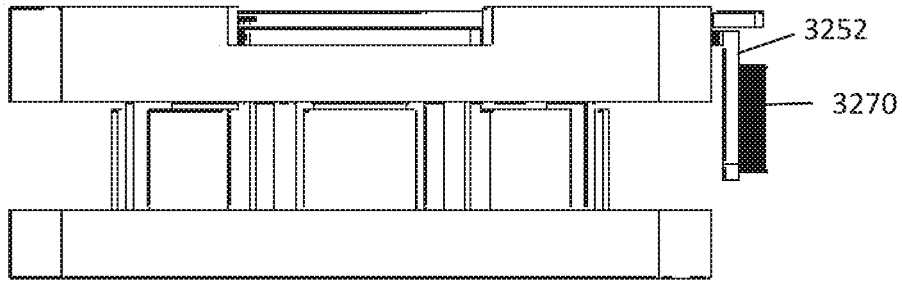
FIG. 32B

TOOL DRIVER WITH REACTION TORQUE SENSOR FOR USE IN ROBOTIC SURGERY

CROSS-REFERENCE TO RELATED APPLICATIONS

This application is a continuation of U.S. patent application Ser. No. 17/561,369 filed Dec. 23, 2021, now U.S. Pat. No. 12,114,940, issued on Oct. 15, 2024, which is a continuation of U.S. patent application Ser. No. 15/803,665 filed Nov. 3, 2017, now U.S. Pat. No. 11,259,881, issued Mar. 1, 2022, which claims priority to U.S. Patent Application Ser. No. 62/417,205, filed on Nov. 3, 2016, which is incorporated by this reference herein in its entirety.

TECHNICAL FIELD

This disclosure relates generally to robotic or robotic-assisted systems and, more particularly, to tool drivers for robotic or robotic-assisted surgical systems.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. However, standard MIS systems have a number of drawbacks. For example, non-robotic MIS systems place higher demands on the surgeon, in part because they require surgeons to indirectly manipulate tissue via tools in a manner that may not be natural. Conventional robotic systems, which may include one or more tool drivers positioned with a robotic arm and remotely operated to manipulate tools based on commands from an operator, may provide many benefits of MIS while reducing demands on the surgeon. However, such tool drivers tend to be large and difficult to maneuver effectively with robotic arms. Thus, it is desirable to have tool drivers for robotic-assisted surgical systems that are more compact and efficient.

SUMMARY

Generally, in some variations, a tool driver for use in robotic surgery includes a base configured to couple to a distal end of a robotic arm, where the base includes a longitudinal track, and a tool carriage slidingly engaged with the longitudinal track and configured to receive a surgical tool, where the tool carriage includes at least one linear axis drive assembly. The linear axis drive assembly may include, for example, a motor including a motor shaft, a gear transmission coupled to the motor, a threaded shaft having a proximal shaft end coupled to the gear transmission and a distal shaft end providing a linear axis drive output, and an axially-movable guide mounted on the threaded shaft. The threaded shaft may, in some variations, be a ball screw and the guide may be or include a ball screw nut engaged with the ball screw. The linear axis drive output may be configured to actuate one or more articulated movements of the surgical tool. In some variations, the tool carriage may further include at least one rotary axis drive assembly configured to rotate the surgical tool around a tool axis. For example, the tool carriage may include two rotary axis drive assemblies configured to antagonistically rotate the surgical tool around the tool axis.

In some variations, the tool driver may include a capacitive load cell having characteristics making it suitable for use in a compact area. For example, the load cell may be disposed on the threaded shaft between the guide and the distal shaft end and configured to measure axial load on the threaded shaft. The capacitive load cell may include a first conductive plate fixed relative to the guide and a second conductive plate fixed relative to the threaded shaft. The capacitive load cell may, for example, include a housing having a first housing region and a second housing region axially movable relative to the first housing region. For example, the second housing region may be radially connected to the first housing region (e.g., the radial connection may allow for relative axial movement between the first and second housing regions). The first housing region may be coupled to the guide and the second housing region may be coupled to the threaded shaft. In some variations, the first conductive plate may be coupled to the first housing region and the second conductive plate may be coupled to the second housing region.

Additionally or alternatively, in some variations, the tool driver may include a position sensor integrated with or adjacent to the gear transmission, such that the position sensor is compact and utilizes information from parts existing in the gear transmission in order to measure axial position of the guide. For example, the gear transmission may include a first gear having a first number of teeth and a second gear having a second number of teeth different from the first number of teeth, and the tool driver may further include a position sensor for measuring axial position of the guide based on relative rotational positions of the first and second gears. For example, the position sensor may include a first rotary encoder measuring rotational position of the first gear, and a second rotary encoder measuring rotational position of the second gear. In some variations, the first gear may be coupled to the motor shaft and the second gear may be coupled to the proximal shaft of the threaded shaft. The second gear may have more teeth than the first gear, but alternatively the first gear may have more teeth than the second gear. In other variations, the first and second gears whose relative rotational positions are measured may be in any suitable portion of the gear transmission.

Generally, different variations of a tool driver may include at least one linear axis drive assembly including a capacitive load cell similar to that described above. The linear axis drive assembly may be configured to actuate one or more articulated movements of a surgical tool. For example, generally, a tool driver for use in robotic surgery may include at least one linear axis drive assembly including a threaded shaft and a guide mounted on the threaded shaft, and a capacitive load cell disposed on the threaded shaft and configured to measure axial load on the threaded shaft.

The capacitive load cell may include characteristics making it suitable for use in a compact area. For example, the load cell may be disposed between the guide and a distal end of the threaded shaft. In some variations, the capacitive load cell may include a first conductive plate referenced to the guide and a second conductive plate referenced to the threaded shaft. The capacitive load cell may include a housing having a first housing region and a second housing region axially movable relative to the first housing region.

The first housing region may be coupled to the guide and the second housing region may be coupled to the threaded shaft. The second housing region may, for example, be radially connected to the first housing region. The first conductive plate may be coupled to the first housing region and the second conductive plate may be coupled to the second housing region. In some variations, the load cell may be disposed between the guide and a distal end of the threaded shaft.

Furthermore, different variations of a tool driver may include at least one linear axis drive assembly including a position sensor similar to that described above. The linear axis drive assembly may be configure to actuate one or more articulated movements of a surgical tool. For example, generally, a tool driver for use in robotic surgery may include at least one linear axis drive assembly including a motor including a motor shaft, a gear transmission coupled to the motor shaft, and an axially movable guide driven by the motor via the gear transmission. The gear transmission may include a first gear having a first number of teeth and a second gear having a second number of teeth different from the first number of teeth. In these variations, the tool driver may further include a position sensor for measuring linear position of the guide based on the rotational positions of the first and second gear.

The position sensor may be integrated with or adjacent to the gear transmission, such that the position sensor is compact and utilizes information from parts existing in the gear transmission in order to measure axial position of the guide. For example, the position sensor may include a first rotary encoder measuring rotational position of the first gear, and a second rotary encoder measuring rotational position of the second gear. The position sensor may measure linear position of the shaft based on the relative rotational positions of the first and second gears (e.g., the rotational position of the first gear relative to the rotational position of the second gear). In some variations, the first gear may be coupled to the motor shaft and the second gear may be coupled to the proximal shaft of the threaded shaft. The second gear may have more teeth than the first gear, but alternatively the first gear may have more teeth than the second gear. In other variations, the first and second gears whose relative rotational positions are measured may be in any suitable portion of the gear transmission.

Generally, a tool driver for use in robotic surgery may include at least one rotary axis drive for actuating one or more articulated movements of a surgical tool, where the rotary axis drive includes a motor and a torque sensor included to the motor (e.g., for measuring reaction torque during actuation by the rotary axis drive).

In some variations, the torque sensor may include a torsional spring structure having a proximal spring portion and a distal spring portion, a first patterned conductive surface referenced to the proximal spring portion, and a second patterned conductive surface facing the first patterned conductive surface and referenced to the distal spring portion. The first and second patterned conductive surfaces may, for example, be disposed on first and second plates, respectively. The torque sensor may be configured to provide a torque measurement based at least in part on a differential capacitance between the first and second patterned conductive surfaces. In some variations, the proximal spring portion and the distal spring portion may be connected via a plurality of members (e.g., one or more members that flex torsionally). One or more stoppers (e.g., mechanical stoppers) may limit the relative rotational movement of the proximal spring portion and the distal spring portion.

In these variations of a torque sensor with a torsional spring structure, the proximal spring portion may, for example, be coupled to the rotary axis drive to mount the torque sensor to the rotary axis drive. In some variations, the first and second conductive surfaces may be directly or indirectly coupled to the torsional spring structure such that the first patterned conductive surface (referenced to the proximal spring portion) is proximal to the second patterned conductive surface (referenced to the distal spring portion). Alternatively, in other variations, the first and second conductive surfaces may be directly or indirectly coupled to the torsional spring structure such that the first patterned conductive surface (referenced to the proximal spring portion) is distal to the second patterned conductive surface (referenced to the distal spring portion).

In some variations, the torque sensor may include a first patterned conductive surface and a second patterned conductive surface, where the first and second patterned conductive surfaces are rotatable relative to each other. The torque sensor may be configured to provide a torque measurement based at least in part on differential capacitance between the first and second patterned conductive surfaces. In some variations, the first and second patterned conductive surfaces may be disposed on first and second plates, respectively, and the torque sensor may include a frame including a proximal frame portion coupled to the first plate and a distal frame portion coupled to the second plate. The first plate may be proximal to the second plate. Alternatively, the first plate may be distal to the second plate. The proximal frame portion and the distal frame portion may be connected via at least one member (e.g., one or more members that flex torsionally). One or more stoppers (e.g., mechanical stoppers) may limit the relative rotational movement of the proximal spring portion and the distal spring portion.

In various torque sensor variations, at least one of the first and second patterned conductive surfaces may include a first plurality of conductive strips and a second plurality of conductive strips. For example, the surface with the first and second groups of conductive strips may be considered an "active" conductive surface. The first plurality of conductive strips may be interconnected (e.g., via at least one conductive trace) to form a first signal channel, and the second plurality of conductive strips may be interconnected (e.g., via at least one conductive trace) to form a second signal channel. In some variations, the first plurality of conductive strips and the second plurality of conductive strips may be arranged in an alternating pattern.

Additionally, at least one of the first and second patterned conductive surfaces may include a third plurality of conductive strips facing the first and the second pluralities of conductive strips. The third plurality of conductive strips may be interconnected to form a common electrical ground. For example, the surface with the third plurality of conductive strips may be considered a "ground" conductive surface facing the "active" conductive surface.

Generally in some variations, a tool driver for use in robotic surgery may include at least one rotary axis drive including a rotary output shaft configured to actuate one or more articulated movements of a surgical tool, where the rotary axis drive includes a motor including a motor shaft, a gear transmission at least partially disposed within the motor shaft where the gear transmission (e.g., a planetary gear train) include an input coupled to the motor shaft and an output shaft coupled to the rotary output shaft, and a torque sensor disposed between the gear transmission and a distal end of the rotary output shaft. In some variations, the tool driver may include a base configured to couple to a distal end of a robotic arm, and the tool carriage may be slidingly engaged with the base.

In some variations, the rotary axis drive may include a cable carrying signals (e.g., at least from the torque sensor), where the cable wraps circumferentially at least partially around the rotary axis drive, around an axis of rotation of the rotary shaft. By following the path of torsional motion of the rotary axis drive (e.g., as the result of reaction torque during actuation), such circumferential wrapping may reduce undesirable strain or other loads on the cable. For example, the cable may wrap at least about 45 degrees around the rotary axis drive, at least 90 degrees around the rotary axis drive, or at least about 135 degrees around the rotary axis drive.

In some variations, the rotary output shaft may be configured to rotate around and axially translate along an axis. In such variations, a rotary encoder may be configured to measure an axial position of the rotary output shaft along the axis (additionally or alternatively to being configured to measure rotational position of the rotary output shaft).

A tool driver may include a plurality of such rotary axis drives. In some variations, one or more of the rotary drives may be mounted to a tool carriage only a distal portion of the rotary axis drive (e.g., and otherwise may be free-standing, or unsupported by additional framework structures, etc.).

Generally, in some variations, a tool driver for use in robotic surgery may include a base configured to couple to a distal end of a robotic arm, a tool carriage slidingly engaged with the base and configured to receive a surgical tool, where the tool carriage includes a plurality of rotary axis drive modules. The rotary axis drive modules may be configure to actuate one or more articulated movements of the surgical tool, and may be arranged in the tool carriage in a modular, scalable array. In some variations, each rotary axis drive module may be mounted to the tool carriage only at a distal portion of the rotary axis drive module.

The plurality of rotary axis drive modules may be arranged in a regular repeating pattern in the tool carriage. Furthermore, the tool driver may include a plurality of circuit board modules, where each circuit board module is associated with at least one rotary axis drive module. The plurality of circuit board modules may be arranged in a second regular repeating pattern. In some variations, the plurality of circuit board modules may be interconnected via a cable.

BRIEF DESCRIPTION OF THE DRAWINGS

FIGS. 32A and 32B are perspective and side views of another variation of a torque sensor with an angled electronics mount portion.

DETAILED DESCRIPTION

Non-limiting examples of various aspects and variations of the invention are described herein and illustrated in the accompanying drawings.

Overview

Figure 1:
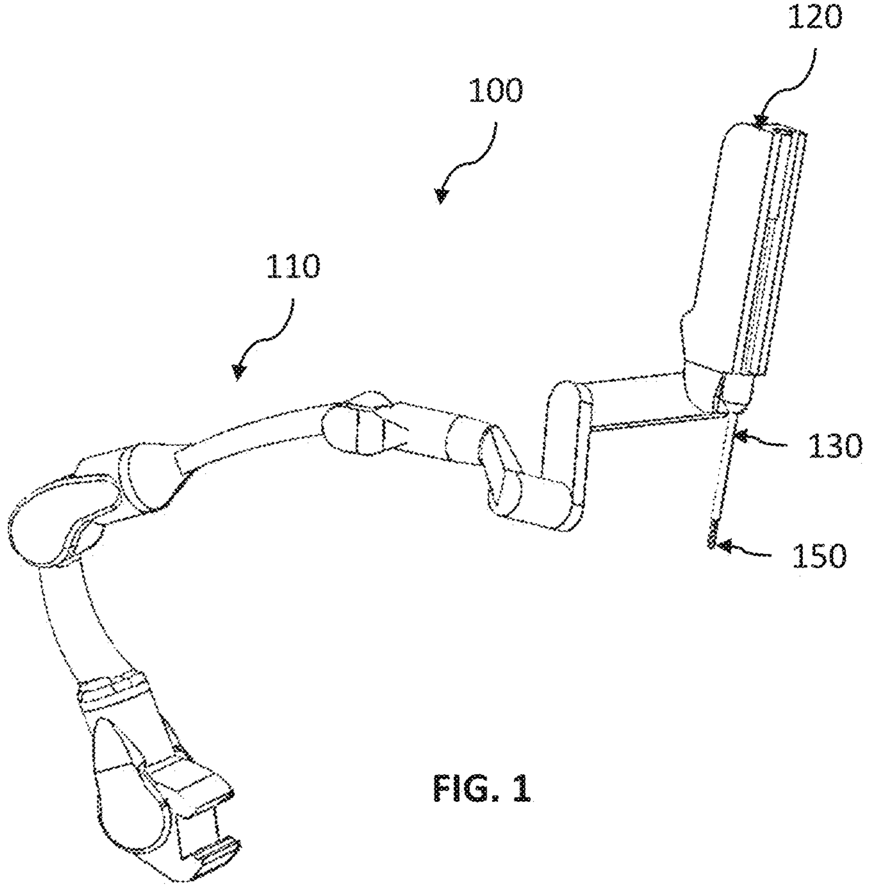
FIG. 1 is a schematic illustration of one exemplary variation of a tool driver on a robotic arm manipulator.

Generally, a robotic or robotic-assisted surgical system (e.g., to enable a minimally-invasive surgical procedure) may include one or more robotic arms for manipulating surgical tools, such as during minimally-invasive surgery. For example, as shown in the exemplary schematic of FIG. 1, a robotic assembly 100 may include a robotic arm 110 and a tool driver 120 generally attached to a distal end of the robotic arm 110. A cannula 130 coupled to the tool driver 120 may telescopically receive a surgical instrument or tool 150. Furthermore, the robotic arm 110 may include a plurality of links that are actuated so as to position and orient the tool driver 120.

For use in a surgical procedure, the robotic arm 110 may be mounted to an operating table on which a patient lies (or on a cart, ceiling, sidewall, etc. near the patient). To create a port for enabling introduction of a surgical tool into the patient, a trocar assembly (typically a cannula 130 and obturator) may be at least partially inserted into the patient through an incision or entry point in the patient (e.g., in the abdominal wall). After the cannula is placed in this manner (and the obturator is removed), the robotic arm 110 may maneuver the tool driver 120 closer to the port, where the cannula 130 may be coupled to the tool driver 120. Additionally, a tool 150 may be coupled to the tool driver 120 such that at least a portion (e.g., tool shaft) passes through the cannula and into the patient. The tool 150 may have an end effector disposed at the distal end of the tool shaft, and the tool driver 120 may further be controlled to position and/or actuate the tool 150, as further described herein, to perform various tasks during a surgical procedure (e.g., cutting, grasping, etc.) in accordance with the particular kind of end effector. Additionally, the tool 150 may be withdrawn from the port and decoupled from the tool driver 120 to exchange with another tool, such as another tool having an end effector with different functionality.

Figure 2B:
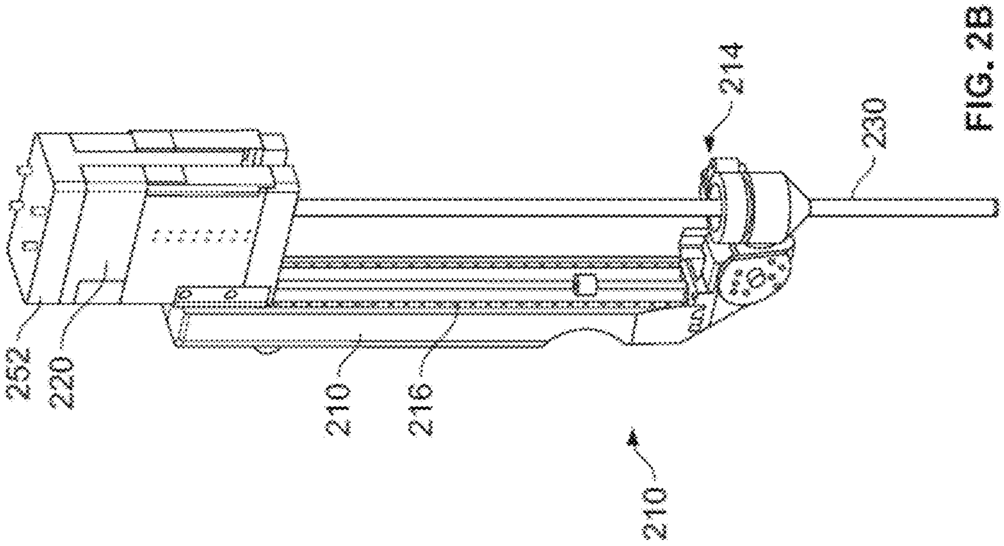
FIGS. 2A and 2B are perspective views of an exemplary variation of a tool driver.
Figure 2A:
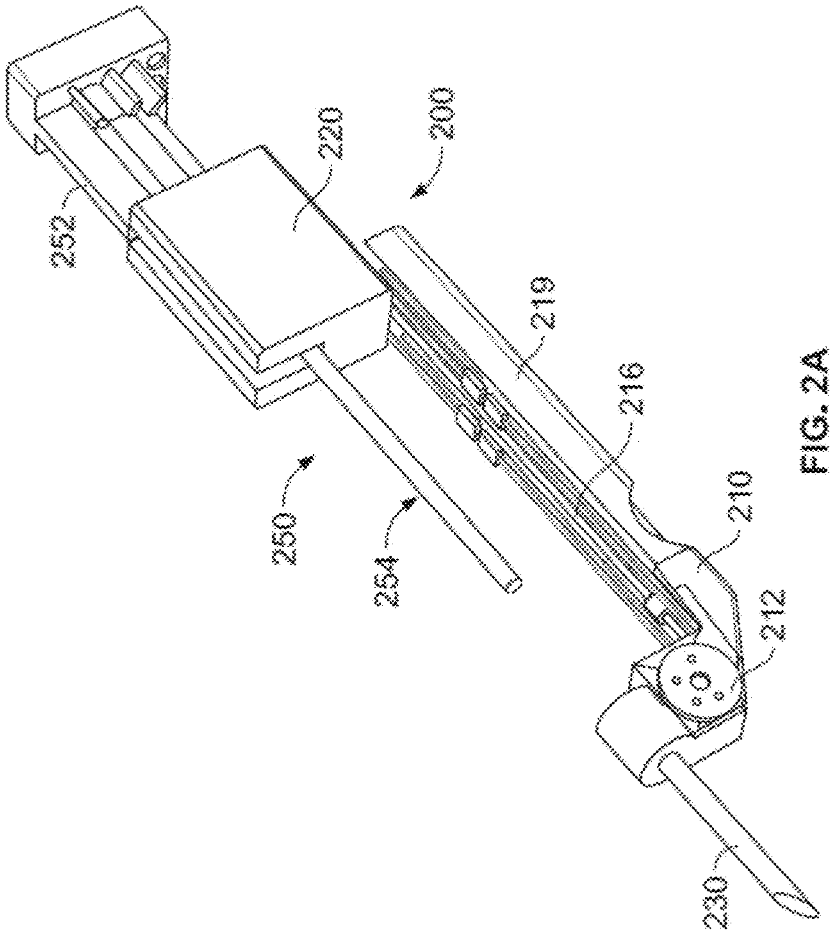
Figure 2C:
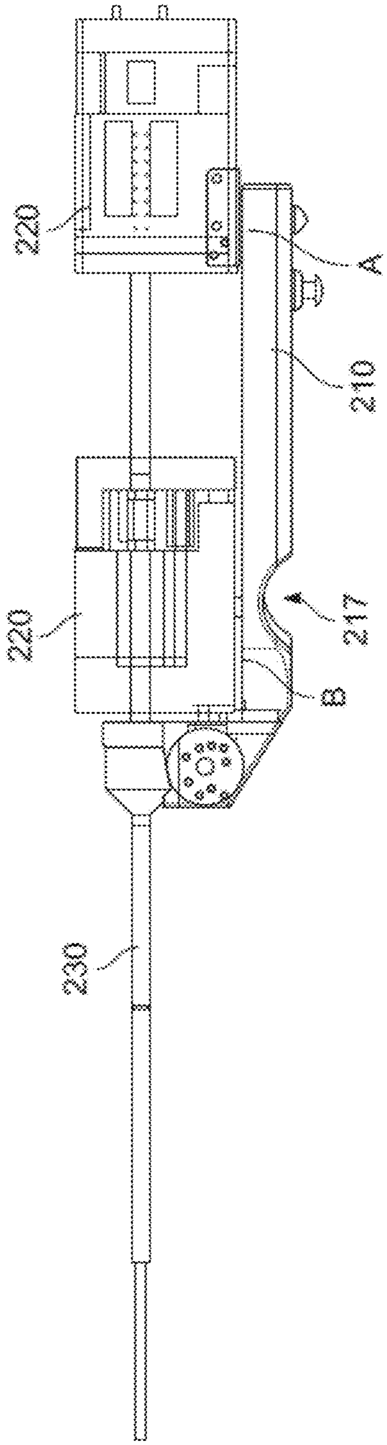
FIG. 2C is a side view of the tool driver of FIGS. 2A and 2B showing the tool carriage in two different positions.

As shown in FIGS. 2A and 2B, in one variation, a tool driver 200 may include an elongated base (or "stage") 210 including a longitudinal track 216 and a tool carriage 220 which is slidingly engaged with the longitudinal track 216. The base 210 may be configured to couple to a distal end of a robotic arm such that articulation of the robotic arm positions and/or orients the tool driver 200 in space. Additionally, the tool carriage may be configured to receive a tool base 252 of a tool 250 having a tool shaft 254 extending from the tool base 252 and further having an end effector (not shown) disposed at a distal end of the tool shaft. Generally, the tool carriage 220 may be configured to position the end effector of the tool relative to the base 210. For example, as shown in FIG. 2C, the tool carriage 220 may be actuated to a first position (position A) on the base 210, which positions the end effector of the tool at a relatively proximal location such that the tool shaft extends the least amount possible beyond the end of the cannula 230. When the tool carriage 220 is located at position A, for example, the tool carriage 220 may be permitted to extend beyond the edge of the base 210 (i.e., cantilevered off the base 210). Additionally, the tool carriage 220 may be actuated to a second position (position B) on the base 210, which positions the end effector of the tool at a relatively distal position where the tool shaft extends the most amount possible beyond the end of the cannula 230. Furthermore, the tool carriage 220 may be actuated along the longitudinal track 216 generally to any point between a proximal position and a distal position (e.g., positions A and B depicted in FIG. 2C).

Figure 34:
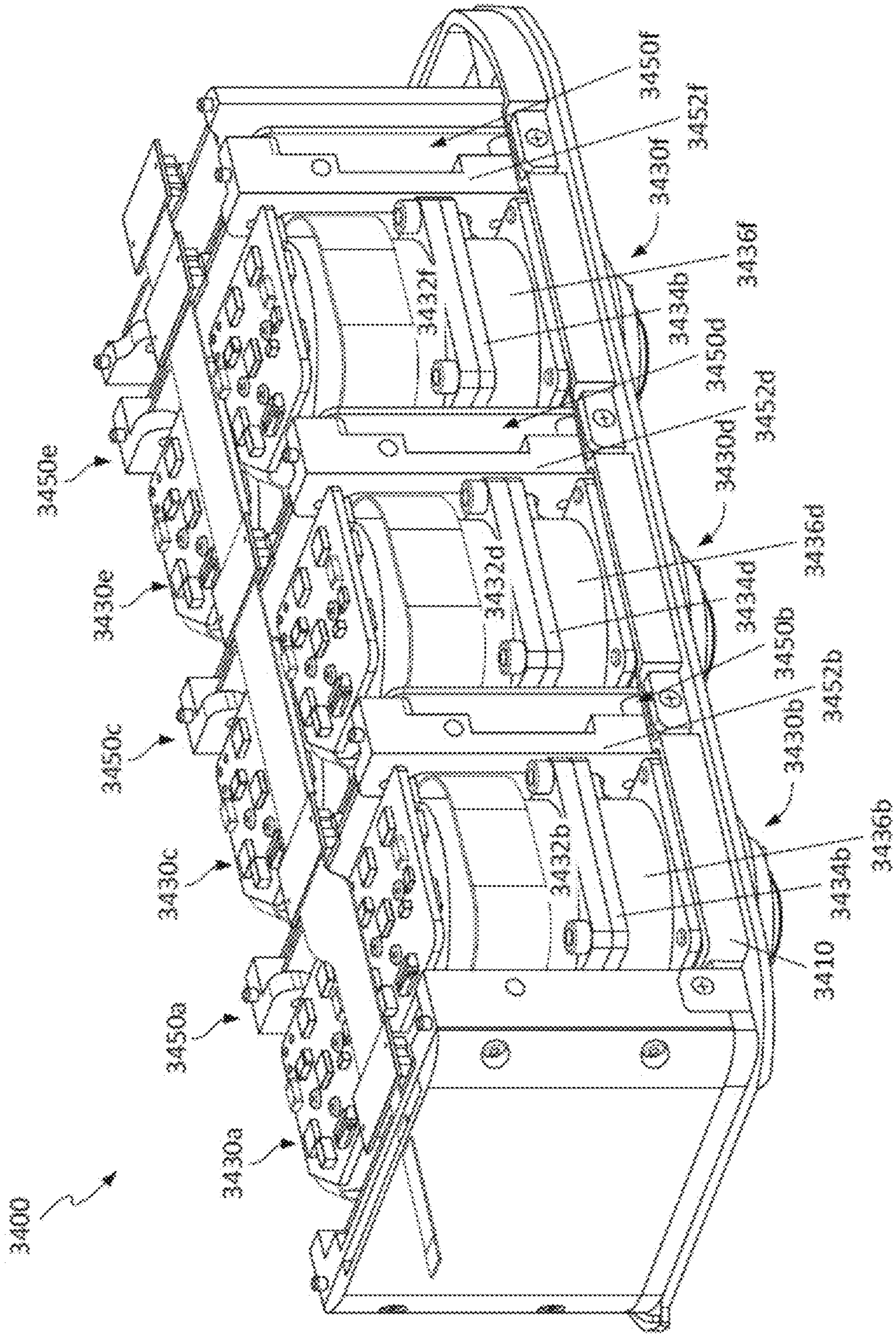
FIG. 34 is a perspective view of another variation of a tool driver with a plurality of rotary axis drives.

Generally, the tool carriage 220 may additionally be configured to orient and/or actuate the end effector of the tool. For example, the tool carriage 220 may enable rotation of the tool shaft around a longitudinal tool axis, thereby rotating the end effector of the tool about the longitudinal tool axis. Additionally, the tool carriage 220 may actuate specific functionalities of the end effector, such as through a cable system manipulated and controlled by actuated drives (e.g., linear axis drive, rotary axis drive, etc. such as those described herein). The tool carriage may include different configurations of actuated drives. For example, in one variation, as shown in FIGS. 2A-2C, the tool carriage 220 may include a plurality of linear axis drives configured via a cable system to actuate a set of one or more articulated movements of the end effector and at least one rotary axis drive configured to rotate the tool shaft around a tool axis. In another variation, FIGS. 9A and 9B and FIG. 34, a tool driver 900 may include an elongated base 910 similar to base 210, but with a tool carriage 920 that may include a plurality of rotary axis drives for actuating via a cable system a set of one or more articulated movements of the end effector. FIG. 34 illustrates another tool driver variation with a plurality of rotary axis drives. Additional details of variations of tool carriages are described further below.

Base

The tool driver may include a base (or "stage") that provides structural support for the tool driver and its various components which are housed within a cover or housing. For example, as shown in FIGS. 3A and 3B, the base 310 (with no housing shown, for clarity) may include at least one longitudinal track 316 for supporting and guiding movement of the tool carriage along a longitudinal axis of the base 310, and one or more interfaces such as an arm adapter 312 for coupling the base 310 to a robotic arm (or other manipulator) and an exemplary cannula adapter 314 for coupling the base 310 to a cannula.

Figure 3A:
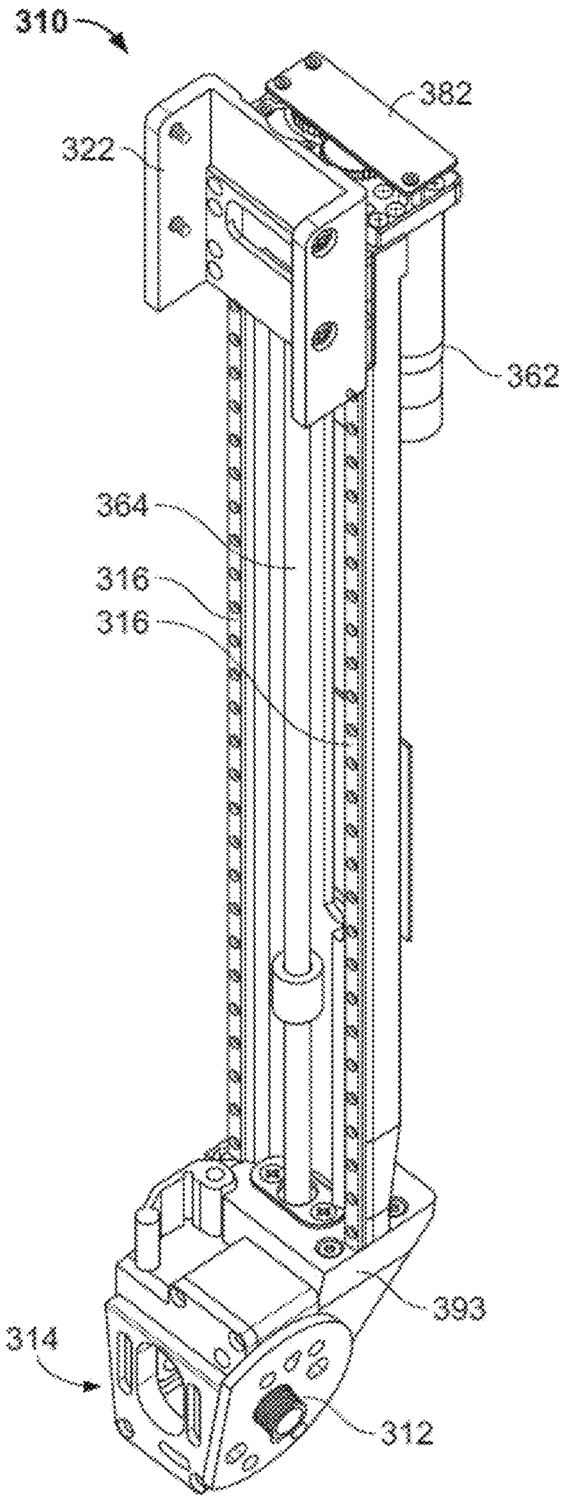
FIGS. 3A and 3B are front perspective and rear perspective views, respectively, of a base in an exemplary variation of a tool driver.
Figure 3B:
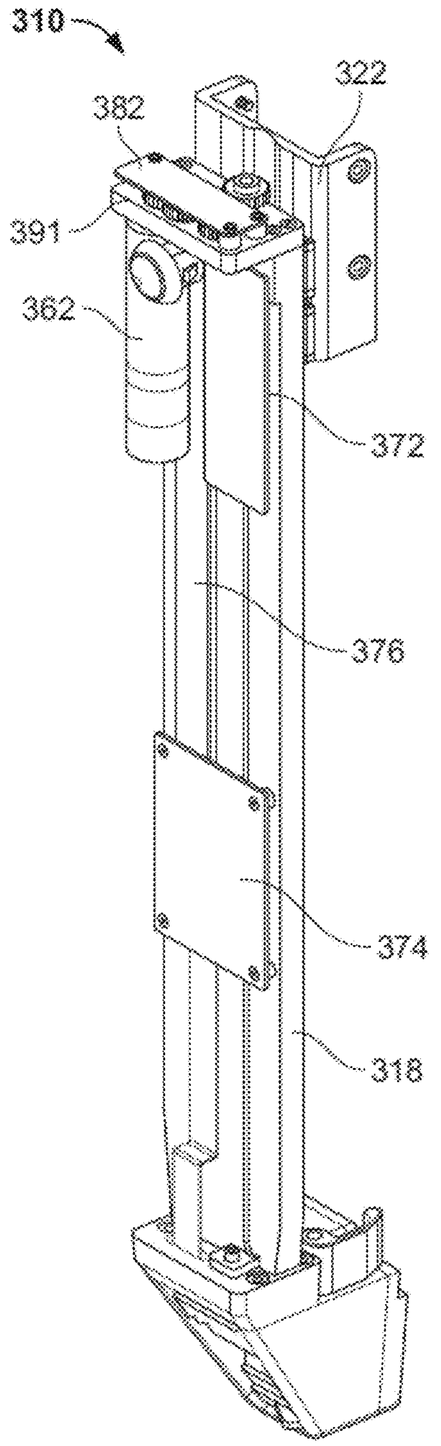

In one variation, the longitudinal track 316 may include a pair of rails mounted on a backbone member 318, as shown in FIG. 3A, which are parallel and extend along at least a portion of the length of the base 310. The rails may be, for example, linear rails with linear bearings or other suitable linear guides. Other examples of longitudinal tracks include a single rail, three or more parallel rails, grooves, etc. The tool carriage (not shown) may be coupled to a bracket 322 or other suitable carriage interface that slidingly engages with the longitudinal track 316.

The tool driver may include a linear actuator configured to actuate the tool carriage along the longitudinal track. The linear actuator may include, for example, a motor module 362, a ball screw 364 and a ball nut (not shown) that is threadingly engaged with the ball screw 364, and a series of one or more gears coupling an output of the motor module 362 to the ball screw 364. As the ball screw 364 is rotated by the motor module 362 and series of gears, the ball nut travels linearly along the base 310. The tool carriage may be coupled to the ball nut directly or via bracket 322 (e.g., mounted with fasteners), such that the tool carriage travels with the ball nut. In other variations, other suitable linear actuators (e.g., other kinds of leadscrews) may be used to actuate the tool carriage along the longitudinal track.

Figure 3C:
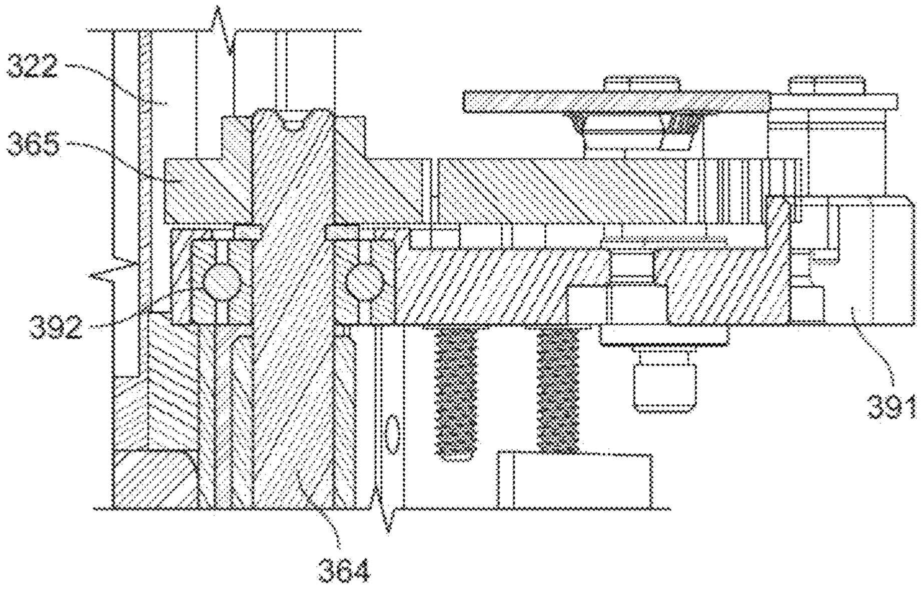
FIGS. 3C and 3D are detailed side and top views of a proximal mounting plate on the base depicted in FIGS. 3A and 3B.
Figure 3D:
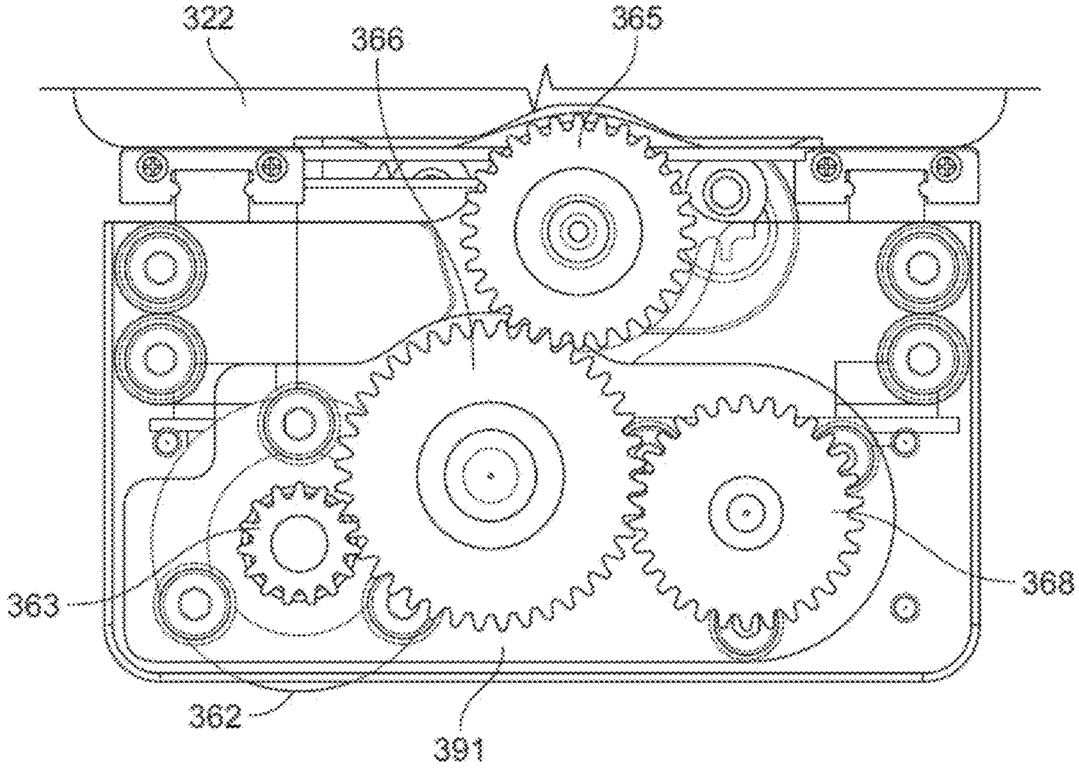
Figure 3E:
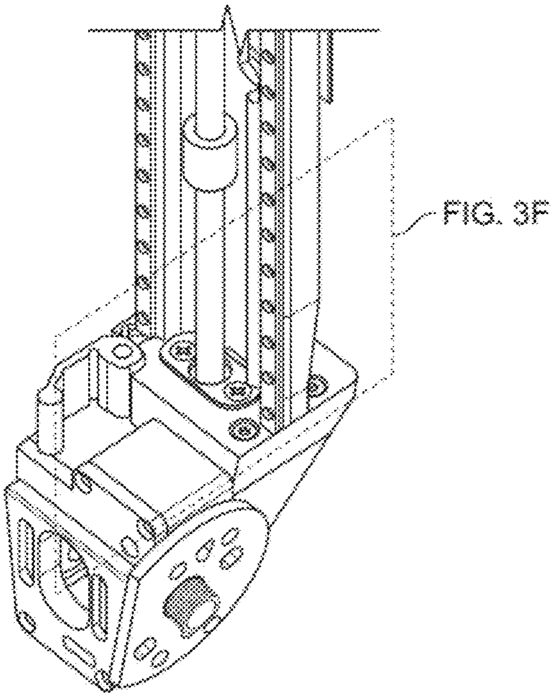
FIG. 3E is a partial perspective view of a distal end of the base depicted in FIGS. 3A and 3B.
Figure 3F:
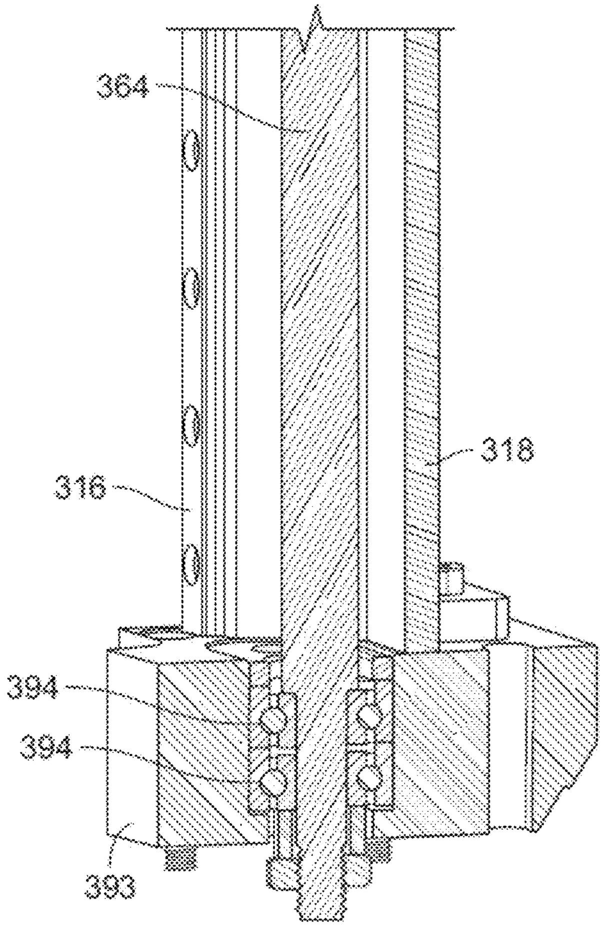
FIG. 3F is a longitudinal cross-sectional view of the region of the base marked 3F in FIG. 3E.

The motor module 362 may include a servomotor or other suitable motor and, in some variations, a gear transmission (e.g., planetary, harmonic drive, etc.) for increasing the available torque output of the motor module. Such a gear transmission may be coupled to an output shaft of the motor module in series, or integrated into the motor module (e.g., in a rotor of the motor) similar to that described below. A proximal end of the ball screw 364 may be mounted on a proximal mounting block 391 (as shown in FIGS. 3B-3D) via at least one proximal radial bearing 392. Similarly, a distal end of the ball screw 363 may be mounted on a distal mounting block 393 via at least one distal radial bearing 394 (as shown in FIG. 3F, which is a longitudinal cross-sectional view of the portion of the tool driver shown in FIG. 3E). In some variations, the longitudinal track 316 may be omitted such that the tool carriage travels based on the linear actuation (e.g., ball screw 364).

As shown in FIGS. 3C and 3D, the series of gears may include a motor drive gear 363 mounted to the output shaft of the motor module 362 (e.g., with one or more set screws), at least one idler gear 366 engaged with the motor drive gear 363, and a ball screw gear 365 engaged with the idler gear 366 and mounted to the ball screw 364 (e.g., with one or more set screws). The relative numbers of teeth on at least the motor drive gear 363 and the ball screw gear 365 may be selected to provide additional torque increase. For example, in one exemplary variation depicted in FIG. 3D, the ball screw gear 365 may have thirty teeth and the motor drive gear 363 may have fifteen teeth, thereby providing a gear ratio or mechanical advantage of about 2:1. In other examples, the series of gears (at least the motor drive gear 363 and the ball screw gear 365) may have a gear ratio between about 1:1 and 5:1, between about 1:1 and 4:1, between about 1:1 and 3:1, or between about 1.5:1 and 2.5:1. The idler gear 366 may have any suitable number of teeth, though the number of teeth may be selected to optimize the design of an absolute multi-turn encoder (further described below) for measuring absolute linear position of the carriage on the stage. Furthermore, a dummy split gear 368 may be engaged with the first idler gear 366 and have a similarly suitable number of teeth to optimize the design of the absolute linear position sensor, as further described below with respect to FIGS. 6A-6D. In the exemplary variation depicted in FIG. 3D, the first idler gear 366 may have forty teeth and the dummy split gear 368 may have 31 teeth. Additionally, an even number (two, four, etc.) of idler gears may be included to adjust the directionality of the ball screw for desired travel. In other variations, the idler gear 366 and/or dummy split gear 368 may be omitted such that the motor drive gear 363 and the ball screw gear 365 are engaged directly with one another. The series of gears may be made of any suitable material, including but not limited to metallic materials such as steel (e.g., 304 stainless steel) and plastic materials such as polyoxymethylene (e.g., DELRIN) which has high stiffness and low friction. The bracket 322 may be mounted to the ball nut (or alternatively, the bracket may include threads so as to directly engage the ball screw such that the bracket acts as a ball nut) with fasteners, welding, or other suitable attachment mechanism or process. Alternatively, the bracket 322 may be omitted, such that the tool carriage is mounted to the ball nut directly. Accordingly, when the motor module 362 provides a rotational output, the series of gears (including motor drive gear 363, idler gear 366, and ball screw gear 365) are engaged and rotate to transfer the rotational output to the ball screw 364. When ball screw 364 rotates, it transforms the rotational motion into linear motion of the ball nut, bracket 322, and/or tool carriage (coupled to the ball nut or bracket) along the base 310. Commanded rotation of the motor module 362 in a first direction results in linear translation of the bracket 322 in one direction along the base 310 (e.g., in a distal direction), while commanded rotation of the motor module 362 in a second, opposite direction results in linear translation of the bracket 322 in an opposite direction along the base 310 (e.g., in a proximal direction).

Various electronics for controlling aspects of the base 310 may be coupled to the backbone 318, the proximal mounting block 391, distal mounting block 393, and/or any other suitable structure on the base 310. For example, as shown in FIG. 3B, a printed circuit board 374 (PCB) including electronics for controlling the linear actuator (e.g., motor module 362 and ball screw 364) may be coupled to the backbone member 318. As another example, a PCB 372 including other electronics may be coupled to another region of the backbone member 318, or may be combined with the PCB 374. Additionally, one or more cables 376 (e.g., flex circuits, ribbon cables) for transmitting signals to and from the tool carriage may be located near or on the backbone 318 (e.g., loosely tacked onto the backbone 318 with sufficient slack to accommodate movement of the tool carriage).

As best shown in FIG. 2A, the base may further include a housing 219, which may house or cover at least some of the above-described components, such as the backbone 318, motor module 362, and proximal mounting block 391. The housing may define, for example, an internal volume that accommodates the various components of the base described above. Additionally, there may be enough clearance between the components and the housing 219 to facilitate sufficient airflow for thermal management purposes. The housing 219 may be made of plastic or other suitable material, and may be injection molded, machined, or formed in any suitable manner to include a recessed internal volume. Furthermore, in some variations, as shown best in FIG. 2C, the housing may include one or more features (e.g., curved or semi-circular cutout 217) to improve physical clearance with the robotic arm to which the tool driver is attached, thereby increasing the available range of motion of the robotic surgical system.

As shown in FIG. 3A, the tool driver 310 may include an arm adapter 312 configured to couple the tool driver to a robotic arm. The arm adapter 312 may, for example, be located on distal mounting block 393 and include a hole configured to receive and couple to an output shaft of an actuator assembly disposed at a distal end of a robotic arm or other manipulator, such that when the actuator assembly on the robotic arm provides a rotational output, the tool driver 310 rotates correspondingly relative to the robotic arm. Alternatively, the arm adapter 312 may include an actuator assembly with an output shaft that couples to a distal end of a robotic arm, such that when the actuator assembly on the tool driver provides a rotational output, the tool driver 310 rotates relative to the robotic arm.

Generally, the tool driver 310 may further include a cannula adapter 314 configured to receive a cannula to permit the tool driver to couple to the cannula, such that the cannula and a shaft of the tool are aligned. The cannula adapter 314 allows for coupling of the tool driver and the cannula. In some variations, the cannula adapter 314 may require a deliberate user action to facilitate decoupling of the tool driver and the cannula (e.g., pushing a button, squeezing a latch release, etc.) to help avoid accidental or unintentional decoupling of the tool driver and the cannula. For example, various clamps or other retention devices may enable engagement and retention of the cannula to the cannula adapter. Exemplary variations of cannula adapters for coupling the tool driver to the cannula are described in U.S. Provisional Patent Application No. 62/548,292 titled "CANNULA ATTACHMENT DEVICES AND METHODS FOR A SURGICAL ROBOTIC SYSTEM" and filed Aug. 21, 2017, which is incorporated herein in its entirety by this reference.

Tool Carriage

Generally, the tool carriage is configured to provide various degrees of freedom of movement for the surgical tool coupled to the tool carriage. As described above, longitudinal movement of the tool carriage along the base provides a translational degree of freedom for the surgical tool along a tool axis. Additionally, the tool carriage may be configured to provide a rotational degree of freedom for rotation of the surgical tool around a tool axis, as well as various degrees of freedom for actuation or articulation of an end effector of the surgical tool (e.g., grasping or cutting). For example, the tool carriage may include one or more motor drives (e.g., linear axis drive or rotary axis drive) whose outputs may be coupled to the input driving mechanisms of a surgical tool, where a first motor drive may actuate a first degree of freedom (e.g., manipulate one jaw of a clamp end effector), a second motor drive may actuate a second degree of freedom (e.g., manipulate a second jaw of the clam end effector), and similar for additional motor drives in the tool carriage. Additionally, at least one motor drive may actuate rotation of the tool shaft in a first direction (e.g., clockwise) and another motor drive may actuate rotation of the tool shaft in a second direction opposite the first (e.g., counter-clockwise) in antagonistic fashion. Alternatively, at least one motor drive may actuate rotation of the tool shaft in two directions (e.g., both clockwise and counter-clockwise). Such actuation of the tool may involve, for example, a cable-driven mechanism or set of mechanisms in the tool that are coupled to the output of the motor drives in the tool carriage. Exemplary variations of the tool carriage are described below.

Combined Axis Drive Carriage Variation

In one variation, a tool carriage may include a combination of at least one linear axis drive and at least one rotary axis drive. For example, the tool carriage may include four linear axis drives configured to actuate a set of one or more articulated movements of the end effector of the tool (e.g., by a pusher that extends and retracts along a longitudinal axis of the pusher), and two rotary axis drives configured to rotate the tool shaft around a tool axis. However, other suitable numbers of linear axis drives and rotary axis drives may be included in any suitable combination in the tool carriage.

Figure 4A:
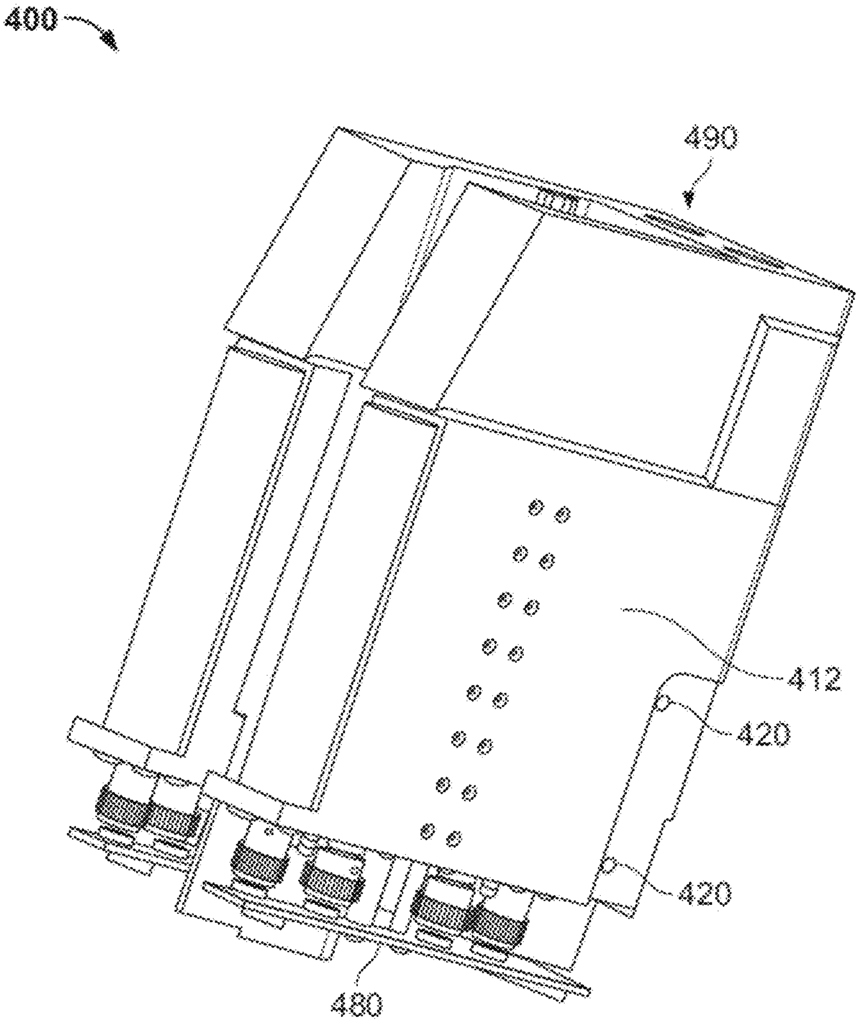
FIG. 4A is a perspective view of one variation of a tool carriage having combined linear axis drives and rotary axis drives.

As shown in FIG. 4A, a tool carriage 400 may include housing 412 which encloses the linear axis drives and/or rotary axis drives. A second housing (not shown) may further enclose the housing 412 and associated carriage electronics (e.g., PCB 480). The housing 412 may be configured to mount to the base or stage of the tool driver via fasteners insertable in mounting holes 420. For instance, the mounting holes 420 may be on both a left side and a right side of the carriage 400, and may be threaded so as to receive threaded screws or other fasteners that couple the housing 412 to a bracket on the base (e.g., bracket 322 on base 310, as shown in FIGS. 3A and 3B) or other suitable structure on the base. Additionally, the carriage 400 may be configured to receive a surgical tool. A sterile adapter 490 may generally be provided to create and maintain a sterile barrier between the non-sterile drive axes of the carriage 400 and a sterile surgical tool. Exemplary variations of sterile adapters are described in U.S. Provisional Patent Application No. 62/526,871 titled "STERILE ADAPTER FOR A LINEARLY-ACTUATING INSTRUMENT DRIVER" and filed Jun. 29, 2017, which is incorporated herein in its entirety by this reference.

Figure 4B:
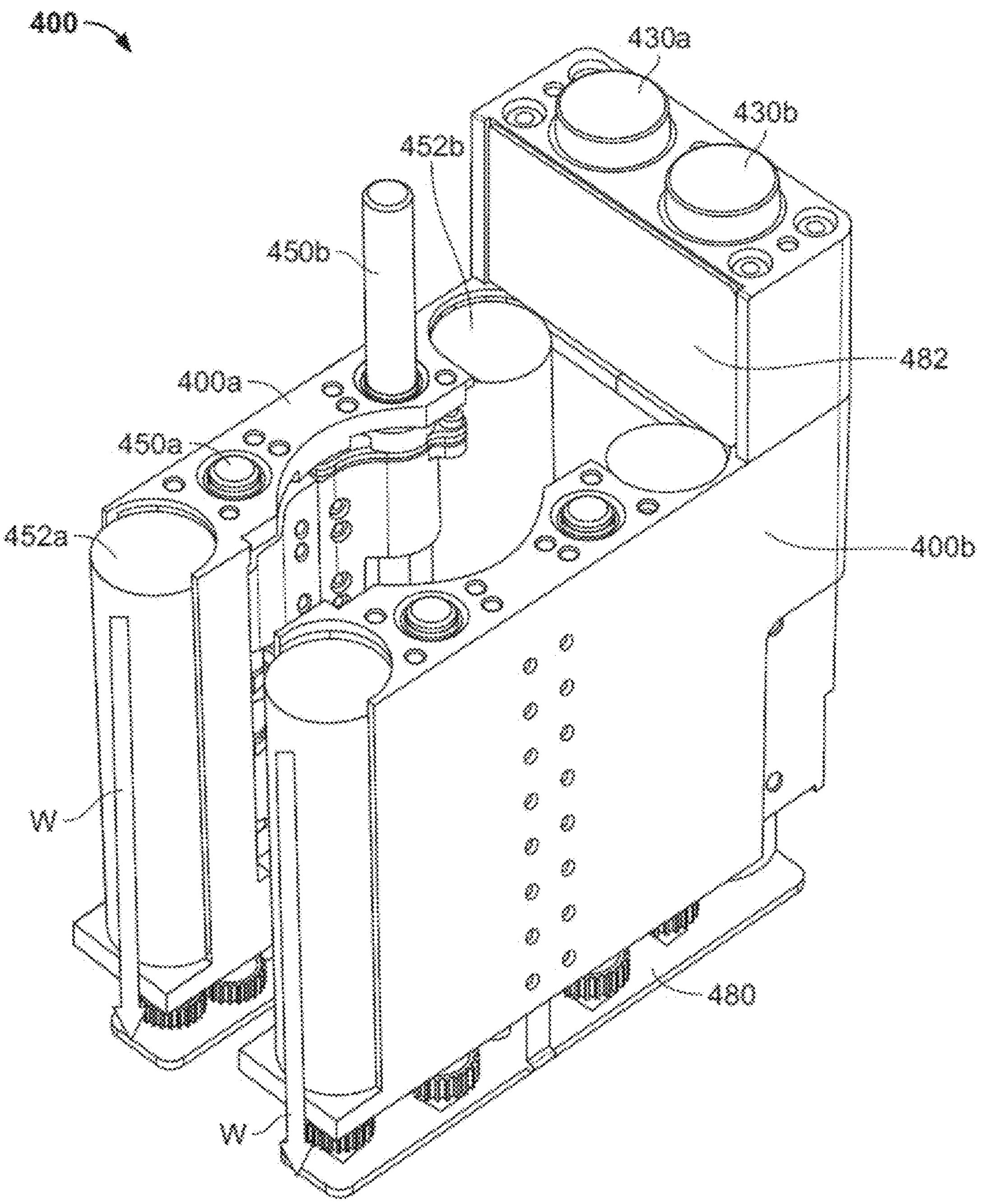
FIG. 4B is a perspective view of a partially disassembled version of the tool carriage depicted in FIG. 4A.
Figure 4C:
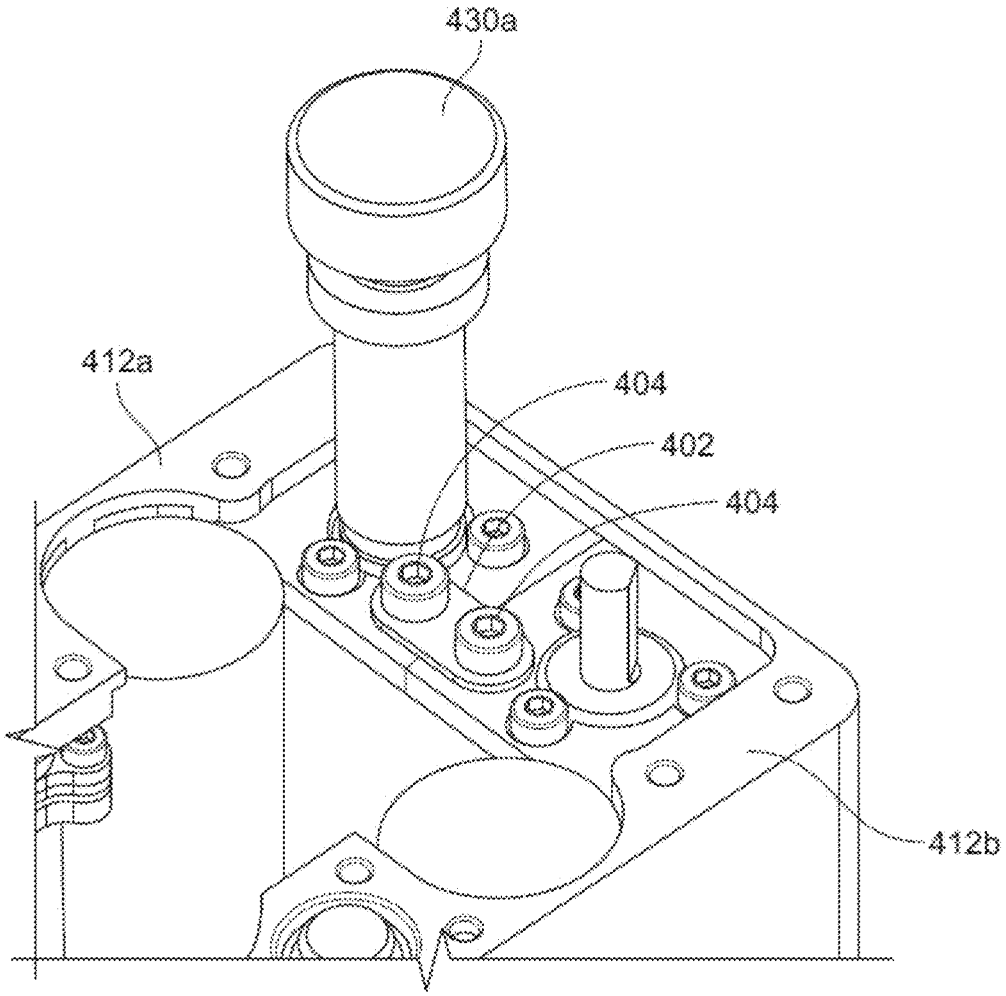
FIG. 4C is a perspective view of a rotary axis drive in the tool carriage depicted in FIG. 4B.

As shown in FIG. 4B (depicting the tool carriage 400 without the sterile adapter 490 and without top plate 410 of the housing 412), the carriage 400 may be bilaterally symmetrical. For example, a left side 400*a* of the carriage 400 may include a first linear axis drive 450*a* (shown in a retracted state), a second linear axis drive 450*b* (shown in an extended state), and a first rotary axis drive 430*a*. Similarly, a right side 400*b* of the carriage 400 may include a third linear axis drive 450*c*, a fourth linear axis drive 450*d*, and a second rotary axis drive 430*b*. The first side 400*a* and second side 400*b* of the carriage 400 may, for example, be mirrored halves of the carriage that are coupled together. Additionally, as shown in FIG. 4C, a left housing side 412*a* and a right housing side 412*b* in the carriage 400 may be coupled together with a joining plate 402 attached at both ends by fasteners 404 to the left and right housing sides 412*a* and 412*b*. Alternatively, the left and right housing sides 412*a* and 412*b* may be coupled together with interlocking geometry (e.g., tabs and slots), epoxy, or in any suitable manner.

Figure 4D:
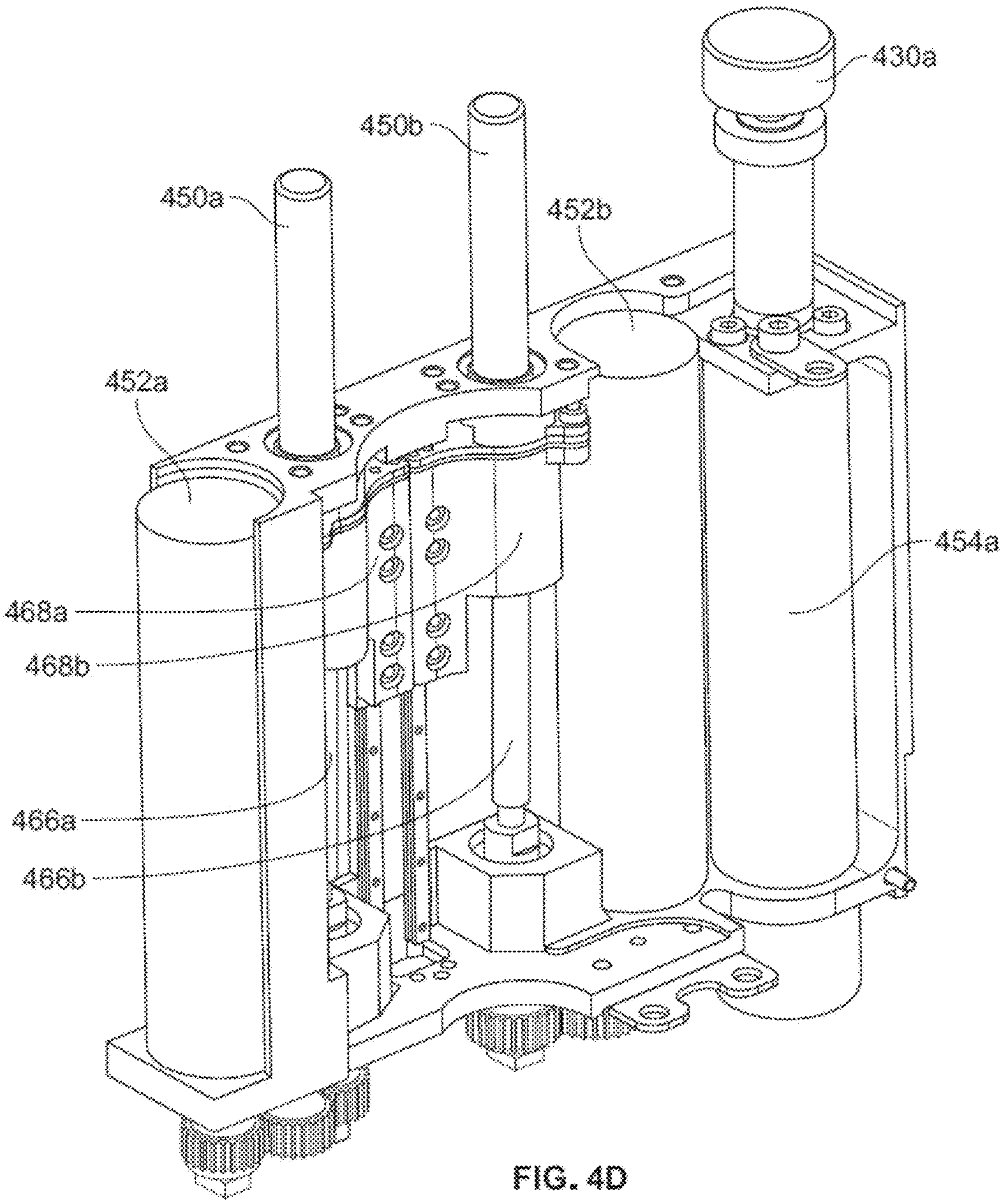
FIG. 4D is a perspective view of a left side of the tool carriage depicted in FIG. 4B.

An example of a left carriage side 400*a* is shown in FIG. 4D. Linear axis drive 450*a* is generally actuated by motor assembly 452*a*, and linear axis drive 450*b* is generally actuated by motor assembly 452*b* (e.g., motor assemblies 452*a* and 452*b* may be similar to that described with respect to FIG. 5A below). Rotary axis drive 430*a* is generally actuated by motor assembly 454*a* (e.g., described with respect to FIGS. 8A-8C below). A right carriage side 400*b* may be a similar, mirrored version of the left carriage side 400*a* (e.g., to simplify manufacturing for using common parts shared between the left and right carriage sides).

Figure 4E:
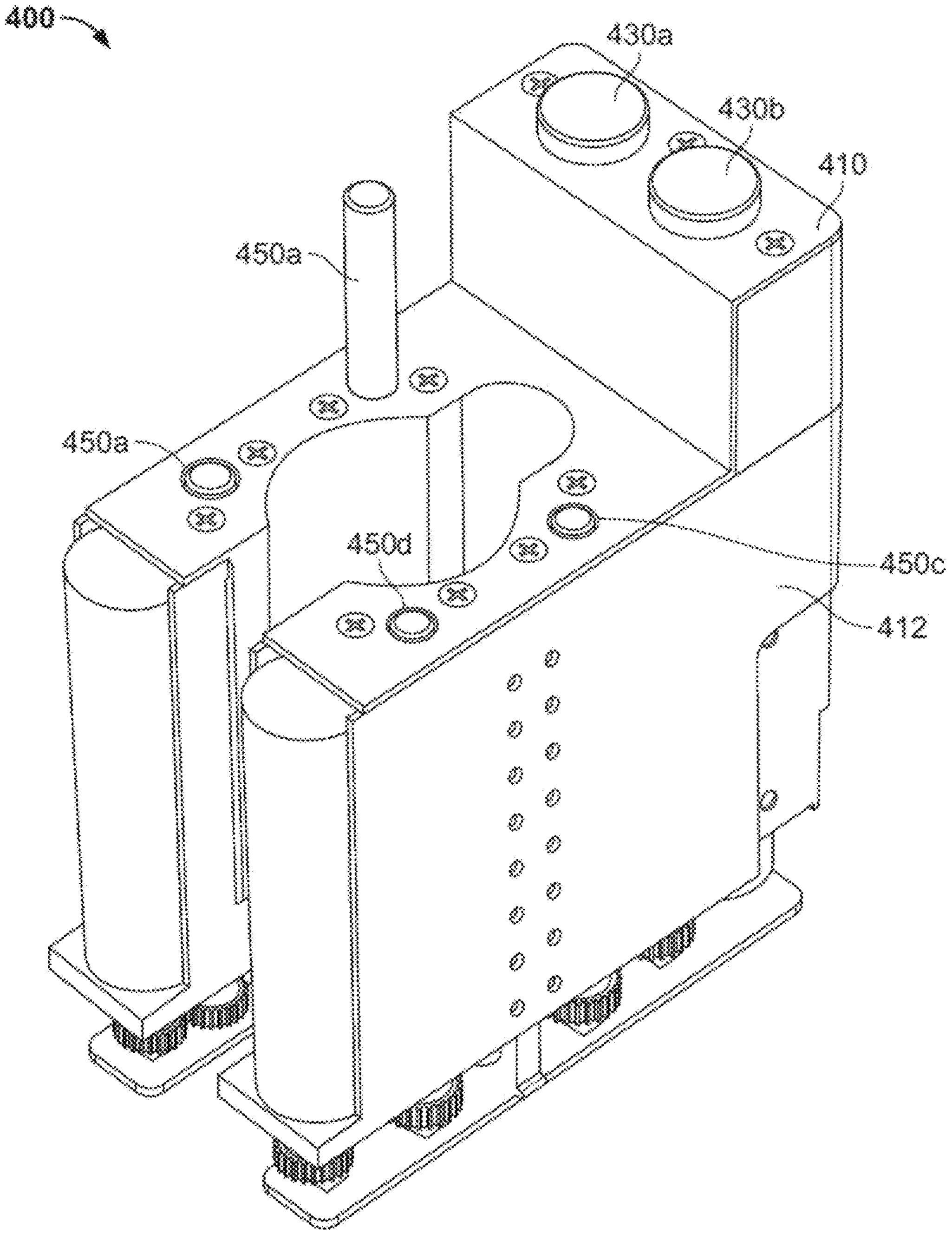
FIG. 4E is a perspective view of a version of the tool carriage depicted in FIG. 4B, with the addition of a top housing plate.

As shown in FIG. 4E (depicting the tool carriage 400 without the sterile adapter 490), in some variations, the tool carriage may include a top plate 410 that couples to the housing 412 via fasteners (e.g., screws) and is disposed between the housing 412 and the sterile adapter 490. The top plate 410 may include one or more openings to permit passage of the output of the linear axis drives (e.g., 450*a*, 450*b*, 450*c*, 450*d*) and/or the output of the rotary axis drives (e.g., 430*a*, 430*b*). Furthermore, the top plate 410 may include a single rigid or semi-rigid plate that is configured to help join together the mirrored right and left carriage sides of the tool carriage 400.

Linear Axis Drive

Figure 5A:
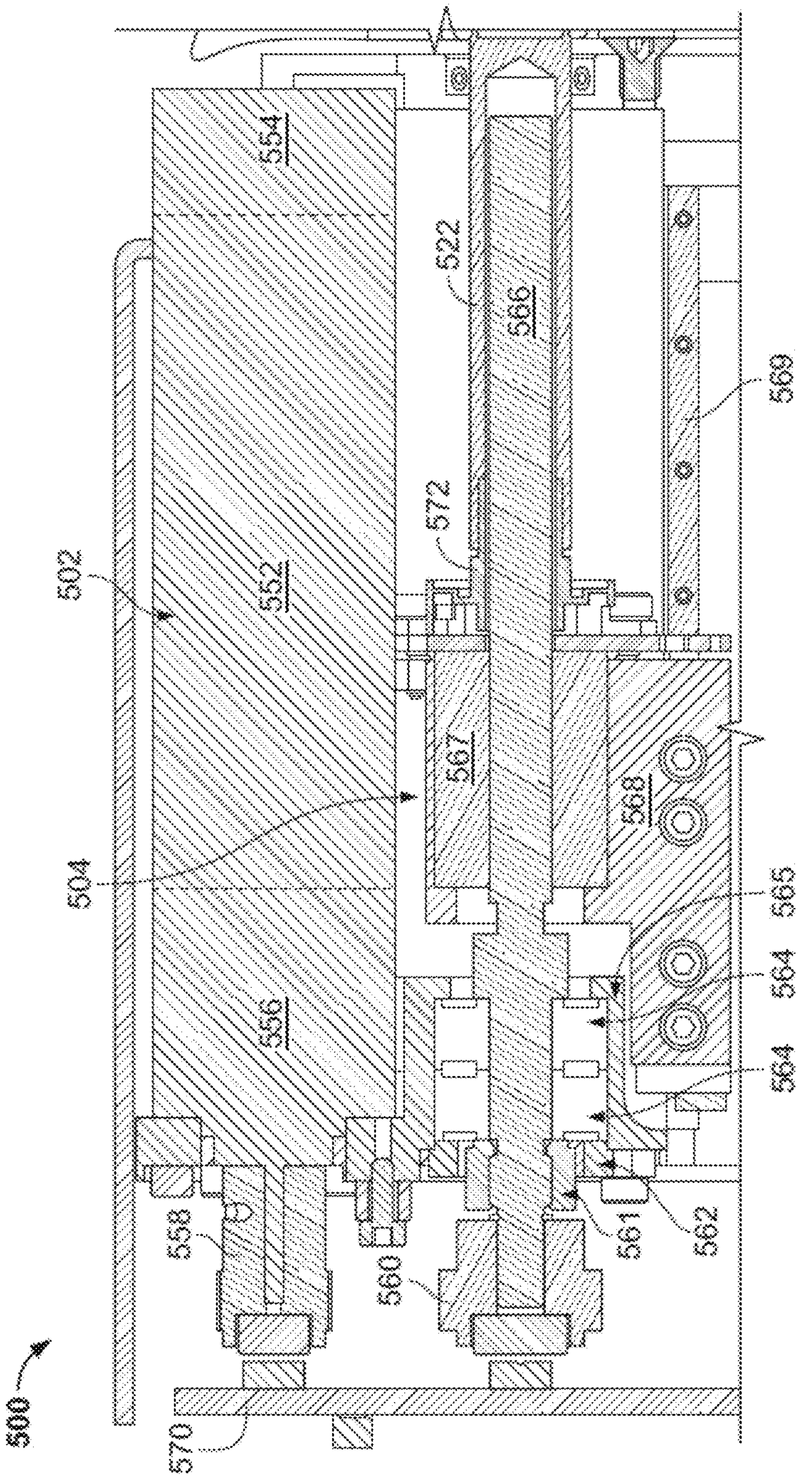
FIG. 5A is an illustrative schematic of a linear axis drive in one variation of a tool carriage.

As shown in FIG. 5A, an exemplary linear axis drive 500 includes a motor assembly 502, a ball screw assembly 504 driven by the motor assembly, and a pusher element 522 coupled to at least a portion of the ball screw assembly 504 and configured to move linearly. Multiple instances of the linear axis drive 500 may be included in the tool carriage, so as to provide actuation for multiple degrees of freedom of the tool.

In the linear axis drive 500, the motor assembly may include a motor 552 (e.g., a brushless DC motor or other suitable motor), a rotary encoder 554 configured to measure rotational or angular position of the motor shaft of the motor 552, and/or a gear transmission 556 (e.g., planetary gear train) configured to increase torque output of the motor assembly. The encoder 554 and/or the gear transmission 556 may be modular components of the motor assembly, such as with encoder 554 located at a proximal end of the motor 552 and the gear transmission 556 coupled to an output shaft of the motor 552. In other variations, the encoder 554 and/or the gear transmission 556 may be incorporated in the motor 552 (e.g., gear transmission 556 located in a rotor of the motor 552, as further described below with respect to FIG. 15A and 15B).

Figure 5B:
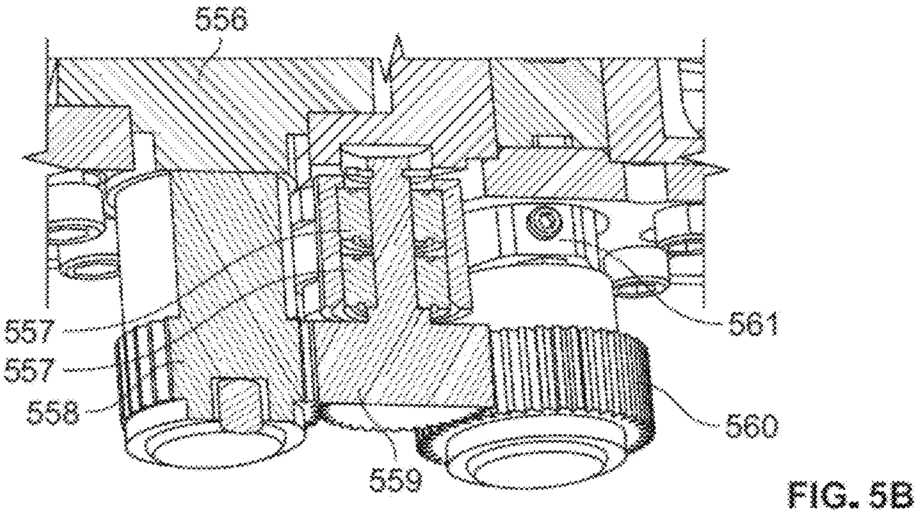
FIGS. 5B-5D are a partial cutaway view, a bottom side view, and a perspective view, respectively, of the linear axis drive gears and encoders in the variation of the tool carriage depicted in FIG. 5A.

The motor drive output of the motor assembly may be coupled to the input of the ball screw assembly via a series of gears, such that rotation of the motor assembly induces rotation of the ball screw in the ball screw assembly. For example, as shown best in FIGS. 5B and 5C, the series of gears may include a motor drive gear 558, such as a spur gear or other suitable gear, mounted to the output of the motor assembly (e.g., output shaft of gear transmission 556), an idler gear 459 mounted on bearings 557 and engaged with the motor drive gear 558, and a ball screw gear 560 engaged with the idler gear 559 and mounted to the input of ball screw 562. The number of teeth on the motor drive gear 558, the idler gear 559, and the ball screw gear 560 may be selected to optimize the design of the absolute multi-turn encoder (further described below) for measuring linear position of the ball nut or other linearly traveling elements. For example, in one exemplary variation depicted in FIG. 5C, the motor drive gear may have thirty-two teeth and the ball screw gear 560 may have thirty-nine teeth. Additionally or alternatively, the relative numbers of teeth on at least the motor drive gear 558 and the ball screw gear 560 may be selected to provide additional suitable torque increase. Additionally, an even number (two, four, etc.) of idler gears may be included to adjust the directionality of the ball screw for desired travel. The series of gears may be made of any suitable material, including but not limited to metallic materials such as steel (e.g., 304 stainless steel) and plastic materials such as polyoxymethylene (e.g., DELRIN) which has high stiffness and low friction.

The ball screw assembly converts the rotational output of the motor assembly into linear motion. As shown in FIG. 5A, the ball screw assembly includes a ball screw 566, and an axially-movable ball nut guide 568 threadingly mounted on and engaged with the ball screw 566. The axially-movable ball nut guide 568 may include, for example, a ball nut 567 engaged with the ball screw 566. The ball nut 567 may be a separate piece coupled to the rest of the guide 568 (e.g., with epoxy, interference fit, etc.) or may be integrally formed with the guide 568 (e.g., the guide 568 may include an internally threaded hole to engage with the ball screw 566). The ball screw 566 may be mounted at a proximal end to a ball screw mount portion 565 in the carriage housing, such as with an inner race clamp nut 561 and outer race clamp 562. Rotation of the ball screw 566 around a longitudinal axis of the ball screw 566 may be facilitated with one or more bearings 564. As described above, rotational output of the motor assembly induces rotation of the ball screw 566 in the ball screw assembly via a series of gears (motor drive gear 558, ball screw gear 560, etc.). When the ball screw 566 rotates, the ball nut 567 travels linearly along the ball screw 566. Ball nut guide 568, which is coupled to the ball nut 567, also travels linearly with the ball nut 547 along a ball nut guide rail 569 (e.g., linear bearing), which may, for example, help maintain linear alignment of the ball nut 567 and ball nut guide 568. In other variations, the linear axis drive may include a belt drive, a pulley-and-cable system, or the like in order to couple the rotational output of the motor assembly to the ball screw 566. Furthermore, in some variations, a leadscrew may be included in lieu of a ball screw.

As shown in FIG. 5A, a pusher element 522 is configured to travel linearly in correspondence with the ball nut 567 and ball nut guide 568. The pusher element 522 may be, for example, a cap or sleeve-like element with an internal volume or other space that receives a distal portion of the ball screw 566. When the ball nut 567 and ball nut guide 568 are in a proximal position (e.g., as shown in FIG. 5A), the pusher element 522 may be in a retracted state. In contrast, when the ball nut 567 and ball nut guide 568 are in a distal position (e.g., similar to ball nut guides 468*a* and 468*b* traveling on ball screws 466*a* and 466*b*, respectively, as shown in FIG. 4D), the pusher element may be in an extended state. Generally, rotation of the motor 552 in a first direction results in linear translation of the pusher element 522 (via the series of gears and the ball screw assembly) in one direction along the ball screw 566 (e.g., in a proximal direction), while rotation of the motor 552 in a second, opposite direction results in linear translation of the pusher element 522 in an opposite direction along the ball screw 566 (e.g., in a distal direction).

Rotary Axis Drive

Figure 8A:
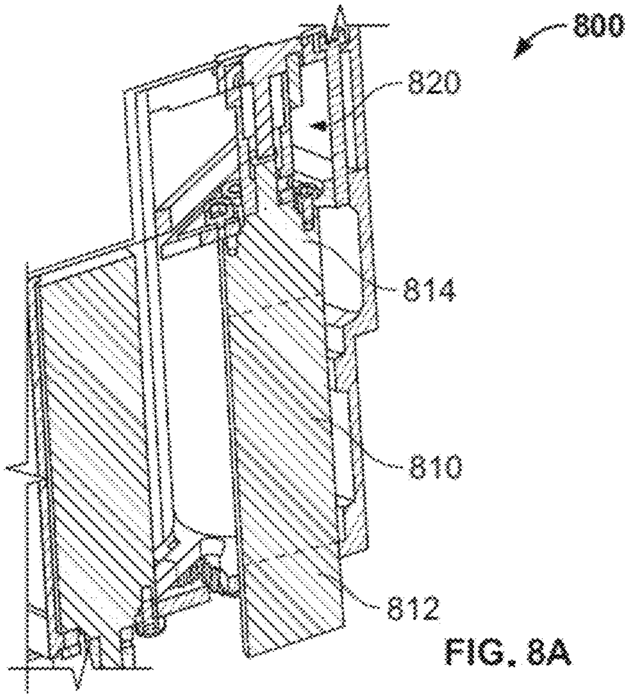
FIG. 8A is an axial cross-sectional view of a rotary axis drive in one variation of a tool carriage.
Figure 8B:
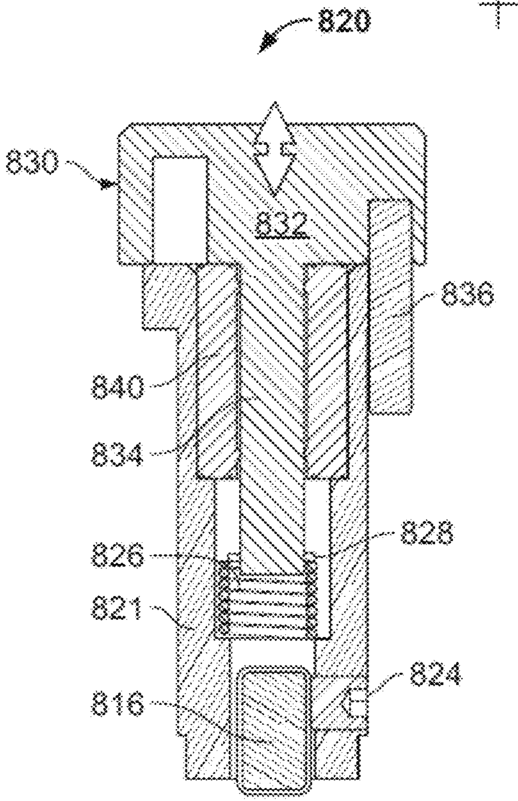
FIGS. 8B and 8C are a detailed longitudinal cross-sectional view and a detailed perspective view, respectively, of the rotary axis drive depicted in FIG. 8A.
Figure 8C:
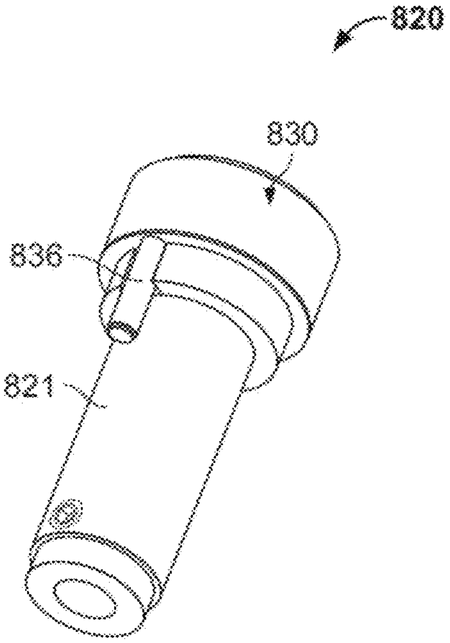

As shown in FIGS. 8A-8C, an exemplary rotary axis drive 800 includes a motor assembly and an output assembly 820 rotationally coupled to an output of the motor assembly. Multiple instances of the rotary axis drive 800 may be included in the tool carriage, so as to provide antagonistic rotational actuation of a surgical tool around a tool axis, and/or actuation for any other degree of freedom of the tool (e.g., articulation of an end effector of the tool).

Similar to the linear axis drive 500 shown in FIG. 5A, the motor assembly in the rotary axis drive 800 may include a motor 810 (e.g., a brushless DC motor or other suitable motor), a rotary encoder 812 configured to measure rotational or angular position of the motor shaft of the motor 810, and/or a gear transmission 814 (e.g., planetary gear train, harmonic drive, etc.) configured to increase torque output of the motor assembly. The encoder 812 and/or the gear transmission 814 may be modular components of the motor assembly, such as with encoder 812 located at a proximal end of the motor 810 and the gear transmission 814 coupled to an output shaft of the motor 810. In other variations, the encoder 812 and/or the gear transmission 814 may be incorporated in the motor 810 (e.g., gear transmission 814 located in a rotor of the motor 810, as further described below with respect to FIGS. 15A and 15B.

As shown in FIGS. 8B and 8C, the output assembly 820 may include a rotary shaft 821 that is coupled to an output shaft 816 (e.g., output shaft of a planetary gear train, or other output of a gear transmission 814) of the motor assembly, such as with one or more set screws 824. The output assembly 820 may further include a rotary axis drive output coupler 830, including a rotary axis drive output head 832 and a rotary axis drive output shaft 834, where the output coupler 830 is coupled to the rotary shaft 821 and configured to move in both rotational and translational (axial) manners. For rotational motion, the output head 832 of the output coupler 830 may be coupled to the rotary shaft 821 via a drive pin 836 operating similar to a mechanical key, such that the output head 832 rotates with the rotary shaft 821 whenever the motor assembly provides rotational actuation to the rotary shaft 821. For translational motion, the output shaft 834 may be coupled to a spring 826 for biased linear movement towards an extended, tool-engaging position. For example, a pre-loaded compression spring 826 may be disposed in a lumen of the rotary shaft 821 and coupled to the rotary axis drive output shaft 834 with a retaining ring 828 or other suitable mechanism. The spring 826 may be configured to urge the rotary drive output coupler outwards to an extended position, and one or more linear bearings 840 (e.g., bushing or sleeve bearing) may be provided to reduce friction of this translational movement. The extended position of the rotary drive output coupler may, for example, be conducive for engaging with the input of a surgical tool and/or sterile barrier located between the tool drive rand the tool, etc.

Carriage Sensors

In addition to or alternative to the various sensors briefly described above, any one or more linear axis drives rotary axis drives in the tool carriage may include other suitable sensor assemblies for measuring position, force (e.g., compression or tension) or other metrics. Such metrics may be used, for example, for tracking position and orientation of the various degrees of freedom of an end effector on the surgical tool, and/or as force feedback in control algorithms.

Absolute Multi-Turn Encoder

In some variations, the linear axis drive may further include one or more sensors configured to determine the axial (linear) position of the linearly traveling elements on the linear axis drive (e.g., ball nut 567, ball nut guide 568, and/or pusher element 522). Some variations of a tool driver may include, for example, a position sensor for measuring axial position of the guide based on relative rotational positions of gears, or any suitable position sensor (e.g., proximity sensors, tracking markers, etc.).

For example, as shown in FIG. 5A, the linear axis drive 500 may include an absolute multi-turn encoder 570 leveraging the Vernier principle. The absolute multi-turn encoder may determine the relative rotational positions (angular orientation) of at least two gears in the linear axis drive, which may be mapped to an absolute linear position of the linearly traveling elements on the linear axis drive. Alternatively, one or more suitable encoders or other sensors may be used to detect the rotational position of the output of the motor 552 or motor assembly, and/or rotational position of the motor drive gear 558, idler gear 559, and/or ball screw gear 560, which may be transformed into a linear position sensor. For example, an encoder may measure the rotational position of the ball screw gear 560 alone, and a processor may convert the rotational position to a linear position of one or more of the linearly traveling elements. In some variations, such an encoder may need to be zeroed (e.g., during calibration or setup) to set a reference point relative to which dynamic linear position is measured. Advantageously, in the applications described herein, as well as in other suitable applications in which a linearly traveling element (e.g., ball nut on a ball screw or leadscrew, etc.) is driven by a rotational element, an absolute multi-turn encoder may be used to measure linear position of the linearly traveling element without requiring a sensor directly on the linearly traveling element. Accordingly, electronics for the absolute multi-turn encoder may be relatively simplified and compact, such as contained on a PCB mounted next to the rotational element, in contrast to typical sensor electronics that require physical accommodations for communicating with a linearly traveling sensor (e.g., with flex cables between a PCB and the linearly traveling sensor, etc.).

Figure 5C:
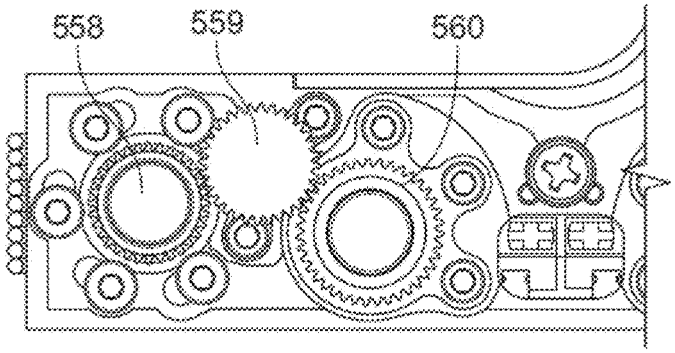
Figure 6A:
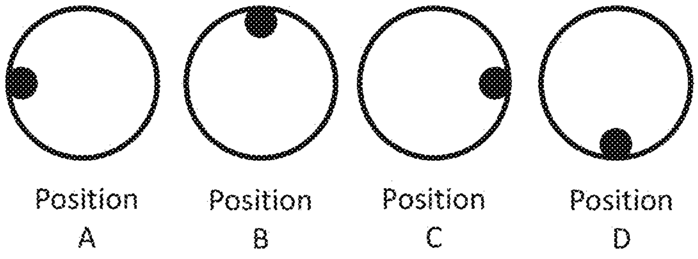
FIGS. 6A-6D are illustrative schematics of one variation of a multi-turn absolute encoder sensor.
Figure 6B:
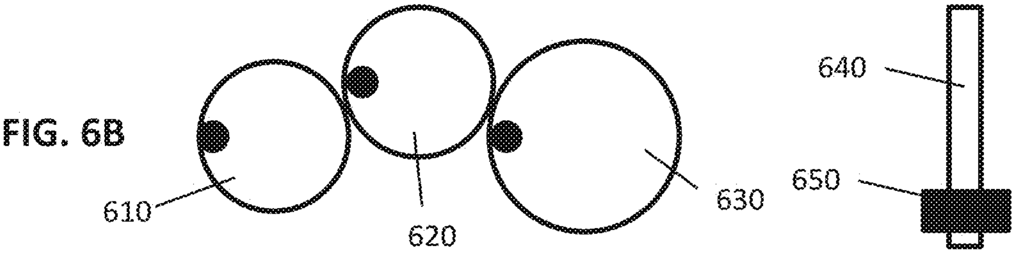
Figure 6C:
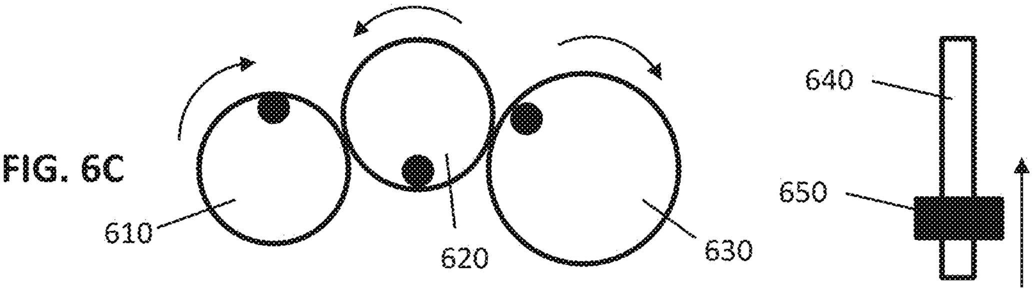
Figure 6D:
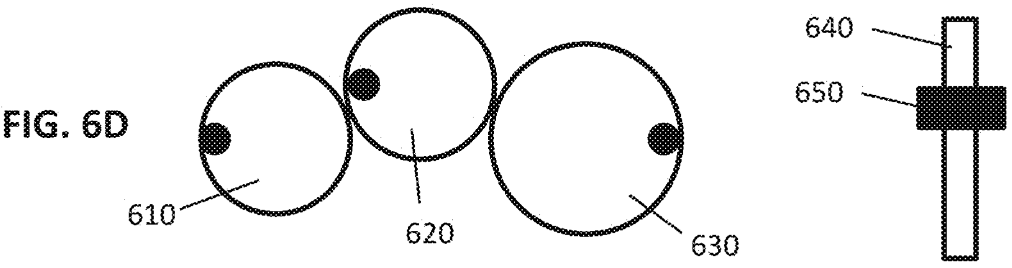

Generally, in the absolute multi-turn encoder, the respective rotational positions of at least two gears may be measured and used in combination to determine the number of total and partial turns that one of the gears has rotated, which may be used to determine a measure of absolute position relative to a zero position. The principle of operation of the absolute multi-turn encoder for measuring absolute linear position is illustrated in the schematic of FIGS. 6B-6D, which depict a first measured gear 610, an idler gear 620 engaged with the first measured gear 610, and a second measured gear 630 engaged with the idler gear 620 and having a different number of teeth than the first measured gear 610. Like the motor drive gear 558 shown in FIG. 5C, the first measured gear 610 may be coupled to an output of a motor assembly. Additionally, like the ball screw gear 560 shown in FIG. 5C, the second measured gear 630 may be coupled to a ball screw, such as ball screw 640 with linearly traveling ball nut 650. Additionally, like the idler gear 559 shown in FIG. 5C, the idler gear 620 may be engaged with the first measured gear 610 on one side and with the second measured gear 620 on another side. However, the idler gear 620 may be omitted in some variations. Each gear may have any rotational position (angular orientation), such as any of those shown in FIG. 6A, including a position A, a position B which is rotated 90 degrees clockwise from position A, position C which is rotated 90 degrees clockwise from position B, or position D which is rotated 90 degrees clockwise from position C, or any rotational position between any of these positions. FIG. 6B depicts the first measured gear 610, the idler gear 620, and the second measured gear 630 in position A, which may correspond to a first location of the ball nut 650 on the ball screw 640. The gear orientations in FIG. 6B may, for example, be considered a "zero" absolute position. In FIG. 6C, the first measured gear 610 has rotated clockwise to position B, causing the idler gear 620 to rotate counter-clockwise to position D. The second measured gear 620 has rotated clockwise to a position intermediate between positions A and B (a smaller degree of rotation due to the second measured gear 620 having more teeth than the idler gear 620), resulting in the ball nut 650 traveling to a second location (e.g., distal to the first location) of the ball nut 650 on the ball screw 640. Continued rotation of the first measured gear 610, idler gear 620, and second measured gear 630 may further drive the ball nut 650 to more distal locations on the ball screw 640, until the configuration shown in FIG. 6D. In FIG. 6D, the first measured gear 610 and the idler gear 620 have returned to position A, while the second measured gear 630 is in position C, resulting in the ball nut 650 traveling to a third location (e.g., distal to the second location) of the ball nut 650 on the ball screw 640. Comparing the gear orientations in FIGS. 6B and 6D, although in both FIGS. 6B and 6D the first measured gear 610 and the idler gear 620 are in position A, the second measured gear 630 is in position A in FIG. 6A and in position D in FIG. 6D. The different position of the second measured gear 630 in FIG. 6D indicates that the first measured gear 610 has rotated (here, rotated a full single turn) relative to FIG. 6B, which could not be determined without determining the position of second measured gear 630. Accordingly, the combined set of rotational positions of the first measured gear 610 and the second measured gear 630 in FIG. 6B is distinct from the combined set in FIG. 6D, which when measured enables determination of distinct linear positions of the ball nut 650 on the ball screw 640.

Furthermore, in the absolute multi-turn encoder, the total number of measurable turns (and/or measurable range of linear movement, if paired with a ball screw or leadscrew) is based at least partially on the gear ratio between the measured gears. The measurement of the rotational position of the first measured gear 610 and the second measured gear 630 (or alternatively or additionally the idler gear 620) may be mapped to an absolute linear position of the ball nut 650 within a certain range that is limited by the possible amount of "wrap," or continued rotation of the gears, before the gears return to the zero absolute position. In other words, if the smaller measured gear has "m" teeth and the larger measured gear as "n" teeth (where m<n), then the encoder can discriminate rotational positions of the gears throughout "n" turns of the smaller gear. Different gear ratios (i.e., the numbers of teeth of the measured gears) may be selected at least in part to obtain a suitable measurable range of absolute position. Furthermore, the idler gear 620 may be omitted, or replaced by a split idler gear (e.g., described with respect to FIG. 5D) to increase the absolute distance or position that is measurable by the absolute multi-turn encoder (by increasing the number of possible turns before the series of gears collectively return to the zero absolute positions) without requiring an increase in the size of the measured gears 610 and 630.

Thus, the absolute multi-turn encoder may be a compact, space- and part-efficient way to enable detection of an absolute rotation angle of a shaft and/or gears with high precision (high resolution). In some variations, the encoder may detect absolute rotational position within about 0.1 degree precision, within about 0.05 degree precision, or within about 0.03 degree precision. The multi-turn encoder may be used alone to determine rotational position of shafts. Additionally, when used in combination with a ball screw or leadscrew (e.g., at shown in FIG. 5A), the geometric relationship between the gears and the ball screw or leadscrew may enable measurement of the absolute linear position of the ball screw or leadscrew with similarly high precision (e.g., a resolution or precision within less than 50 μm, less than 45 μm, less than 40 μm, less than 30 μm, or 25 μm or less, etc.). Furthermore, the encoder may enable measurement of an absolute position within a range that is larger than that of typical encoders (e.g., that are based on measurement of a single rotational position). Advantageously, the absolute multi-turn encoder may not require zeroing or recalibration in order to determine rotational position.

The absolute multi-turn encoder may be convenient to implement in systems that already include a gear train, but may still be incorporated in systems with no gears or an insufficient number of gears, by introducing "dummy" gears (e.g., gears not driving anything, and are rotationally driven simply for purposes of providing information for the multi-turn encoder). For example, to measure rotational position of an output shaft in a system not requiring a gear train, a set of at least two dummy gears may be introduced, with one dummy gear attached to the output shaft. As another example, if a higher number of turns (and larger measurable range of position) is desired without increasing the number of teeth on the gears in the gear train, a fractional gear ratio may be introduced by including a dummy split gear (e.g., gear 368 as shown in FIG. 3D).

Figure 5D:
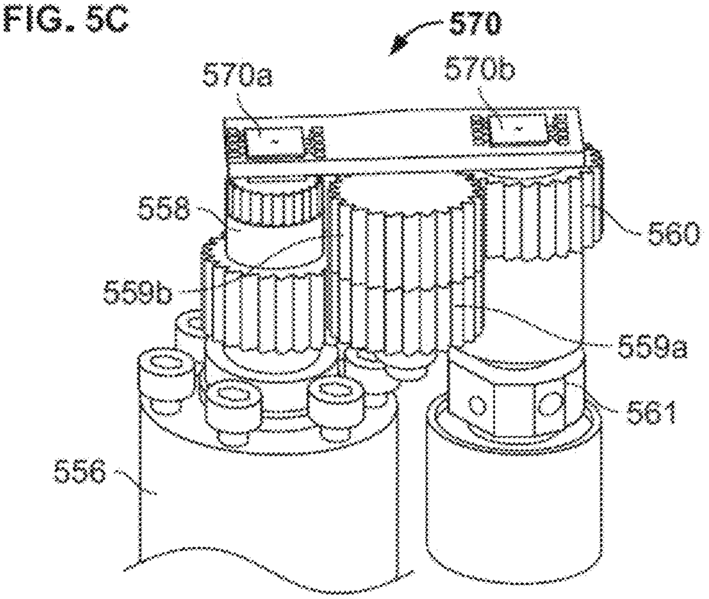

In an exemplary implementation, as shown in FIG. 5A, the magnetic encoder 570 may be an absolute multi-turn encoder. As best shown in FIG. 5D, the magnetic encoder 570 may be configured to detect the relative angular orientation of at least two gears in the linear axis drive, such as with a sensor 570*a* detecting angular orientation of the motor drive gear 558 and a sensor 570*b* detecting angular orientation of the ball screw gear 560 (e.g., via magnets and Hall effect sensors, or other suitable rotary encoders for each measured gear). A relationship between the set of angular orientations of the gears 558 and 560 and the linear position of the linearly traveling elements (e.g., ball nut 567, ball nut guide 568, and/or pusher element 522) may be determined, based on the number of teeth on the gears 558 and 560 and on the thread characteristics of the ball screw 566 (e.g., thread angle, pitch). Accordingly, measurement of the angular orientation of the gears 558 and 560 (or additionally or alternatively idler gear 559) may be transformed or mapped into information regarding the absolute linear position of the linearly traveling elements, at least within a certain measurable range. The measurable range of absolute linear position may be based on, for example, the relative number of teeth of the measured gears and/or pitch of the gears. For example, as depicted in FIG. 5C, the motor drive gear 558 may have thirty-two teeth and the ball screw gear 560 may have thirty-nine teeth. This exemplary ratio (32:39) results in the ball screw gear 560 "wrapping" to a reference zero position every thirty-two revolutions of the ball screw gear 560, which limits the measurable absolute distance of the linearly traveling elements. In an exemplary variation in which the ball screw gear 560 has a pitch of about 1 mm, the measurable range of absolute linear position of about 32 mm, with e.g., about 25 μm of resolution.

In some variations, as shown in FIG. 5D, the series of gears for the absolute multi-turn encoder may include split idler gears including a first idler gear 559*a* and a second idler gear 559*b*, where the first idler gear 559*a* is engaged with the motor drive gear 558, the second idler gear 559*b* is rotating with the first idler gear 559*a* about the same axis, and the second idler gear 559*b* is engaged with the ball screw gear 560. The first idler gear 559*a* and the second idler gear 559*b* may have different numbers of teeth (e.g., the second idler gear 559*b* may have fewer teeth than the first idler gear 559*a*, or may have more teeth than the first idler gear 559*a*) to further facilitate a particular gear ratio. Additionally or alternatively, the first and second idler gears 559*a* and 559*b* may further increase the absolute distance or position that is measurable by the absolute multi-turn encoder (by increasing the number of possible turns before the series of gears collectively return to the zero absolute positions) without requiring an increase in the size of the motor drive gear 558 and/or ball screw gear 560.

In some variations, the motor drive gear 558 may have between 10 and 25 teeth, or between 15 and 20 teeth, etc., the first and/or second idler gears 559*a* and 559*b* may have between 25 and 45 teeth, or between 30 and 40 teeth, etc., and the ball screw gear 560 may include between 15 and 45 teeth, between 25 and 35 teeth, etc. Additionally, in some variations, the series of gears for the absolute multi-turn encoder may enable between 100 and 200 turns, between 110 and 175 turns, or between 120 and 150 turns, etc. before returning to the zero absolute positions. Other suitable combinations of gears may facilitate a suitable gear ratio and a suitable measurable number of turns (correlating to measurable absolute distance). For example, the motor drive gear 558 may include seventeen teeth, the first idler gear 559*a* may include thirty-six teeth, the second idler gear 559*b* may include thirty-two teeth, and the ball screw gear 560 may include twenty-seven teeth, which provides a gear ratio of about 1.79 and over 135 turns' worth of measurable absolute distance. As another example, the motor drive gear 558 may include seventeen teeth, the first idler gear 559*a* may include thirty-six teeth, the second idler gear 559*b* may include thirty-two teeth, and the ball screw gear 560 may include twenty-nine teeth, which provides a gear ratio of about 1.92 and over 135 turns' worth of measurable absolute distance. As yet another example, the motor drive gear 558 may include seventeen teeth, the first idler gear 559*a* may include thirty-six teeth, the second idler gear 559*b* may include thirty-two teeth, and the ball screw gear 560 may include thirty-one teeth, which provides a gear ratio of about 2.05 and 136 turns' worth of measurable absolute distance.

Furthermore, the absolute multi-turn encoder may be implemented in other parts of the tool driver. For example, as discussed above, the absolute multi-turn encoder may be used to measure absolute linear position of the carriage on the stage (e.g., using the gear train shown in FIG. 3D). The absolute multi-turn encoder may be implemented in other variations of the tool driver (e.g., other variations of the carriage) or other applications in which it is desirable to measure rotational position and/or linear position.

Compact Load Cell

In some variations, the linear axis drive may include one or more force sensors configured to determine the axial load placed on the linear axis drive (e.g., ball screw), which may be used as feedback in controlling the linear axis drive in the tool drive. For example, as shown in FIG. 5A, a load cell 570 may be disposed on the ball screw distal to the ball screw nut 567 and proximal to the pusher element 522, such that the load cell 570 is configured to measure axial loads (push and/or pull forces) on the ball screw. The space distal to the ball screw nut is very limited and it is difficult to place a conventional load cell in the space between the ball screw nut 567 and the pusher element 522. Thus, in some variations, the load cell 570 may include a compact, hollow load cell such as the capacitive compact load cell 700 shown in FIGS. 7A-7F.

The capacitive compact load cell 700 described herein have a number of additional advantages. For example, in the applications described herein and in other applications in which axial load is to be measured, the capacitive compact load cell 700 may provide a data signal that is more robust against noise (e.g., due to electromagnetic interference, temperature variation and/or humidity variation, etc.) than conventional strain gauge-based load cells. For example, conventional strain gauge load cells typically provide raw signal data with low amplitude (i.e., low voltage ranges) which, for practical purposes, must be processed with analog and/or digital amplifiers to provide useful information. Furthermore, since the signal-to-noise ratio is low, noise in the raw sensor data is also amplified, such that further signal processing with filters and other complicated circuitry or digital processing methods must also be performed on the signal to isolate the force data. In contrast, the capacitive compact load cell 700 provides raw capacitance signal that has a relatively high amplitude (e.g., higher voltage ranges), or a high signal-to-noise ratio, thereby making the capacitive compact load cell 700 more immune or resilient against noise. Additionally, the high signal-to-noise ratio facilitates straightforward, simple calibration of the signal output. Furthermore, as described below, the load cell 700 includes a small number of parts that are straightforward and easy to manufacture and assemble.

Figure 7A:
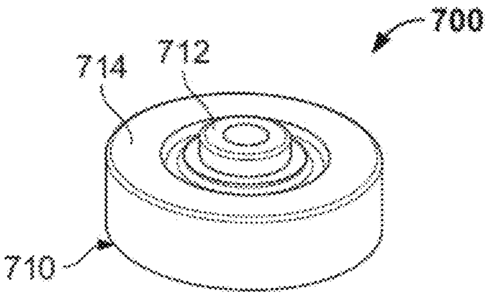
FIG. 7A is a perspective view of a compact load cell, such as for use in a linear axis drive in one variation of the tool carriage.
Figure 7B:
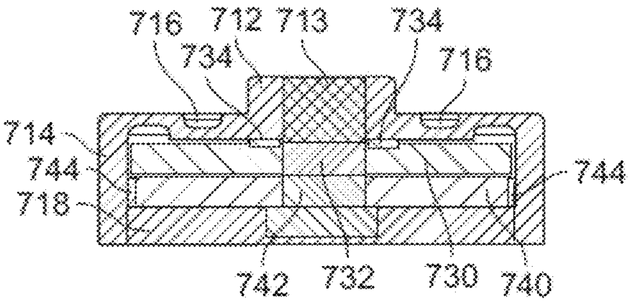
FIG. 7B is a longitudinal cross-sectional view of the load cell depicted in FIG. 7A.
Figure 7C:
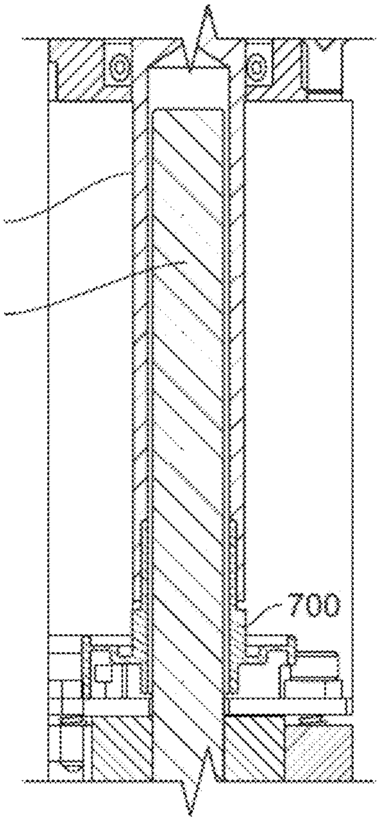
FIG. 7C is an illustrative schematic of the load cell depicted in FIG. 7A, implemented in one variation of a linear axis drive.
Figure 7D:
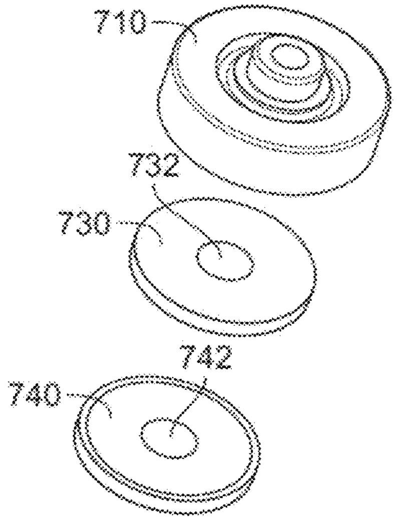
FIGS. 7D and 7E are exploded perspective views of the load cell depicted in FIG. 7A.

Generally, in one variation as shown in FIGS. 7A-7E, a compact load cell 700 includes a housing 710 with a recess 718, a first conductive plate 730 disposed in the recess 718, and a second conductive plate 740 disposed in the recess 718 and facing the first conductive plate 730. As shown in FIG. 7B, the housing 710 includes a central region 712, an outer region 714, and a spring structure 716 connecting the central region 712 and the outer region 714 such that the central and outer regions of the housing 710 may flex relative to one another. The central region 712 may be configured to receive an axial load directed along a centerline of the load cell. For example, as shown in FIG. 7B, the central region 712 may include an opening 713. The opening 713 may be internally threaded to receive and engage with a ball screw 780 (or leadscrew), as shown in FIG. 7C. Accordingly, in the example shown in FIG. 7C, when the ball screw 780 receives an axial load (i.e., a proximally-directed or distally-directed) while threadingly engaged with the central housing region 712 via opening 713, the axial load causes deflection of the spring 716. In other examples, the central region 712 may include a ball seat (or groove or other surface engagement) configured to receive a load-receiving member.

The housing 710 may, in some variations, be made from a single unitary part. It may be manufactured through any suitable machining process (e.g., with a mill, lathe, etc.), casting, or other suitable manufacturing process to include the desired compact shape, geometry of the central region 712 and outer region 714, geometry of the spring structure 716, thread characteristics of the opening 713, etc. Alternatively, the housing may include multiple parts (e.g., separate central region 712 and outer region 714 sections) that are assembled and joined together to form the housing. The housing may be made of a suitable material that provides electromagnetic shielding for the conductive plates and associated electronics disposed within the housing 710, such as aluminum or steel, to reduce electromagnetic noise that might confound sensor readings.

As shown in FIG. 7B, the first conductive plate 730 and the second conductive plate 740 may be disposed within the recess 718 of the housing 710 and arranged to face each other. In some variations, the first conductive plate 730 may include an opening 732, and the second conductive plate 740 may include an opening 742, where the openings 732 and 742 are aligned with the opening 713 such that the ball screw 780 may pass through the housing 710 (by passing through threaded opening 713), through the first conductive plate 730 (by passing through the opening 732), and through the second conductive plate 740 (by passing through the opening 742). As such, the openings 732 and 742 in the first and second conductive plates may be of sufficiently larger diameter than the opening 713 in the central region 712 of the housing, to enable the ball screw 780 to pass with clearance.

One of the conductive plates (e.g., the second conductive plate 740) may be the "active" or "sensor" conductive plate, and include electronics 750 for measuring the capacitance between the first and second conductive plates. In some variations, the electronics 750 may include multiple active signal channels (e.g., two, three, four, five, six, etc.) for redundancy purposes. For example, if one or more of the active signal channels returns an error (no signal, signal outside a predetermined acceptable signal range, etc.), then force data from at least one other functioning active signal channel may be used instead. Furthermore, co-location of the electronics 750 on the sensor (on one or more conductive plates) may be advantageous. For example, such a co-located arrangement of the electronics 750 may enable the housing 710 to substantially surround the electronics 750 and provide electromagnetic shielding against noise. As another example, the electronics 750 located on the sensor may reduce or eliminate the need for wiring to communicate signals between the sensor and an additional PCB located external to the housing 710.

The first conductive plate 730 may be coupled to the central region 712 of the housing 710 (e.g., by epoxy or other fastener at locations 734). The second conductive plate 740 may be coupled to the outer region 714 of the housing 710 (e.g., by epoxy or other fastener at locations 744) such that the first and second conductive plates 730 and 740 are substantially parallel to one another. As another example, as shown in the variation of the load cell 700' depicted in FIG. 7I, at least one of the conductive plates (e.g., second conductive plate 740) may include one or more radially extending extensions or tabs 747 that are configured to engage cutouts 715 in the outer region 714 of the housing. Such tabs 747 may help restrain rotational motion relative to the housing 710 and/or help couple, for example, the second conductive plate 740 to the housing 710.

Figure 7E:
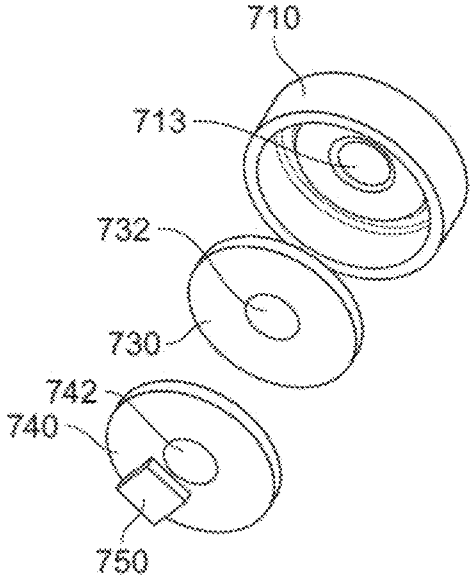
Figure 7F:
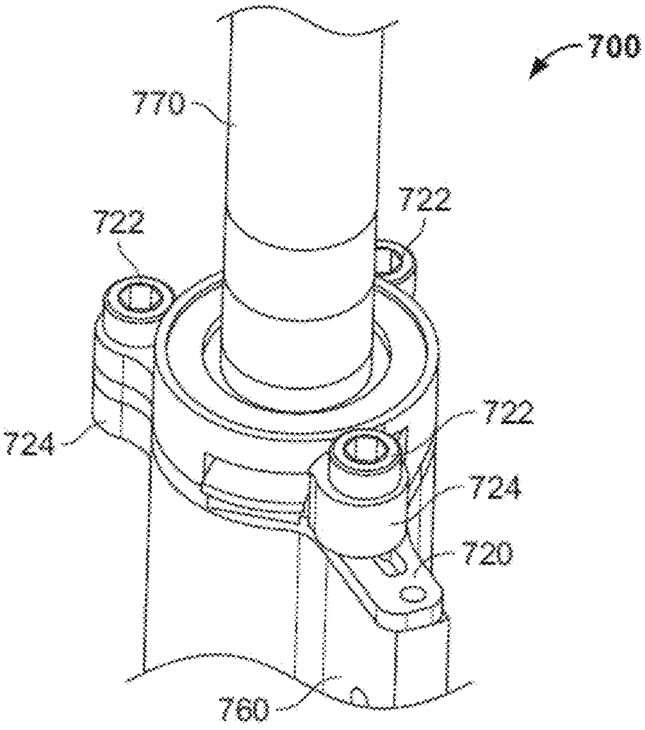
FIGS. 7F and 7G are perspective views of the load cell depicted in FIG. 7A mounted in one variation of a linear axis drive.
Figure 7G:
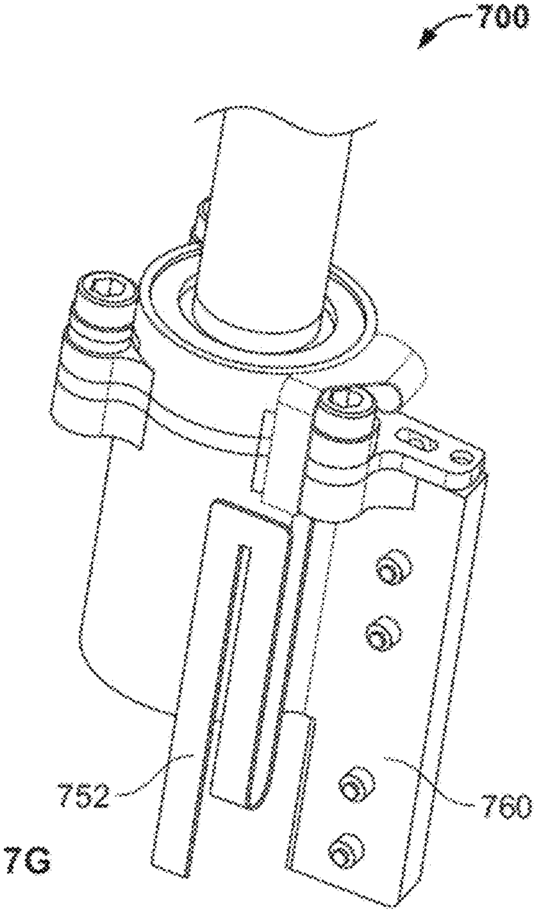
Figure 7H:
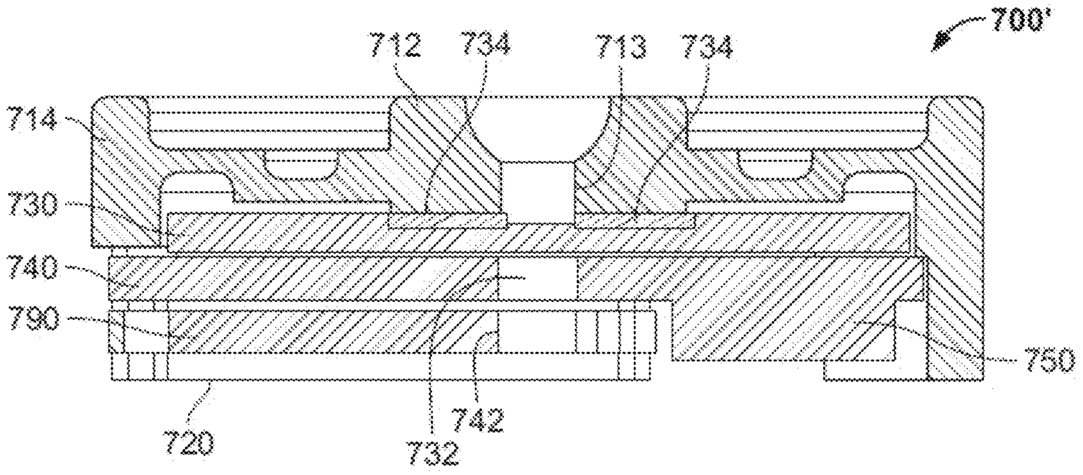
FIGS. 7H and 7I are a longitudinal cross-sectional view and an exploded perspective view, respectively, of another variation of a compact load cell including a reference capacitive plate.
Figure 7I:
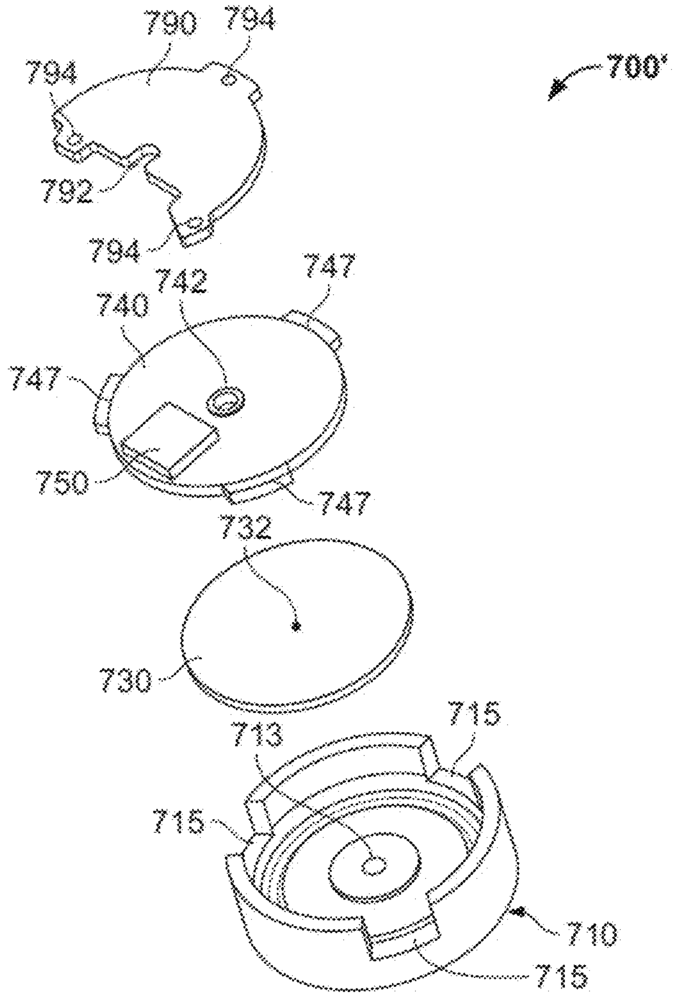

In some variations, such as load cell 700' as shown in FIGS. 7H and 7I, the load cell 700' may be similar to load cell 700 described with reference to FIGS. 7A-7E, except as described below. Load cell 700' may include a third conductive plate or reference conductive plate 790 which may serve as a reference pad for temperature and/or humidity calibration (e.g., to compensate for temperature, humidity, and other environmental variations). The reference conductive plate 790 may be configured to be adjacent to a second face of the second conductive plate 740, where the second face is directed away from the first conductive plate 730, such that as shown in FIG. 7H, the second conductive plate 740 is disposed between the first conductive plate 730 and the reference conductive plate 790. The reference conductive plate 790 may be mounted, for example, to the outer region 714 of the housing via pins engaging peripherally-arranged mounting holes 794. Additionally, the electronics 750 may include a reference channel (e.g., corresponding to capacitance measured between a reference conductive plate 790 and the active second conductive plate 740) that communicates a signal that includes information that may be used for calibration against temperature and/or humidity variations.

Figure 7J:
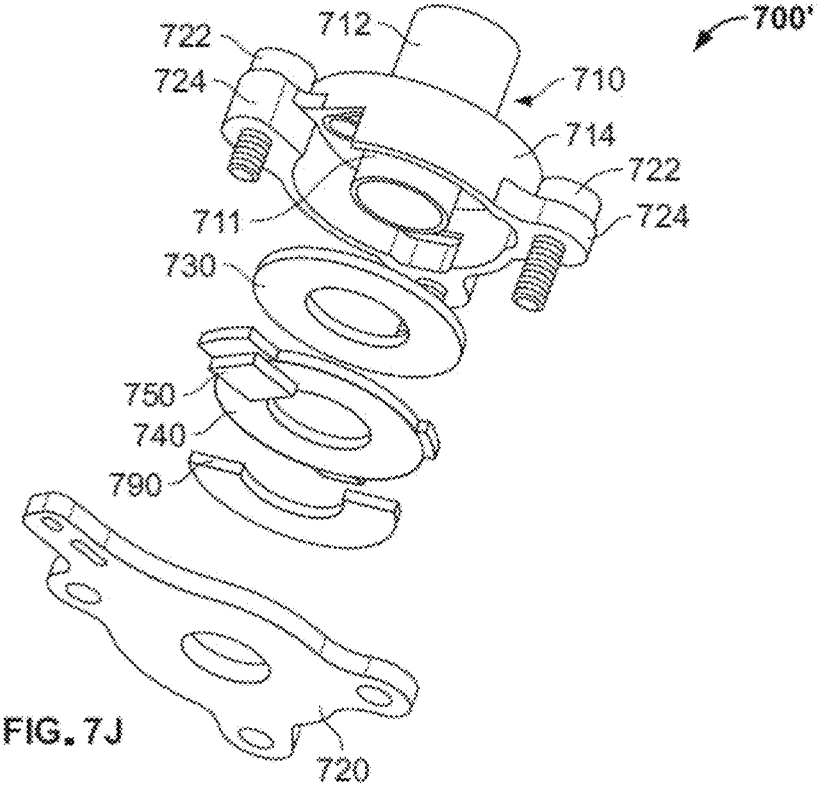
FIGS. 7J and 7K are an exploded perspective view and a longitudinal cross-sectional view, respectively, of the variation of the load cell depicted in FIG. 7H for use in a linear axis drive in one variation of the tool carriage.

In some variations, the reference conductive plate 790 may be smaller than the first conductive plate 730 and/or the second conductive plate 740, which may, for example, permit clearance for the electronics 750 when the first conductive plate 730, the second conductive plate 740, and the reference conductive plate 790 are stacked upon one another in the housing, thereby reducing the need to increase height of the load cell to accommodate the reference conductive plate 790. For example, in some variations in which the first and/or second conductive plates are generally circular in shape, the reference conductive plate 790 may be generally in the shape of a segment of a circle (e.g., generally semi-circular, or any suitable portion of a circle) or an annular segment (as shown in FIG. 7J). Furthermore, the reference conductive plate 790 may have a shape configured to provide an axial passage through a central region (e.g., a clearance cutout 792) that is configured to be aligned with openings 732 and 742 in the first and second conductive plates, respectively. The conductive plates may be sensitive to gap size variations between the first and second conductive plates. Accordingly, the load cell may enable detection of axial loads based on change in capacitance resulting from the gap size variations. For example, if an external force acts axially to deform the housing proportional to the external force, or to cause the central region 712 to move relative to the outer region 714 of the housing (e.g., axial loads on the ball screw 780 which cause the central region 712 to flex relative to the outer region 714), then the axial displacement of the first and second conductive plates, or reduction/expansion of gap distance, is measureable by detecting the resulting change in capacitance from the first and second conductive plates. Thus, the space-efficient conductive components within the hollow housing 710 enable the load cell 700 to be compact and suitable for tight or limited spaces in which axial load measurement may be desired. For example, in some variations, the housing is between 10 mm and 15 mm in diameter (e.g., 12 mm in diameter) and between 2 mm and 5 mm tall (e.g., 3.5 mm), though the housing may include any suitable dimensions.

As shown in FIG. 7F, the compact load cell 700 may be integrated into a linear axis tool drive shown in FIG. 5A, distal to the ball nut guide 760 in a low-space environment. For example, the load cell may be disposed on the ball screw between the ball nut guide and the distal end of the threaded shaft (e.g., the pusher element), such that a first conductive plate is referenced (e.g., fixed) relative to the ball nut guide and a second conductive plate is referenced (e.g., fixed) relative to the threaded shaft.

Figure 7K:
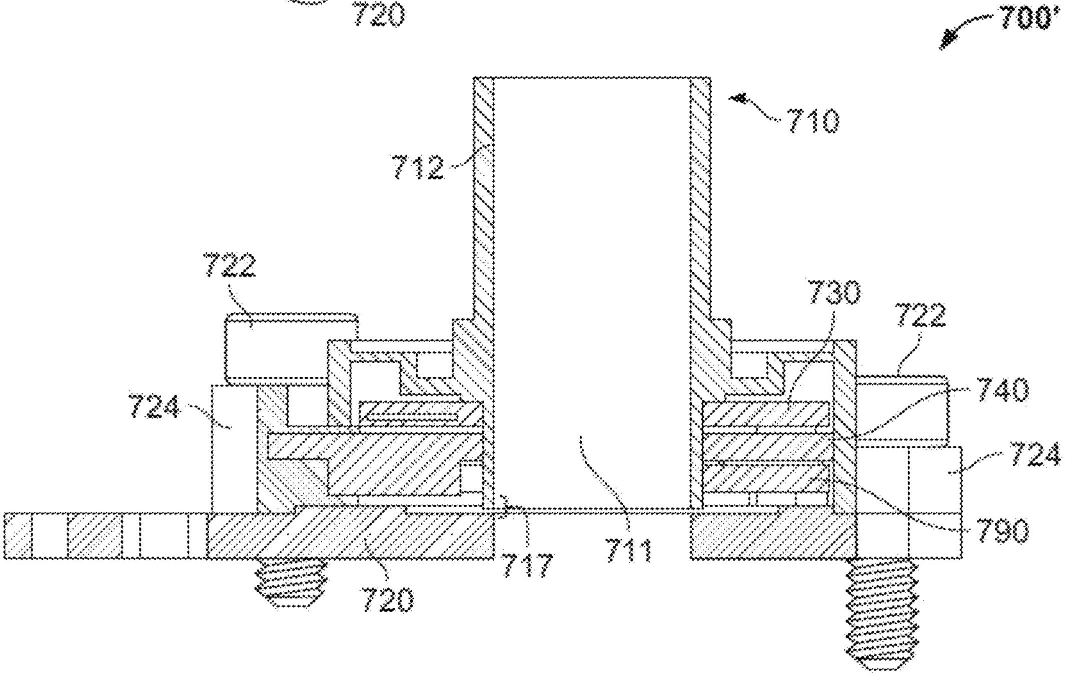

For example, as shown in FIGS. 7J and 7K, the housing 710 may include at least one housing extension 724 extending radially outward from the outer region 714 of the housing, and the conductive plates (e.g., first conductive plate 730, second conductive plate 740, and reference conductive plate 790) of the housing 710 may be enclosed in the recess of the housing by a base plate 720. The base plate 720 and housing 710 may be mounted to the ball screw nut guide 760 with fasteners (e.g., screws) 722 securing the housing extensions 724 and the base plate 720 to mating features on the ball screw nut guide 760. Accordingly, axial loads on the ball screw 770 (e.g., via pusher 770) cause deflection between the central region 712 and outer region 714 in the housing of the compact load cell 700, and therefore further causes a corresponding detectable change in capacitance between the first conductive plate 730 (coupled to the central region 712) and the second conductive plate 740 (coupled to the outer region 714). As pictured in FIG. 7F, the housing 710 may include a plurality of housing extensions 724 distributed generally around a circumferential perimeter of the load cell 700, but in other variations, the housing 710 may include a housing extension 724 in the shape of an annular ring or flange, or any other suitable structure for mounting the housing 710 to the ball nut guide 760.

Additionally, in some variations, the central region 712 of the housing may include a central structure 711. The central structure 711 may include a lumen as shown in FIG. 7K (e.g., to allow passage of a ball screw 780 as shown in FIG. 7C, etc.), but may alternatively be substantially solid (e.g., in variations in which a central passage through the load cell is not needed, such as if the central region 712 includes a ball seat for receiving axial load). As shown in FIG. 7K, the central structure 711 may extend axially through at least most of the recess of the housing through the conductive plates (e.g., 730, 740, and 790 if included). As such, the central structure 711 may help provide an environmental seal for the housing and its conductive plates and other components, such as to protect against dirt, grease, and/or other debris. Furthermore, the central structure 711 prevents an excessive compressive force from overloading the load cell. A clearance gap 717 between the central structure 711 and the base plate 720 generally permits the central region 712 to move axially relative to the outer region 714 of the housing within a predetermined range of motion (correlated to the measurable range of gap distance between the first conductive plate 730 and the second conductive plate 740). As the central region 712 moves axially relative to the outer region 714, the distance of the gap 717 varies. However, physical interference between the central structure 711 and the base plate 720 occurs when the central structure 711 moves toward the base plate 720 until it abuts the base plate 720, such that the central structure 711 prevents an excessive compressive force from overloading and potentially damaging the load cell.

Furthermore, as shown in FIG. 7G, a flex circuit 752 (or ribbon cable, or other suitable wiring) may be configured to communicate with and/or power the electronics 750 shown in FIG. 7E, and may be long enough to accommodate the range of linear movement of the ball nut guide 760 (which may be similar to movement of the ball nut guide 568 described above with respect to FIG. 5A).

Furthermore, the compact load cell may be implemented in other parts of the tool driver. For example, as discussed above, the compact load cell may be used to measure axial loads on the ball screw actuating the carriage on the stage, or in any other portion of the tool driver or other applications in which it is desirable to measure axial loads.

Referring back to FIG. 4B, the tool carriage 400 may include one or more PCBs for mounting various sensors and electronics for the tool carriage. For example, a main PCB 482 may be disposed on one side to include motor drivers, microcontrollers, encoders for the linear axis drives and/or rotary axis drives, current sensors, connectors, etc. The main PCB 482 may be split into two halves, such as a left side corresponding to the left side of the housing and its components and a right side corresponding to the right side of the housing and its components. Alternatively, the main PCB 482 may include a single board (e.g., horseshoe-shaped). Various wiring (e.g., ribbon cables) for motors such as motor **452*a* for linear drive axis 450*a*, may be directed toward the main PCB 480 (e.g., along the direction W shown in FIG. 4**B).

Rotary Axis Drive Carriage Variations

Figure 9A:
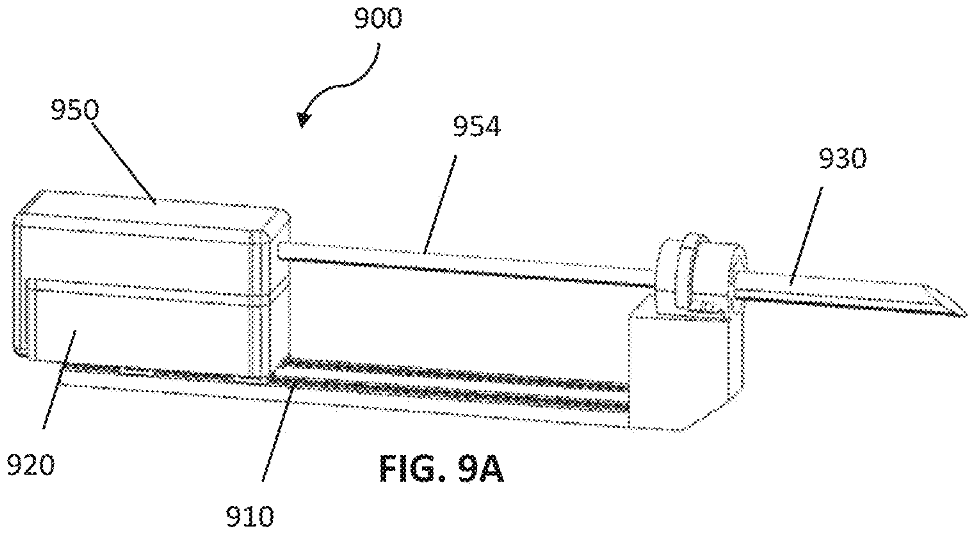
FIG. 9A is a perspective view of another variation of a tool driver.
Figure 9B:
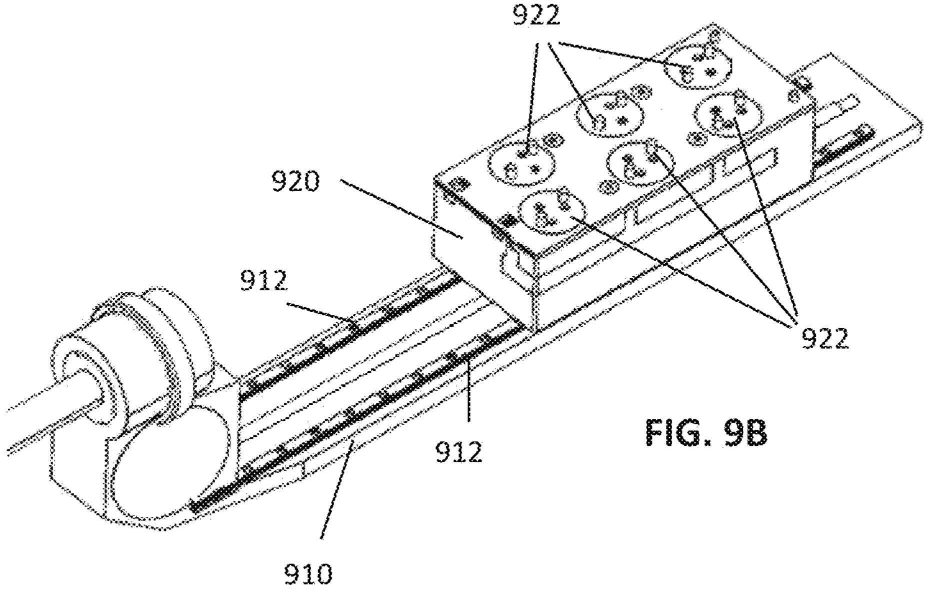
FIG. 9B is a perspective view of a partially disassembled version of the tool driver depicted in FIG. 9A.

In another variation, a tool carriage may include a plurality of rotary axis drives for actuating a set of articulated movements of the end effector and/or rotating a tool shaft around a tool axis. In some variations, as shown in FIGS. 9A and 9B, a tool carriage 920 may be slidingly engaged with a base 910 such as with longitudinal rails 912 (e.g., linear bearings). Additionally, similar to the tool carriage depicted in FIGS. 2A and 2B, the tool carriage 920 may be configured to receive and couple to a tool 950 having a tool shaft 954 and an end effector disposed at the distal end of the tool shaft, where the tool 950 is aligned so as to at least partially pass through a cannula 930 coupled to the base 910. As shown in FIG. 9B, the tool carriage 920 may include a plurality (e.g., six) of rotary axis drives 922 configured to actuate and/or position the end effector of the tool 950 relative to the base 910. In some variations, a sterile adapter or other sterile barrier may be disposed between non-sterile drive axes of the carriage and a sterile surgical tool. Exemplary variations of sterile adapters are described in U.S. Provisional Patent Application No. 62/436,957 filed Dec. 20, 2016, U.S. Provisional Patent Application No. 62/436,965 filed Dec. 20, 2016, U.S. Provisional Patent Application No. 62/436,974 filed Dec. 20, 2016, and U.S. Provisional Patent Application No. 62/436,981 filed Dec. 20, 2016, each of which is incorporated herein in its entirety by this reference.

Rotary Axis Drive Carriage Architectures

Figure 10A:
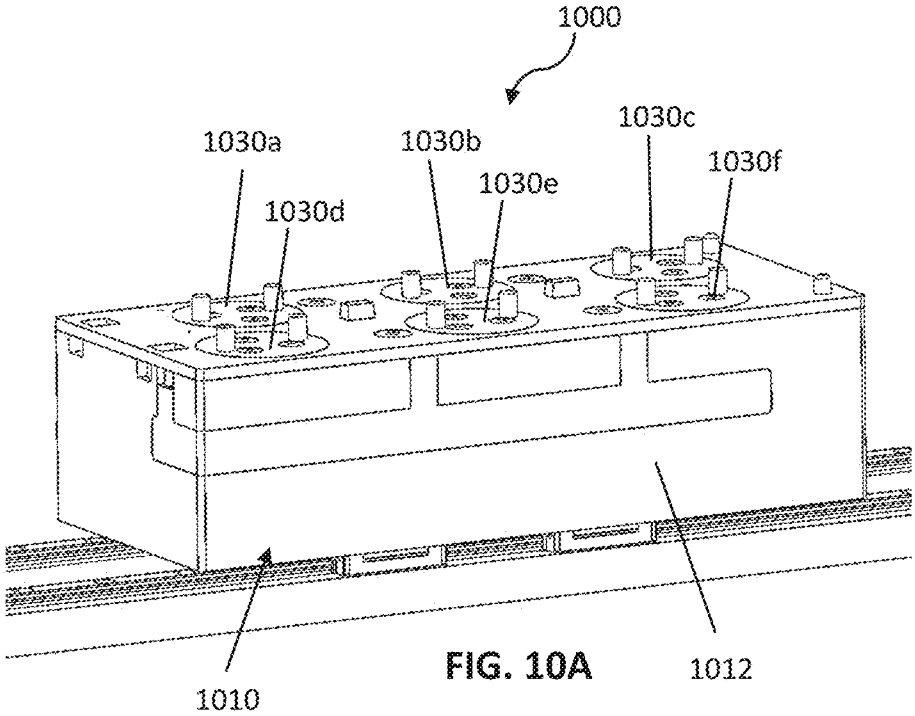
FIGS. 10A and 10B are perspective views of another variation of a tool carriage having a plurality of rotary axis drives.
Figure 10B:
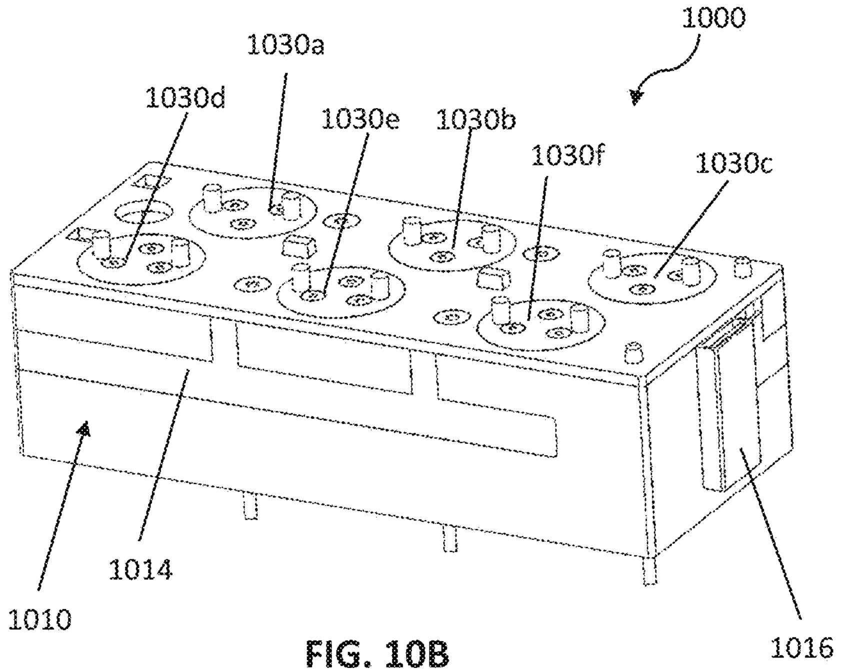

In one variation as shown in FIGS. 10A and 10B, a tool carriage 1000 may include six rotary axis drives arranged in two rows (extending longitudinally along the base) that are slightly staggered (e.g., to reduce width of the carriage and increase the compact nature of the tool driver). For example, as more clearly shown in FIG. 10B, rotary axis drives 1030*a*, 1030*b*, and 1030*c* may be generally arranged in a first row, while rotary axis drives 1030*d*, 1030*e*, and 1030*f* may be generally arranged in a second row that is slightly longitudinally offset from the first row. As another example, as shown in FIG. 34, a tool carriage 3400 may include rotary axis drives arranged in an unstaggered rectangular array (e.g., six rotary axis drives arranged in a 2×3 rectangular array, or any suitable number of axis drives arranged in a rectangular array).

Figure 10C:
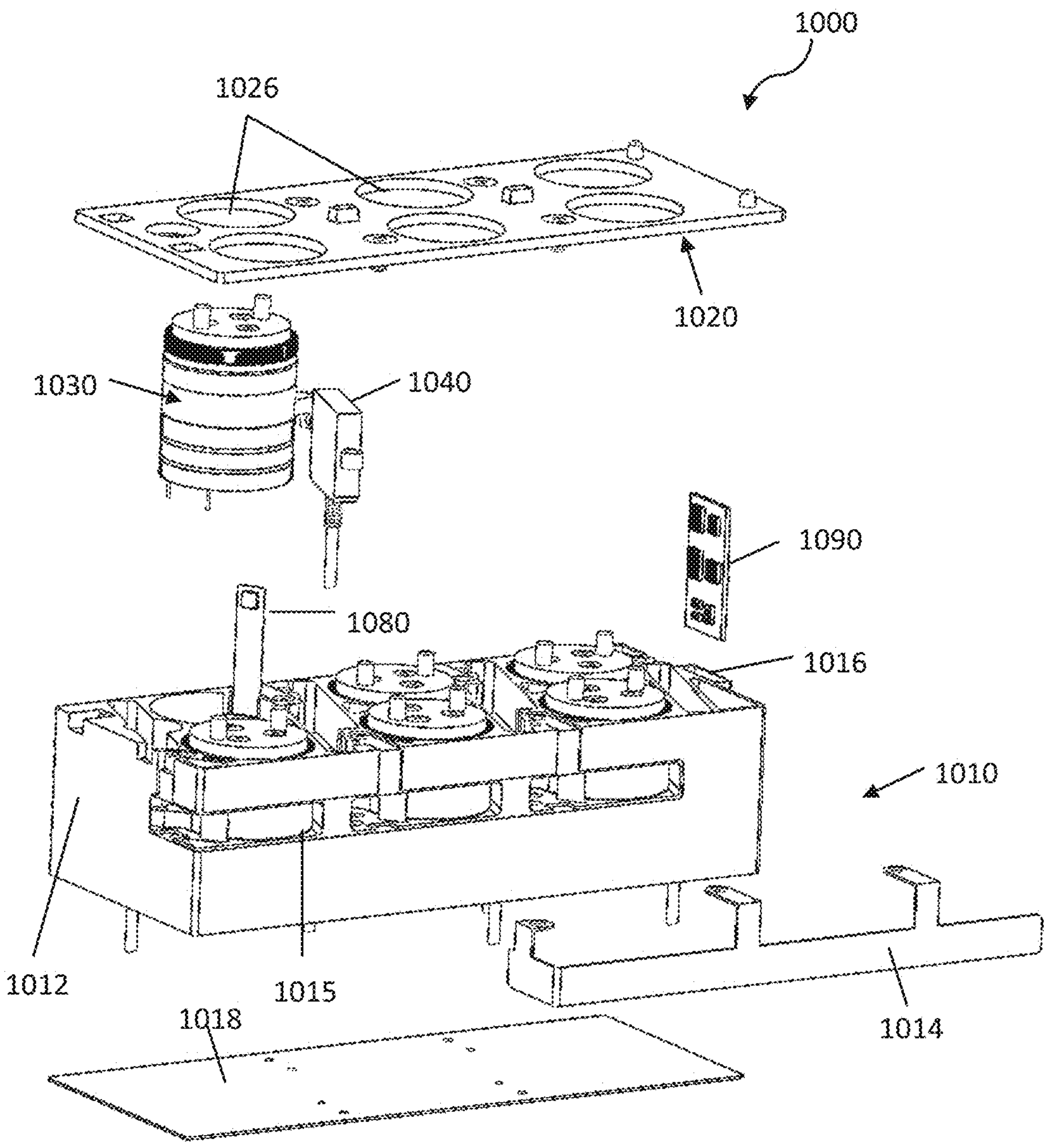
FIG. 10C is a partially exploded view of the tool carriage depicted in FIGS. 10A and 10B.

As shown in FIG. 10C, the tool carriage 1000 includes a housing 1010 that substantially encloses the rotary axis drives and other tool carriage components such as one or more load cells 1040, one or more rotary axis drive output encoders 1080, wiring, and/or other suitable components. For example, the housing 1010 may include a housing body 1012 defining an internal space configured to receive the rotary axis drives and other components, a bottom housing plate 1018 that couples to the housing body 1012 to substantially seal off a lower portion of the internal space, and a top housing plate 1020 that couples to the housing body 1012 to substantially seal off an upper portion of the internal space. The bottom housing plate 1018 and top housing plate 1020 may couple to the housing body 1012 with fasteners such as screws, or may be attached in any suitable manner (e.g., interlocking features, epoxy, welding, etc.). In other variations, one or both of the bottom housing plate 1018 and top housing plate 1020 may be omitted, or may be incorporated with the housing body 1012 as an integrated unitary piece. The housing 1010 may be made of a suitably rigid metal (e.g., aluminum, steel) or plastic, and may be machined, casted, molded, or made in any suitable combination of manners.

Figure 10D:
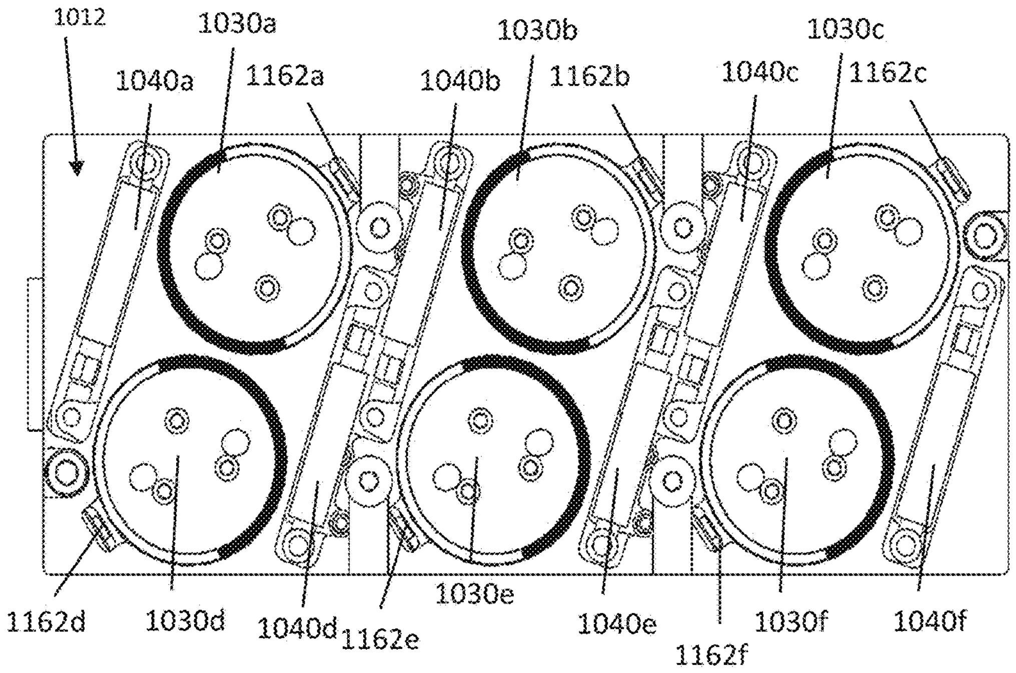
FIG. 10D is a top view of the tool carriage depicted in FIGS. 10A and 10B without a top housing plate.
Figure 10E:
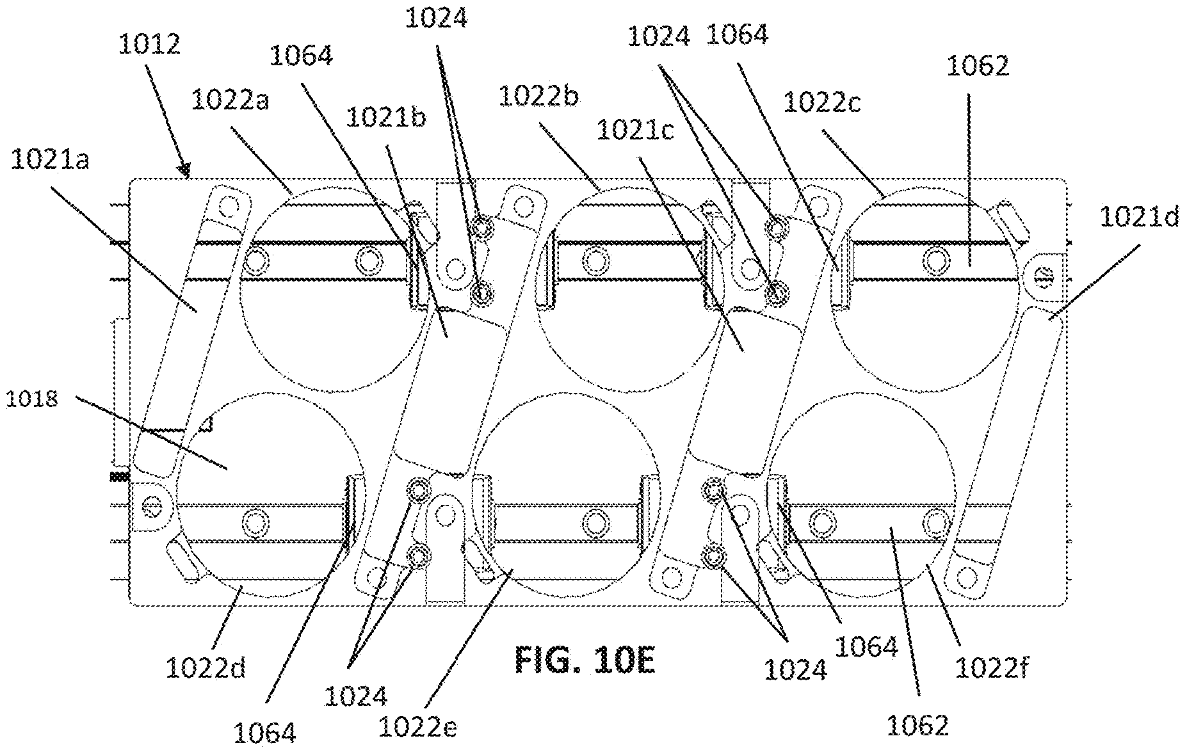
FIG. 10E is a top view of a housing body mounted to a base of a tool driver.

As shown in FIGS. 10D and 10E, the housing body 1012 may include openings configured to frame and otherwise provide structural support for the rotary axis drives and/or other components. For example, the housing body 1012 may include an opening 1022*a* configured to receive and support rotary axis drive 1030*a*. Similarly, the housing body 1012 may further include additional openings 1022*b*, 1022*c*, 1022*d*, 1022*e*, and 1022*f* configured to receive and support rotary axis drives 1030*b*, 1030*c*, 1030*d*, 1030*e*, and 1030*f*, respectively. In some variations, the housing body 1012 may include a structural framework with one or more openings configured to provide structural support for one or more load cells. For example, the housing body 1012 may include an opening 1021*a* configured to receive and support a load cell 1040*a*. Similarly, the housing body 1012 may further include additional openings 1021*b* configured to receive and support adjacent and staggered load cells 1040*b* and 1040*d*, opening 1021*c* configured to receive and support adjacent and staggered load cells 1040*c* and 1040*e*, and/or opening 1021*d* configured to receive and support load cell 1040*f*. In other variations, there may be a 1:1 correspondence between openings (1021*a-d*, etc.) and load cells such that each opening receives and support only one load cell (e.g., the housing body 1012 may include six separate openings for receiving and supporting six load cells). The various openings may be circular (e.g., for supporting rotary axis drives with a generally circular cross-section), rectangular (e.g., for supporting load cells with a generally rectangular cross-section), or any suitable shape such as square, elliptical, etc. Furthermore, the openings may be any suitable arrangement corresponding to the desired (preferably compact) arrangement of rotary axis drives and other components. Although the housing body 1012 is depicted with openings corresponding to six rotary axis drives and six load cells, it should be understood that the housing body 1012 may include any suitable number of openings depending on the number of internal components of the tool carriage. Furthermore, the housing body 1012 (or other suitable portions of the housing) may include one or more cutouts to help reduce the overall weight of the tool carriage.

Figure 10F:
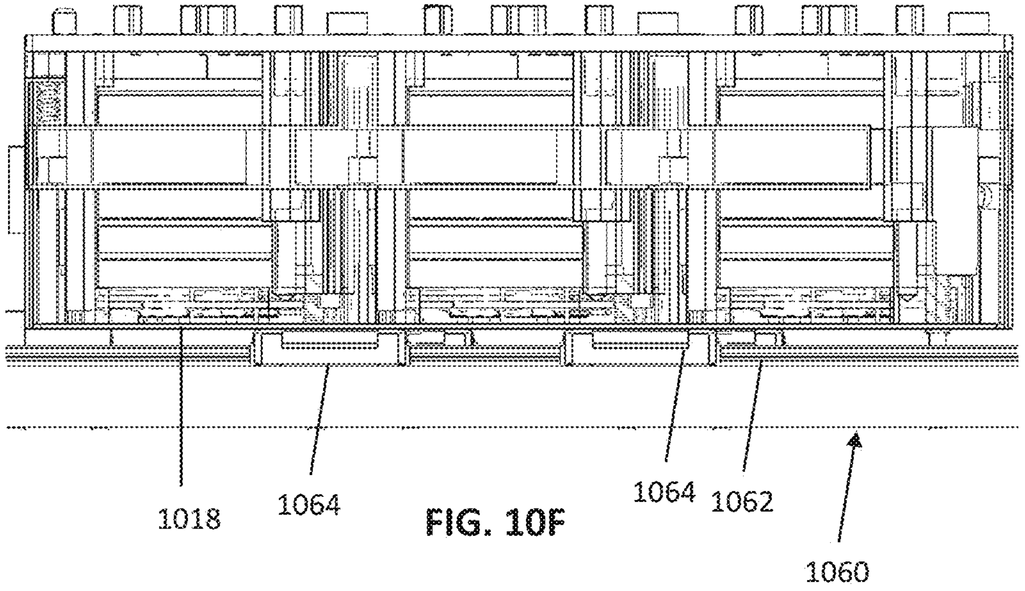
FIGS. 10F and 10G are a side translucent view and a front translucent view, respectively, of the tool carriage depicted in FIGS. 10A and 10B mounted to a base of a tool driver.
Figure 10G:
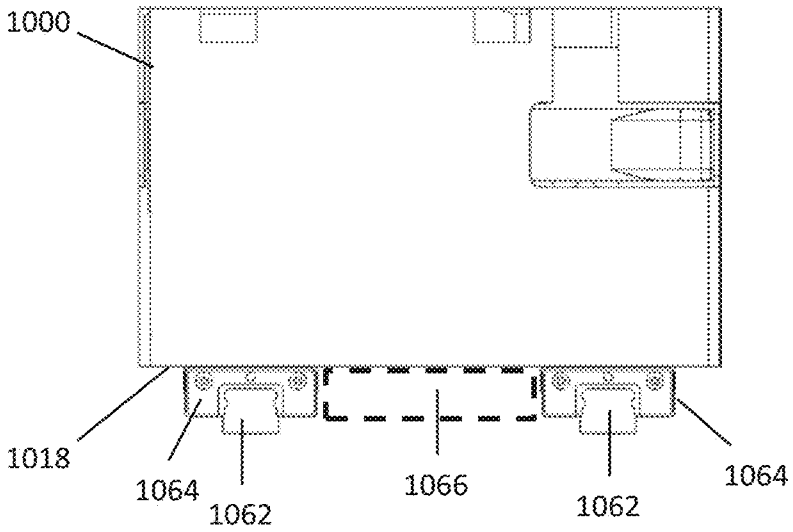

As shown in FIG. 10E, the housing body 1012 may further include one or more mounting holes 1024 that facilitate mounting of the tool carriage to the base 1060 of the tool driver. For example, one or more mounting holes 1024 may be a clearance hole that enables passage of a threaded fastener (e.g., screw, bolt, etc.) configured to engage a threaded hole in a carrier 1064 slidingly engaged with a linear bearing 1062. In other example, one or more carriers 1064 may include a clearance hole that enables passage of a threaded fastener configured to engage a mounting hole 1024 which may be a blind threaded hole. Alternatively, the tool carriage may mount to the base in any suitable manner. In one exemplary variation, the housing body 1012 may include eight mounting holes 1024, where two mounting holes 1024 correspond to each of four carriers 1064. Two carriers 1064 may be slidingly engaged with a left side linear bearing (e.g., a proximal carrier and a distal carrier, as shown in the side view of FIG. 10F) and two carriers 1064 may be slidingly engaged with a right side linear bearing. As shown in FIG. 10F, the bottom plate 1018 may be disposed between the bottom of the housing body 1012 and the top of the linear bearings, in order to substantially seal off the lower portion of the housing body 1012. Accordingly, the bottom plate 1018 may have clearance holes corresponding to the mounting holes 1024 of the housing body 1012 so as to be mounted to the base 1060 with the same fasteners used to mount the housing body 1012 to the base 1060. The bottom plate 1018 may be a thin plate (e.g., under 1 mm, or 0.5 mm). In some variations, as shown in FIG. 10G, this mounting configuration may facilitate a clearance space 1066 located between the linear bearings 1062 and under the tool carriage 1000. The clearance space 1066 may, for example, permit passage of other components (e.g., ribbon cables or flex cables for electronic components) outside of the tool carriage or in a separate housing compartment underneath the tool carriage 1000. Alternatively, the bottom plate 1018 may include a channel along its midline that drops into the clearance space 1066 for providing additional internal volume to the bottom of the tool carriage 1000.

As shown in FIG. 10C, the top of the housing 1010 (e.g., in top housing plate 1020) may define a plurality of openings 1026 shaped and aligned with the output of the rotary axis drives 1300 such that the output of the rotary axis drives may engage with a tool or sterile barrier between the tool driver and the tool. For example, the openings 1026 may be generally circular and correspond with the openings 1022 in the housing body that support the rotary axis drives.

Furthermore, in some variations, the housing 1010 may include features that accommodate assembly of one or more rotary axis drives 1300 in the housing. For example, as shown in FIG. 10C, the housing body 1012 may include a lateral slot 1015 that enables lateral insertion of one or more components of a rotary axis drive being assembled (as further described below with respect to FIGS. 15A and 15B).

Figure 18A:
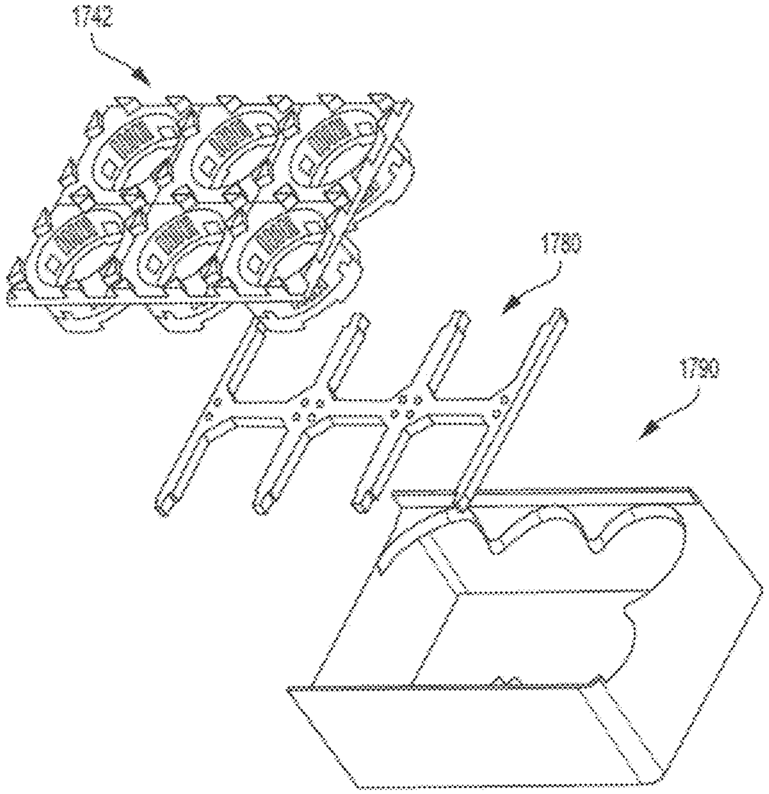
FIG. 18A is an exploded view of a partial assembly of one variation of a tool carriage configured to include multiple instances of the rotary axis drive depicted in FIGS. 17A and 17B.
Figure 18B:
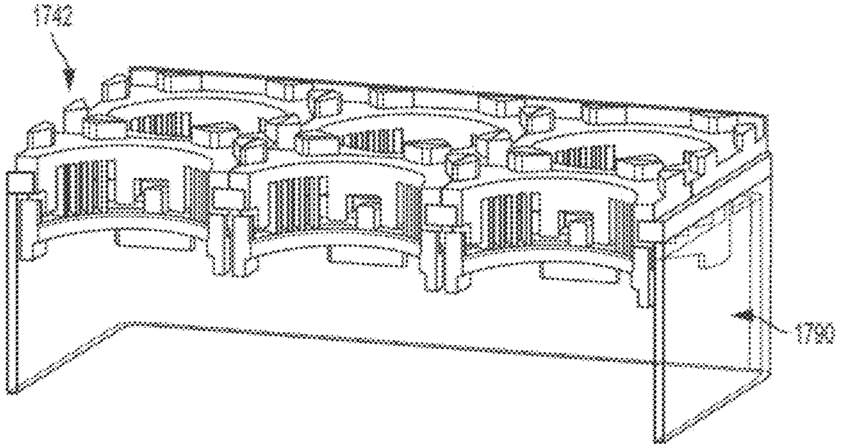
FIG. 18B is a cutaway perspective view of the partial assembly depicted in FIG. 18A.

In another variation, as shown in FIGS. 18A and 18B, multiple rotary axis drives 1700 may be mounted in a tool carriage housing 1790, supported by an internal chassis 1780. For example, the internal structure 1780 may be mounted into an internal volume of the tool carriage housing 1790 via fasteners (e.g., screws) or other suitable mechanism. The internal chassis 1780 may be formed of a suitable rigid material (e.g., aluminum) and include multiple compartments configured to receive individual torque sensor assemblies, shown in part by the multiple frames 1742 mountable in the internal chassis 1780. The frames 1742 may be coupled to the internal chassis 1780, such as with fasteners applied to the low stress points of the frames 1742. Other components of the torque sensor assemblies 1740 and the rest of the rotary axis drives 1700 may further be assembled into the housing 1790. Overall, the housing 1790 may generally reinforce the arrayed pack structure of the rotary axis drives 1700. Although the internal chassis 1780 as shown in FIGS. 18A and 18B are conducive to a rectangular array of rotary axis drives, it should be understood that the rotary axis drives may be arranged in a staggered, offset, or other suitable configuration.

Figure 38A:
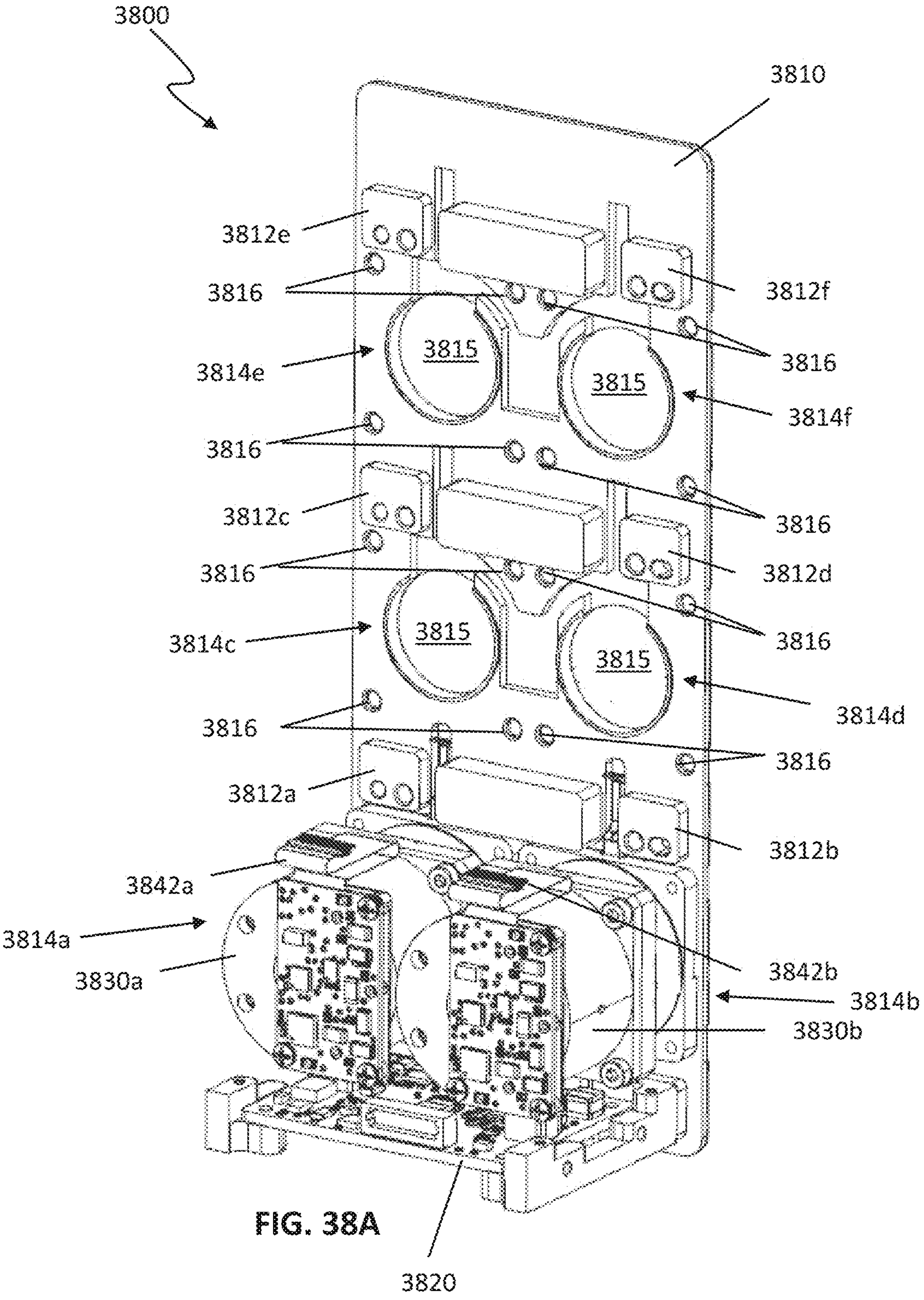
FIGS. 38A-38E are schematic illustrations of various assembly states of a modular, scalable variation of a tool driver.

In another variation as shown in FIGS. 38A-38E, a tool carriage 3800 in a tool driver may include a plurality of rotary axis drives that are configured to actuate one or more articulated movements of a surgical tool, where the rotary axis drives are arranged in a modular, scalable array. For example, as shown in FIG. 38A, the tool carriage 3800 may include a carriage base 3410, which includes designated regions which may receive various modules for placement in the carriage. For example, the carriage base 3410 may include one or more drive module sites 3814*a*-3814*f* for receiving rotary axis drive modules and/or one or more circuit board module sites 3812*a*-3812*f* for receiving circuit board modules. Generally, the number of modules placed into the carriage base may vary, depending on, for example, how many degrees of freedom are desired to be actuatable by the tool driver (e.g., one degree of freedom, two degrees of freedom, three degrees of freedom, etc.). Some of the designated regions for receiving modules may remain unused, such as if the number of drive module sites exceeds the number of rotary axis drive modules required for a particular tool driver. Alternatively, a carriage base 3410 may be easily manufactured with fewer or more designated regions, such as if fewer or more rotary axis drive modules (and/or circuit board modules) are desired. For example, as shown in FIG. 38A, the drive module sites and the circuit board module sites are arranged in a rectangular array as regular, repeating rows. In different variations of tool drivers for actuating tools of different numbers of degrees of freedom, the carriage base 3810 may be shorter (with fewer rows of sites) or longer (with more rows of sites). Accordingly, the rotary axis drives in a tool driver 3800 may be arranged in a modular manner that is more easily scalable depending on the number of desired degrees of freedom of a surgical tool that will be actuated by the tool driver. Additionally, modularity of the rotary axis drives and the circuit boards in the tool driver helps facilitate more streamlined manufacturing and/or repair of the tool driver (e.g., fewer different kinds of parts, simpler swapping of individual modules that may be malfunctioning, etc.).

As shown in FIG. 38A, a drive module site (e.g., any of 3814*a*-3814*f*) may include an output hole 3815 and one or more mounting holes 3816. The output hole 3815 may receive and permit passage of a distal end of a rotary axis drive module such that the output of the rotary axis drive module may be coupled to a surgical tool. For example, a rotary output shaft of the rotary axis drive module may extend through the output hole 3815. The one or more mounting holes 3816 may enable coupling of the rotary axis drive module to the carriage base, such as with fasteners. Although each drive module site is shown in FIG. 38A as including four mounting holes that are equally distributed at corners of the drive module site, it should be understood that a drive module site may include any suitable number of mounting holes arranged in any suitable pattern (e.g., depending on the footprint shape of the rotary axis drive module). Generally, a distal portion (e.g., near the rotary output shaft) of the rotary axis drive may be coupled to the carriage base 3810 via the mounting holes 3816 at its respective drive module site. Accordingly, in some variations, the rotary axis drive may be mounted to the tool carriage only at a distal portion of the rotary axis drive and may otherwise be free-standing (e.g., without a surrounding lattice or frame to support the main body of the rotary axis drive). In these variations, the single-end mounting of the rotary axis drives may furthermore enable the rotary axis drives to be more easily replaced or swapped (e.g., for maintenance or repair). Additionally, the absence of additional supporting framework parts may reduce the number of parts that must be modified for scaling the tool driver to include fewer or more rotary axis drives, thereby further contributing to the scalability of the tool driver.

Figure 38B:
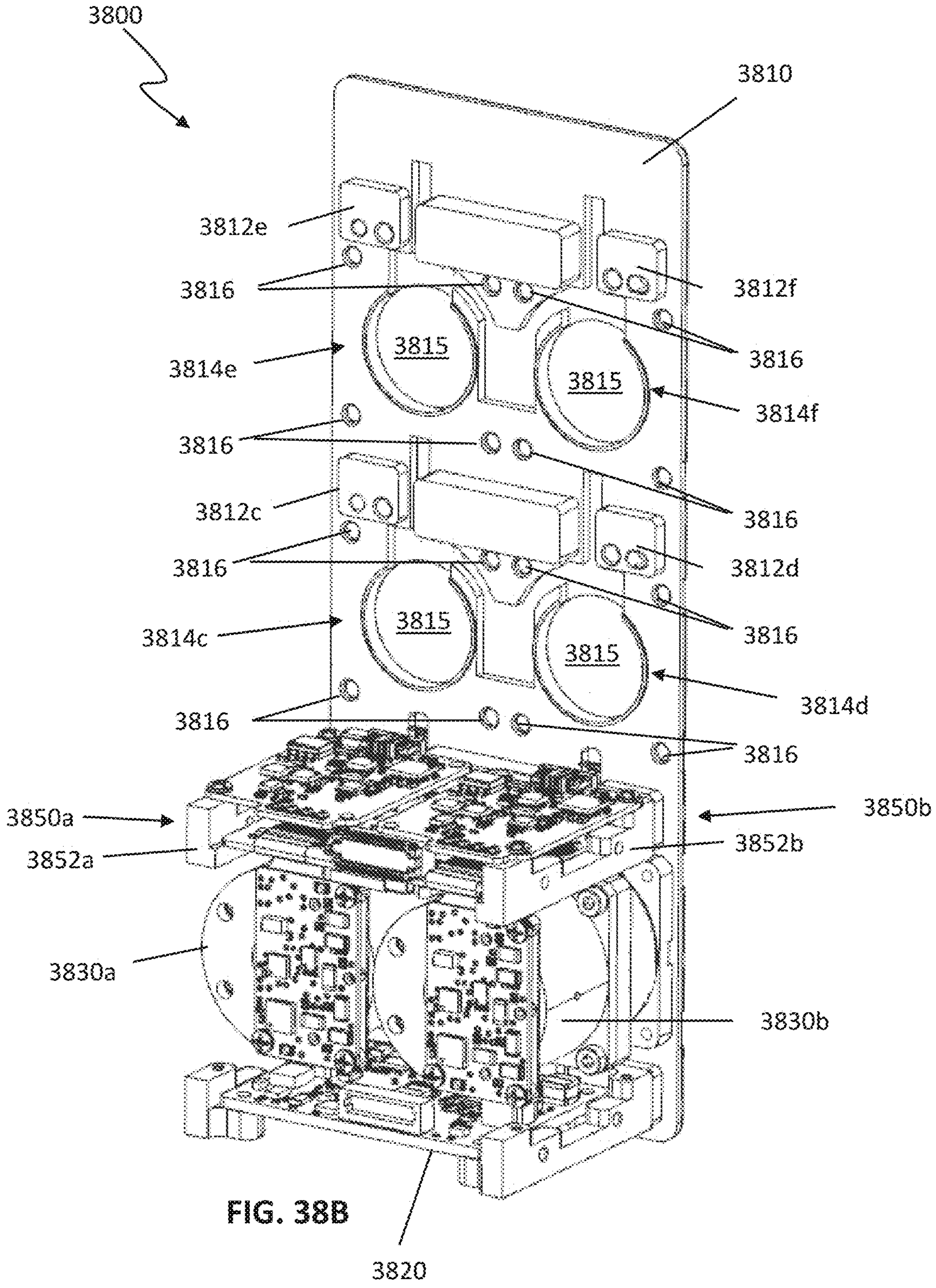

As shown in FIG. 38A, a circuit board module site (e.g., any of 3812*a*-3812*f*) may include an interface for coupling to a circuit board module. For example, as shown in FIG. 38B, a circuit board module 3850*a* may include a circuit board support 3852*a* and one or more circuit boards coupled to the circuit board support 3852*a*. The circuit boards may include, for example, motor driver electronics, sensor electronics, memory, and/or any suitable electronic components that may be associated with a rotary axis drive module. The circuit board support 3852*a* (pictured in FIG. 38B) may couple to its own respective circuit board module site 3812*a* (pictured in FIG. 38A) via fasteners or any suitable mechanism. Additionally or alternatively, one or more circuit boards may couple directly to a circuit board module site via pin connectors or the like. In some variations, each circuit board module (e.g., 3850*a* and 3850*b*) may be associated with a respective rotary axis drive module (e.g., 3830*a* and 3830*b*), and each circuit board module may be coupled to the carriage base 3810 adjacent to or near their respective rotary axis drive modules.

The drive module sites and the circuit board module sites may be arranged on the carriage base in a regular, repeating pattern. For example, as shown in FIG. 38A, generally each circuit board module may be associated with a respective rotary axis drive module (e.g., six circuit board module sites 3812*a*-3812*f* and six drive module sites 3814*a*-3814*f*), and rows of drive module sites may alternate with rows of circuit board module sites. Accordingly, the rotary axis drive modules 3830*a*-3830*f* may alternate with the circuit board modules 3850*a*-3850*f* in a regular, repeating pattern.

Further details of the modularity and assembly of an exemplary variation of a tool carriage 3800 with six rotary axis drive modules is shown in FIGS. 38A-38E. As shown in FIG. 38A, two rotary axis drive modules 3830*a* and 3830*b* may be mounted to their respective drive module sites on the carriage base 3810, in the manner described above. The rotary axis drive modules 3830*a* and 3830*b* form a first row of rotary axis drive modules. The rotary axis drive modules 3830*a* and 3830*b* may have respective cables (e.g., ribbon cables) 3842*a* and 3842*b* that carry signals to and from the rotary axis drive modules, such as for control of a motor, receiving torque sensor signals, etc. The cables 3842*a* and 3842*b* may include sufficient extra length to provide strain relief for any movement of the rotary axis drive modules relative to the carriage base, such as torqueing. For example, in some variations, the cables 3842*a* and 3842*b* may include a portion that is doubled up along at least a portion of the length of the rotary axis drive modules 3830*a* and 3830*b*. Additionally, a carriage PCB 3420 may be mounted to the carriage base 3810 in a manner similar to that described above for the circuit board modules. For example, the carriage PCB 3420 may be coupled to its own circuit board support, and the circuit board support may be coupled to the carriage base 3810 via fasteners or the like. The carriage PCB 3420 may, for example, include electronics for the overall tool driver, such as relating to power, wireless communication, etc.

As shown in FIG. 38B, two circuit board modules 3850*a* and 3850*b* may be coupled to the carriage board by connecting the circuit board supports 3852*a* and 3852*b* to their respective circuit board module sites 3812*a* and 3812*b* (shown in FIG. 38A). The circuit board modules 3850*a* and 3850*b* form a first row of circuit board modules adjacent the first row of rotary axis drive modules. Additionally, the cables 3842*a* and 3842*b* from the rotary axis drive modules 3830*a* and 3830*b* may be connected to the circuit board modules 3850*a* and 3850*b*. In some variations, a single circuit board module may be associated with more than one rotary axis drive module. For example, a single, larger circuit board module with electronics associated with the rotary axis drive modules 3830*a* and 3830*b* may mounted to the carriage base 3810 in place of two separate circuit board modules 3850*a* and 3850*b*.

Figure 38C:
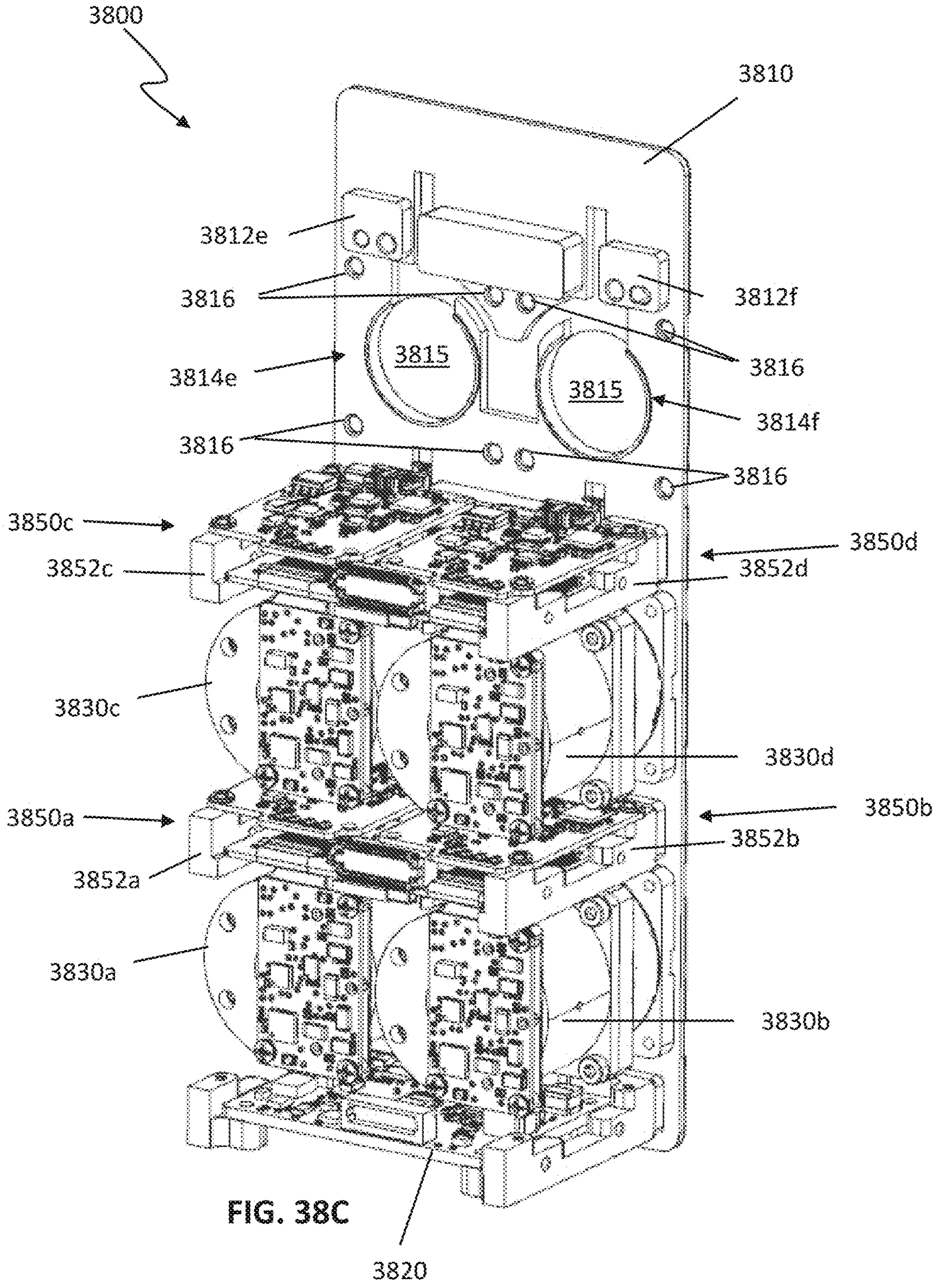

As shown in FIG. 38C, two additional rotary axis drive modules 3830*c* and 3830*d* may be coupled to the carriage base 3810 at the drive module sites 3814*c* and 3814*d*. The rotary axis drive modules 3830*c* and 3830*d* form a second row of rotary axis drive modules adjacent the first row of circuit board modules 3850*a* and 3850*b*. Additionally, two additional circuit board modules 3850*c* and 3850*d* may be coupled to the carriage board by connecting the circuit board supports 3852*c* and 3852*d* to their respective circuit board module sites 3812*c* and 3812*d* (shown in FIG. 38A). The circuit board modules 3850*c* and 3850*d* form a second row of circuit board modules adjacent the second row of rotary axis drive modules 3830*c* and 3830*d*. Electronics in the second row of circuit board modules may be associated with the second row of rotary axis drive modules.

Figure 38D:
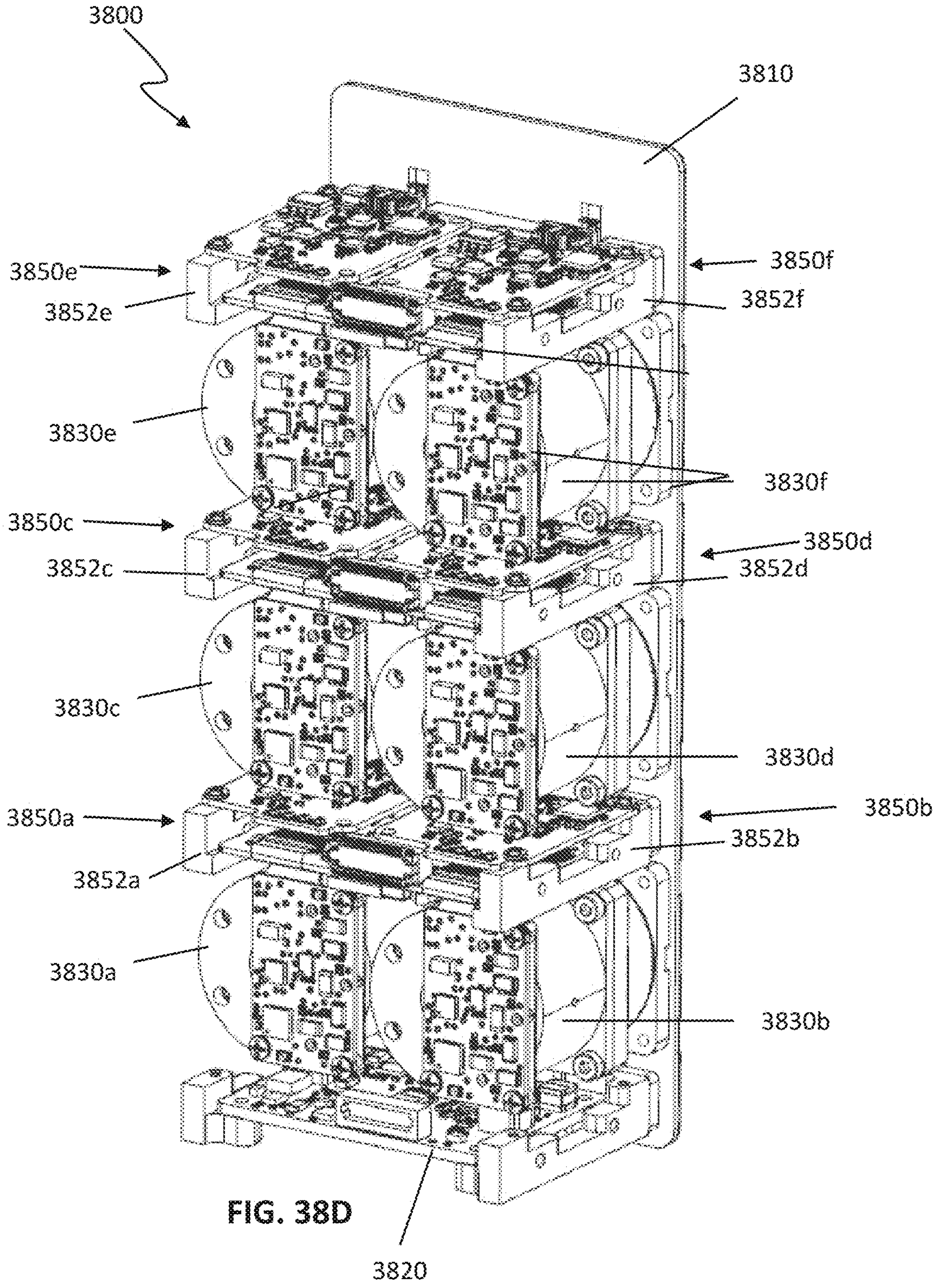

Similarly, as shown in FIG. 38D, two additional rotary axis drive modules 3830*e* and 3830*e* may form a third row of rotary axis drive modules adjacent the second row of circuit board modules 3850*c* and 3850*d*. Additionally, two additional circuit board modules 3850*e* and 3850*f* may form a third row of circuit board modules adjacent the third row of rotary axis drive modules 3830*e* and 3830*f*. Electronics in the third row of circuit board modules may be associated with the third row of rotary axis drive modules. Thus, as shown in FIGS. 38A-38D, the rotary drive modules may be arranged in one variation of a regular and repeating pattern.

Figure 38E:
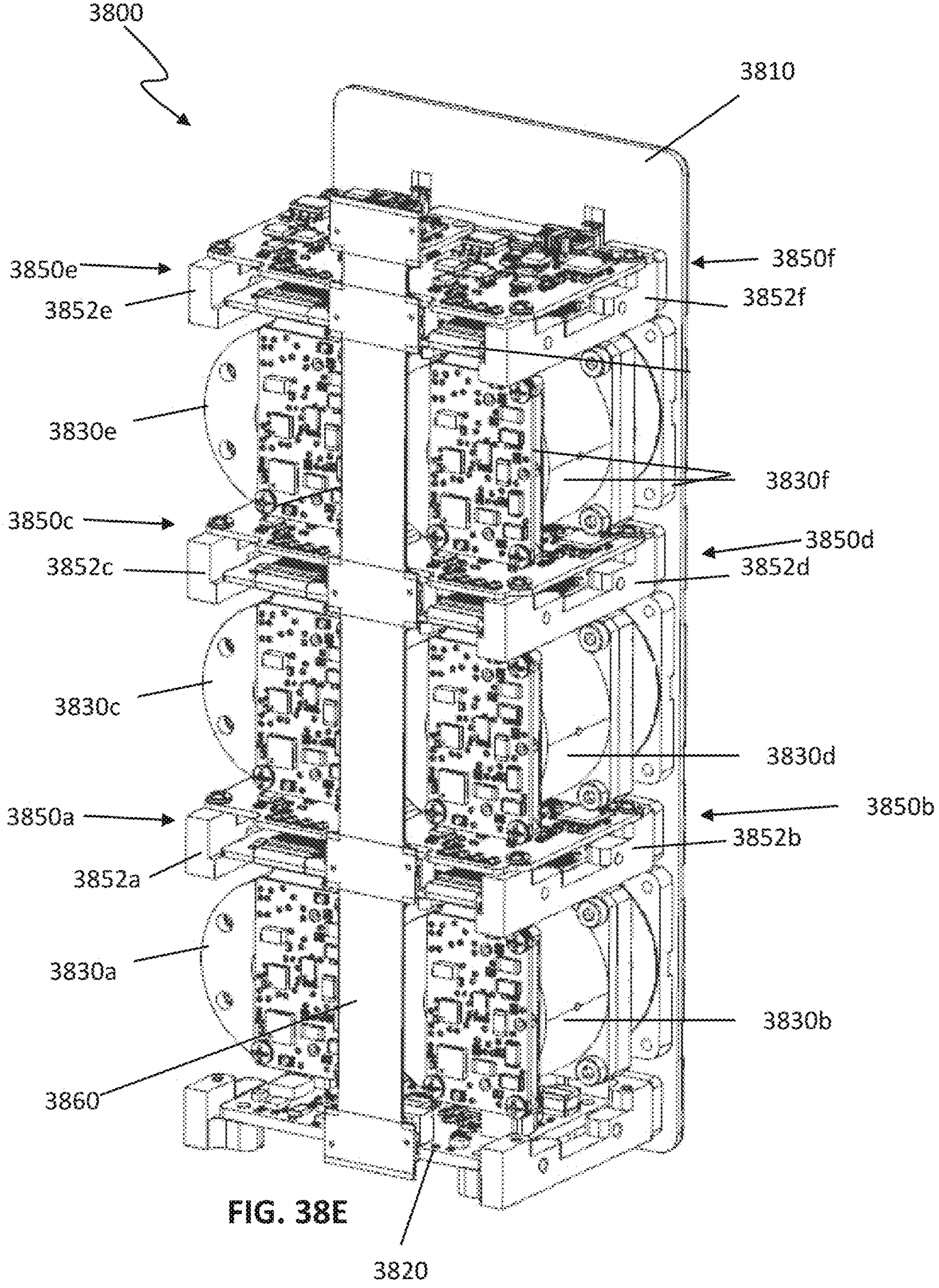

As shown in FIG. 38E, after six rotary drive modules 3830*a*-3830*f* and six circuit board modules 3850*a*-3850*f* are coupled to the carriage base 3810, all or a portion of the circuit board modules may be interconnected. For example, a cable 3860 (e.g., ribbon cable) may interconnect the circuit board modules 3850*a*-3850*f*. The cable 3860 may, for example, include a series of connectors arranged along its length, located at distances along the cable 3860 corresponding to the distances between corresponding connectors on the circuit board modules 3850*a*-3850*f*. The connectors on the cable 3860 may mate with the connectors on the circuit board modules 3850*a*-3850*f*, thereby enabling communication with all of the circuit board modules. Furthermore, the cable 3860 may include a connector configured to mate with a connector on the carriage PCB 3820. Although the cable 3860 is pictured as being disposed along a centerline of the tool carriage 3800, it should be understood that the cable 3860 may be arranged in any suitable manner.

In another variation as shown in FIG. 34, a tool carriage 3400 in a tool driver may include a plurality of rotary axis drives that are configured to actuate one or more articulated movements of a surgical tool, where the rotary axis drives are arranged in a modular scalable array, substantially similar to that described above with reference to FIGS. 38A-38E, except as described below. For example, rotary axis drive modules 3430*a*-3430*f* and circuit board modules 3450*a*-3450*f* may be coupled to a carriage base 3410 in a regular and repeating pattern (e.g., an alternating manner). Each rotary axis drive module 3430*a*-3430*f* may be similar to that described below with reference to FIGS. 37A and 37B. For example, each rotary axis drive module may include a motor (e.g., 3432*b*, 3432*d*, 3432*f* as shown) having a motor shaft, a gear transmission, and a torque sensor (e.g., 3436*b*, 3436*d*, 3436*f* as shown). Each rotary axis drive module may be coupled to the carriage base 3410 by mounting a distal portion of the rotary axis drive module (relative to the motor) to the carriage base 3410 via fasteners or other suitable mechanism. For example, a torque sensor (or a mount coupled thereto) of each rotary axis drive module may be coupled to the carriage base. Accordingly, each rotary axis drive module may be supported on the carriage substantially only by its distal portion being mounted to the carriage base 3410.

Figure 35:
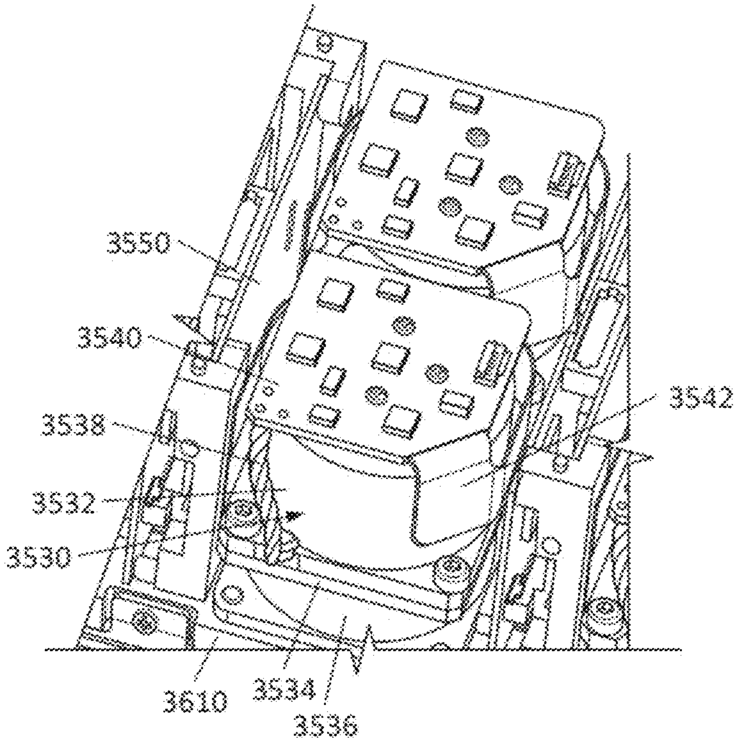
FIG. 35 is a detailed perspective view of part of the tool driver depicted in FIG. 34.
Figure 36:
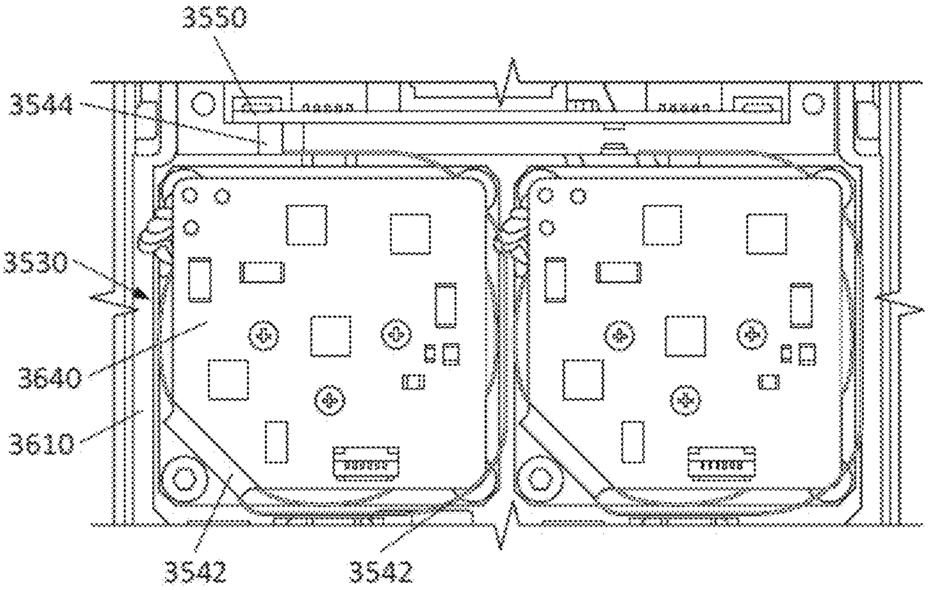
FIG. 36 is a detailed top view of part of the tool driver depicted in FIG. 34.

As shown in FIGS. 35 and 36, one or more of the rotary axis drive modules in the tool carriage 3400 may include one or more cables 3542 (e.g., ribbon cable, flex cable) including a portion that is wrapped circumferentially at least partially around the rotary axis drive around an axis of rotation of the motor shaft. Such circumferential wrapping may, for example, reduce strain on the cable as the rotary axis drive module rotates around the axis of rotation (e.g., in reaction torque during actuation). In some variations, the circumferentially-wrapped cable may be oriented generally perpendicular to the axis of rotation. In other variations, the circumferentially-wrapped cable may be oriented generally helical around the rotary axis drive module, such that its direction of wrapping has a lateral component that is perpendicular to the axis of rotation, as well as a longitudinal component that is parallel to the axis of rotation.

Furthermore, packaging of the cable 3542 and other aspects of the rotary axis drive module may be designed to keep components within a small envelope or footprint. For example, as shown in FIG. 35, a rotary axis drive module 3530 may include a motor 3532, gear transmission 3534, a torque sensor 3536, and a rotary drive PCB 3640. As shown in FIG. 36, the rotary axis drive module 3530 may generally have a square footprint on the carriage base 3610. The motor 3532 may have a generally cylindrical body that lies within the square footprint (e.g., inscribed within the footprint, or smaller), thereby leaving empty space between the cylindrical body and the square footprint. As shown in FIG. 35, sensor cables 3638 for the torque sensor and/or other components may traverse within this empty space. Additionally, the attachment locations for the circumferentially-wrapped cable 3542 to attach to the rotary drive PCB 3640 and a circuit board module 3550 may be selected to leverage the empty space between the cylindrical motor body and the square footprint. For example, as shown in FIG. 36, a first end of the cable 3542 may be attached to the circuit board module 3550 via a connector 3544 disposed across from a flat side of the module's square footprint. From the connector 3544, the cable 3542 wraps circumferentially around the axis of the motor 3532, until a second end of the cable 3542 may be attached to the rotary drive PCB 3640 at one corner of the module's square footprint. For example, in variations in which the first end of the cable 3542 is located at about the middle of a flat side of the module's square footprint, the cable 3542 may wrap at least about 45 degrees, at least about 135 degrees, at least 225 degrees, or more (e.g., in 90-degree increments) around the rotary axis drive so its second end may be located generally at one corner of the module's square footprint. Other extents of circumferential wrap may be suitable, for example, for a rotary axis drive module having different shapes, in order to reduce overall footprint volume of the rotary axis drive module.

Rotary Axis Drives

Different exemplary variations of rotary axis drives for a tool carriage are described below.

Rotary Axis Drive With Harmonic Drive

Figure 11A:
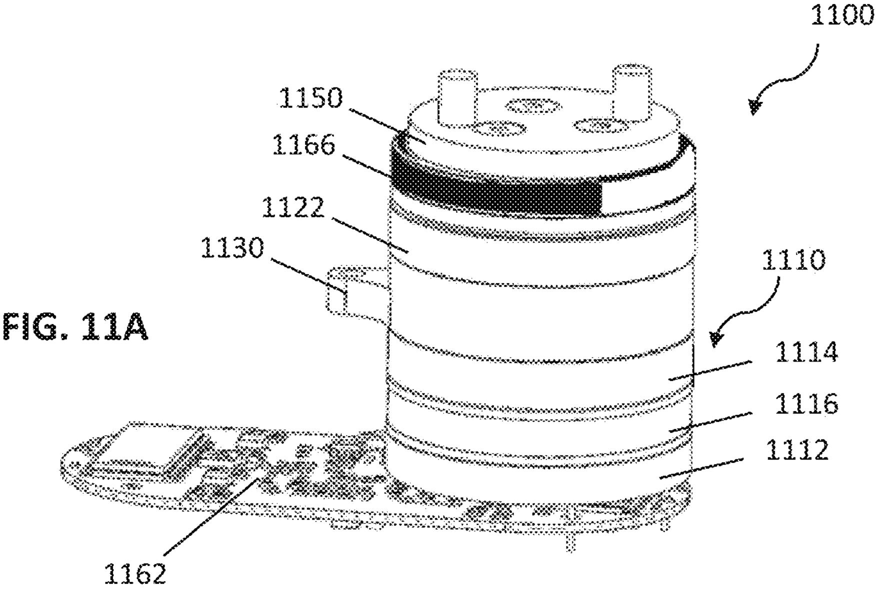
FIG. 11A is a perspective view of one variation of a rotary axis drive in another variation of a tool driver.
Figure 11B:
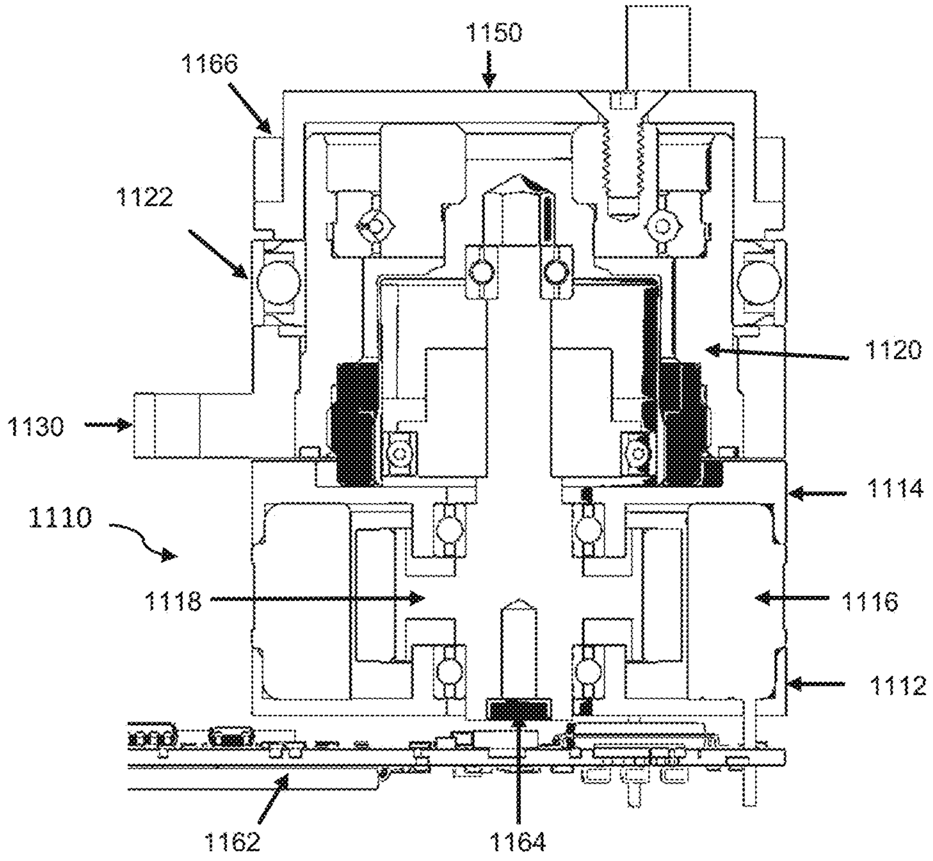
FIG. 11B is a longitudinal cross-sectional view of the rotary axis drive depicted in FIG. 11A.

In one variation of the tool carriage, the tool carriage includes a plurality of rotary axis drives each having a harmonic drive. For example, as shown in FIGS. 11A and 11B, a rotary axis drive 1100 may include a motor assembly 1110, a harmonic drive 1120 coupled to an output of the motor assembly 1110, a load cell connector ring 1130, and a motor coupling disc 1150 configured to couple an output of the rotary axis drive 1100 to a tool and/or sterile adapter to a tool.

The motor assembly 1110 may include a lower motor housing 1112 and an upper motor housing 1114 which house a stator 1116 and a rotor 1118 rotatable relative to the stator 1116. A PCB 1162 may be located adjacent to the motor assembly 1110 and include at least one motor controller, one or more sensors, and/or any suitable electronics associated with the rotary axis drive 1100. An encoder magnet 1164 may be coupled to the rotor 1118 such that one or more encoder sensors may detect the fluctuation of the magnetic field of the encoder magnet 1164 for determining angular or rotational position of the rotor 1118 (and output shaft of the motor assembly 1110). The motor assembly 1110 may be, for example, a servomotor or other suitable kind of actuator. A harmonic drive 1120 may be coupled to an output shaft of the motor assembly 1110 and configured to increase the overall torque output of the rotary axis drive 1100 via strain wave gearing. Advantageously, a drive 1120 may be configured to provide a high gear ratio in a relatively light and compact volume. Furthermore, a radial bearing 1120 may encircle the harmonic drive 1120 and facilitate rotational movement of the harmonic drive 1120 relative to the housing body 1012. In other variations, other suitable gear trains may additionally or alternatively be coupled to the output of the motor assembly. Furthermore, the output of the harmonic drive 1120 or other gear train may be coupled to a motor coupling disc 1150 such that the motor coupling disc 1150 (which is configured to engage with a tool or a sterile adapter to a tool for actuating the end effector of the tool) rotates with the output of the motor assembly 1110.

Figure 11C:
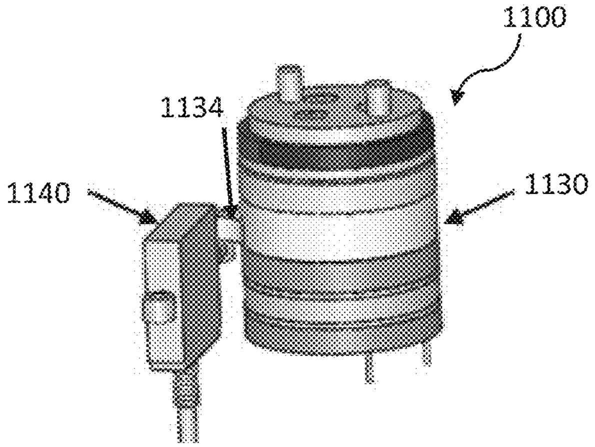
FIGS. 11C and 11D are schematics of a load cell connector ring in the rotary axis drive depicted in FIG. 11A.
Figure 11D:
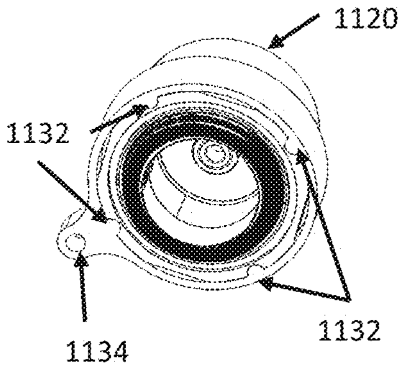
Figure 11E:
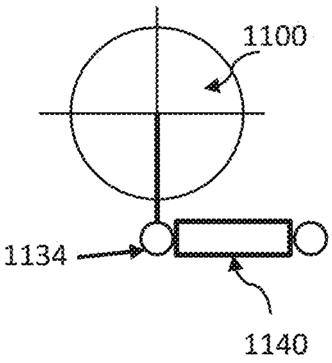
FIGS. 11E and 11F are schematic illustrations of variations of load cell placement in the rotary axis drive depicted in FIG. 11A.
Figure 11F:
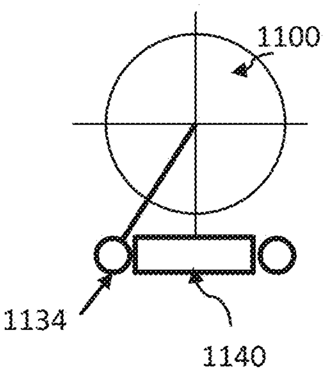

A load cell connector ring 1130 may be disposed circumferentially around the harmonic drive 1120 and configured to couple the motor assembly 1110 to a load cell 1140 for measurement of force and/or torque loads on the motor assembly 1110. For example, as shown in FIGS. 11C and 11D, the load cell connector ring 1130 may include a mounting tab 1134 extending radially outward and configured to couple to a connecting feature on a load cell 1140. For example, the mounting tab 1134 may couple to the load cell via a pin and bushing arrangement. As another example, the mounting tab 1134 may couple to the load cell via a radial bearing, or other suitable connection mechanism. The load cell connector ring 1130 may be oriented relative to the rest of the motor assembly 1110 in facilitate any suitable positioning of the load cell. For example, as shown in FIG. 11E, the mounting tab 1134 on the load cell connector ring may be oriented such that the load cell 1140 is generally orthogonal to the mounting tab 1134, or one end of the load cell 1140 is tangent to the motor assembly 1110. As another example, as shown in FIG. 11F, the mounting tab 1134 on the load cell connector ring may be oriented such that the load cell 1140 is generally at an acute angle relative to the mounting tab 1134, or a midline or other point between the two ends of the load cell 1140 is tangent to the motor assembly 1110. Furthermore, as shown in FIG. 11D, the load cell connector ring 1130 may further include one or more mechanical keys (e.g., one or more radial tabs or keys 1132) for fixed relative positioning between the load cell connector ring 1130 and the harmonic drive, such that rotational motion of the harmonic drive corresponds to rotational motion of the load cell connector ring 1130.

Figure 12A:
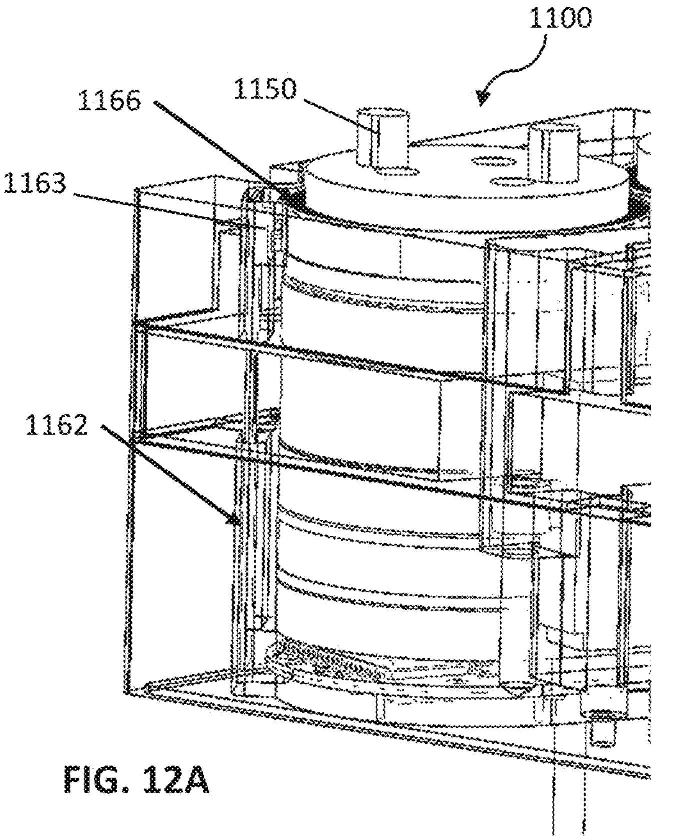
FIG. 12A is a perspective view of a side-mounted encoder board.
Figure 12B:
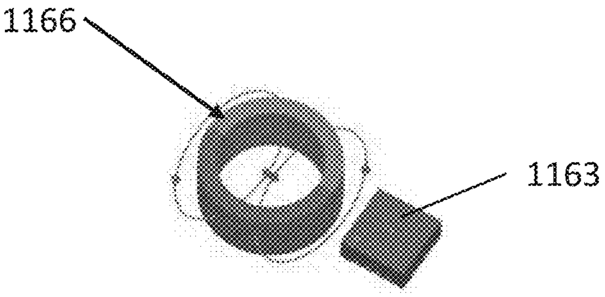
FIG. 12B is a schematic illustration of an encoder ring magnet and a side-mounted encoder sensor.

An output encoder magnet may be coupled to the motor coupling disc 1150 (or alternatively, the output of the motor assembly 1110 in another suitable manner) to measure rotational position of the output of the motor assembly. For example, as shown in FIGS. 11A and 11B, a ring magnet 1166 may be disposed around a central region of the motor coupling disc 1150 so as to rotate with the output of the motor assembly 1110. An encoder sensor 1163 may be positioned adjacent the ring magnet 1166 to measure fluctuations of the magnetic field from the ring magnet 1166, as shown in FIG. 12B. In some variations, as shown in FIG. 12A, the encoder sensor 1163 may be positioned substantially in-plane with the ring magnet 1166 to face the outer diameter of the ring magnet 1166, such as on a PCB 1162 mounted along the side of the motor assembly 1100 (aligned with the rotational axis of the motor assembly 1100). Accordingly, as shown in FIG. 10D, in one exemplary variation with six motor assemblies, there may be provided six side-mounted PCBs 1162*a*-1162*f*, with respective encoder sensors facing motor assemblies 1030*a*-1030*f*, respectively. The side-mounted PCB arrangements may, for example, help reduce overall volume of the tool carriage.

Figure 13A:
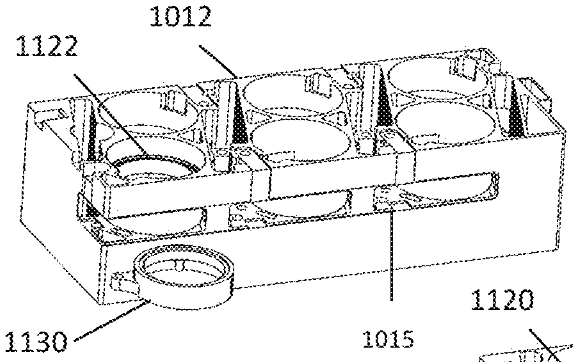
FIGS. 13A-13E are illustrative schematics depicting an exemplary assembly process for one variation of a tool carriage with a plurality of rotary axis drives.
Figure 13B:
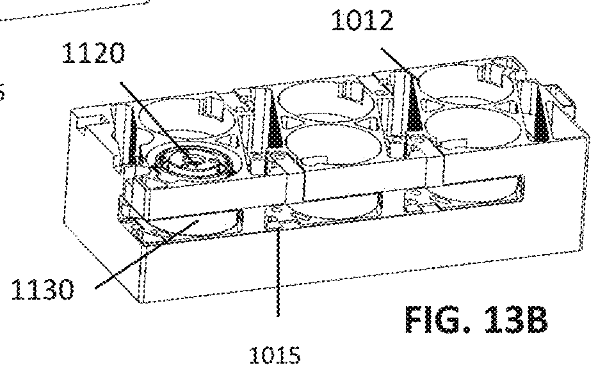
Figure 13C:
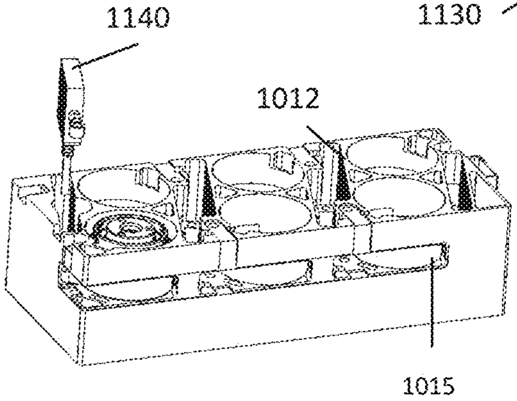
Figure 13D:
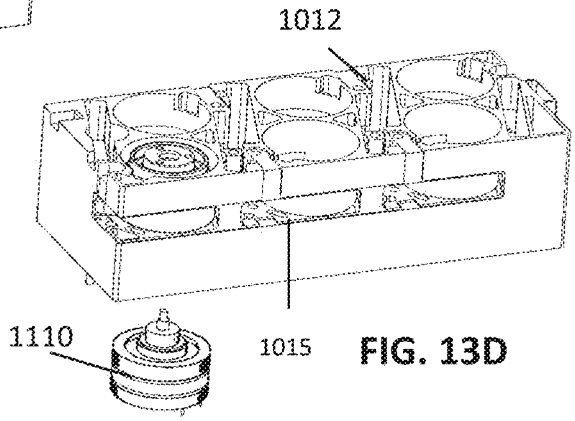
Figure 13E:
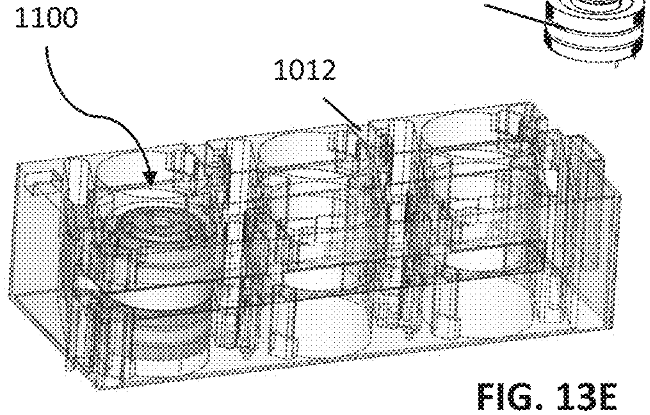

One exemplary method of assembly of one variation of the tool carriage having one or more instances of rotary axis drives 1100 is shown in FIGS. 13A-13E. As shown in FIG. 13A, a bearing 1122 may be placed into a rotary axis drive opening in the housing body 1012 and a load cell connector ring 1130 may be inserted laterally through a slide slot 1015 in the housing 1012. Thereafter, a harmonic drive 1120 may be placed into the bearing 1122 mounted in the housing body 1012 as shown in FIG. 13B, and a load cell 1140 may be placed into a load cell opening in the housing body 1012 as shown in FIG. 13C. As shown in FIG. 13D, a motor assembly 1110 may be placed and engaged with the harmonic drive 1120. As a result, the rotary axis drive 1100 may be fully assembled within a respective rotary axis drive opening in the housing body 1012. The process may be repeated for multiple instances for multiple rotary axis drives. Finally, a side shield 1014 (e.g., as shown in FIG. 10C) may couple to the housing body 1012 so as to cover the side slot 1015, thereby contributing to enclosing the rotary axis drives within the tool carriage. Other methods of assembly are envisioned, such as assembling the rotary axis drive outside of the housing body 1012 and placing (e.g., dropping in) the entire assembled rotary axis drive into a respective opening in the housing body 1012.

Rotary Axis Drives With Planetary Gear Train

Figure 14A:
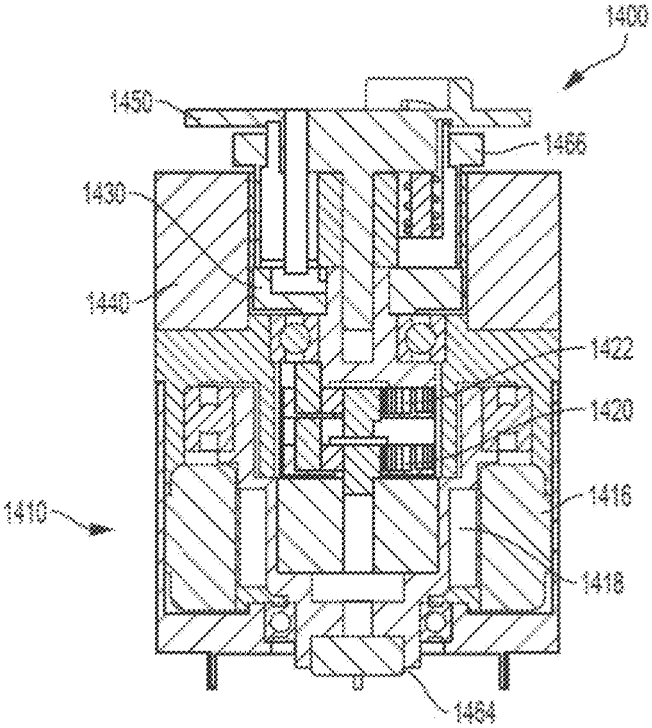
FIGS. 14A-14C are longitudinal cross-sectional views of one variation of a rotary axis drive with a compliant motor coupling disc.
Figure 14B:
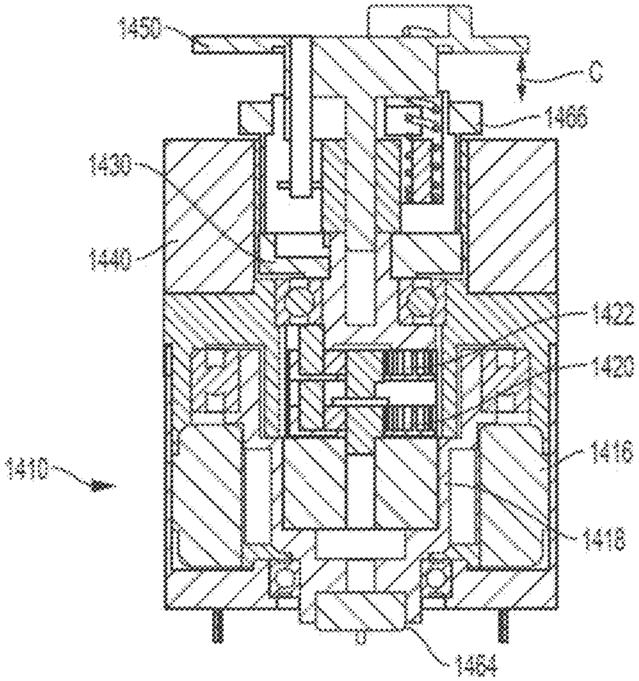
Figure 14C:
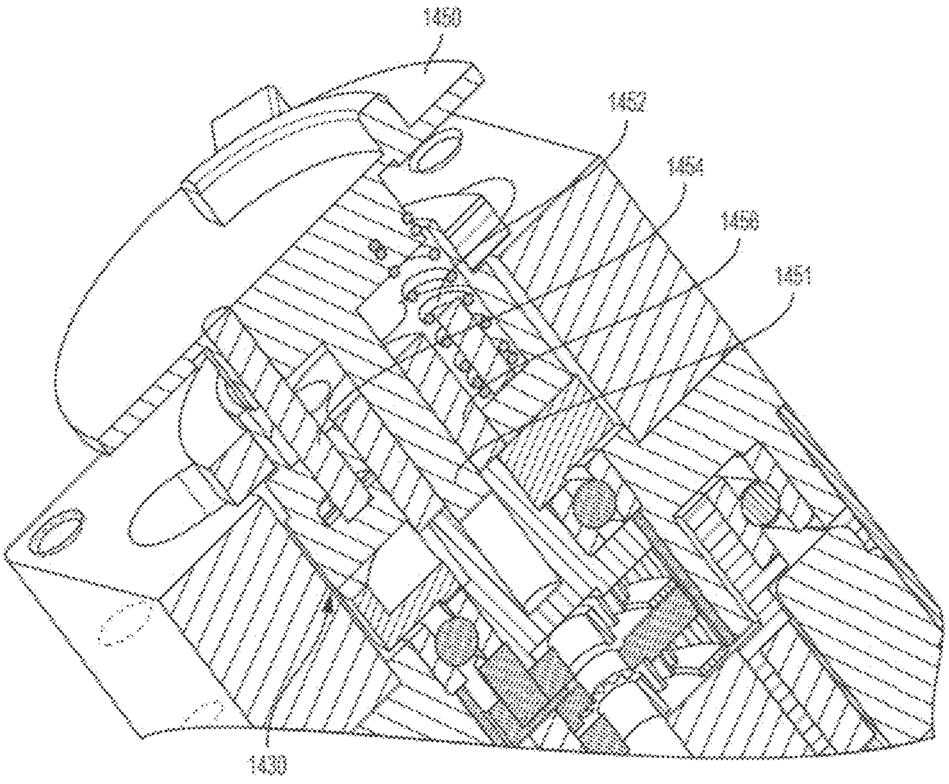

In another variation of the tool carriage, the tool carriage includes a plurality of rotary axis drives where at least one has a planetary gear train coupled to the output of a motor assembly. For example, as shown in FIGS. 14A-14C, a rotary axis drive 1400 may include a motor assembly 1410, a planetary gear train with at least a first planetary gear stage 1420 coupled to an output of the motor assembly 1410, a torque sensor 1430 coupled to an output of the planetary gear train, and a compliant motor coupling disc 1450 configured to couple an output of the rotary axis drive 1400 to a tool and/or sterile adapter to a tool. The compliant motor coupling disc 1450 may be spring-loaded to be biased distally by at least one spring 1452, but may adjustably move proximally upon a proximally-directed force (e.g., engagement with a tool or sterile adapter to a tool).

Like the motor assembly 1110, the motor assembly 1410 may include a stator 1416 and a rotor 1418 rotatable relative to the stator 1416, and any suitable housing components to at least partially enclose the stator and/or rotor. An input encoder 1464 may be disposed to measure angular or rotational position of the rotor 1418 (and output shaft of the motor assembly 1410). The motor assembly 1410 may be, for example, a servomotor or other suitable kind of actuator.

At least a first planetary gear stage 1420 may be coupled to an output shaft of the motor assembly and be configured to increase the torque of the motor assembly 1410 by a prescribed amount in accordance with the gear ratios of the first planetary gear stage 1420. Furthermore, in some variations, a second planetary gear stage 1422 may be coupled to the output of the first planetary gear stage 1420 to further increase the output torque. A torque sensor 1440 may have a bore that receives a rotary output coupler assembly 1430, such that the torque sensor 1440 is configured to measure torque loads on the motor assembly 1400.

As shown in FIG. 14C, the rotary output coupler assembly 1430 may include a motor coupling disc 1450 connected to a motor coupling shaft 1451, where the rotary output coupler assembly 1430 is coupled to the output shaft of the motor assembly and is configured to move in both rotational and translational manners. For rotational motion, the motor coupling disc 1450 may be coupled to the output of the planetary gear train via a drive pin 1454 operating similar to a mechanical key, such that the motor coupling disc 1450 rotates with the output of the planetary gear train. An output encoder 1466 may be disposed proximate the motor coupling disc 1450 to measure angular or rotational position of the motor coupling disc 1450. For translational motion, the rotary output coupler assembly 1430 may be coupled to one or more springs 1452 (e.g., multiple springs circumferentially distributed around the motor coupling shaft 1451) for biased linear movement toward an extended, tool-engaging position. For example, one or more pre-loaded compression springs 1452 may be coupled to the coupler assembly 1430 with retaining rings or other suitable mechanism. The one or more springs 1452 may be configured to urge rotary output coupler assembly 1430 outwards to an extended position, and one or more linear bearings 1451 (e.g., bushing or sleeve bearing) may be provided to reduce friction of this translational movement. The one or more springs 1452 may make the rotary output coupler assembly 1430 compliant in an axial direction as indicated by the arrow C in FIG. 14B and in a comparison of the position of the motor coupling disc 1450 in FIGS. 14A and 14B. The extended position of the rotary axis drive output coupler may provide a pre-determined distance of compliance (e.g., 3-4 mm) that may, for example, be conducive for engaging with the input of a surgical tool and/or sterile barrier located between the tool driver and the tool, etc.

Figure 15A:
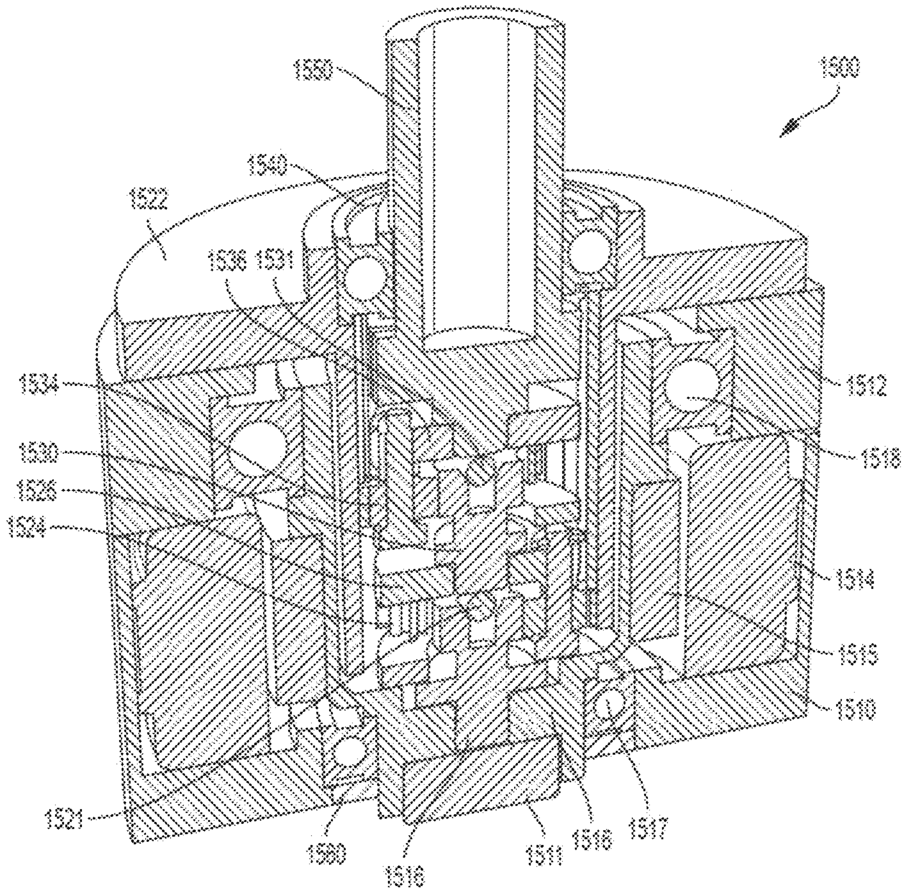
FIG. 15A is a longitudinal cross-sectional view of one variation of a rotary axis drive with a planetary gear train at least partially disposed in a motor in the rotary axis drive.
Figure 15B:
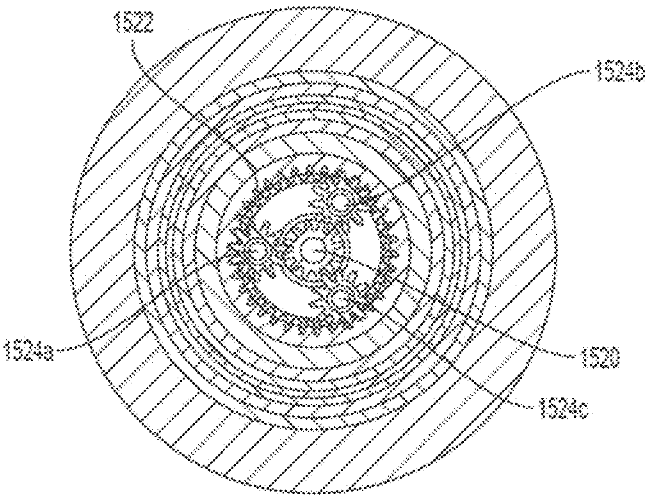
FIG. 15B is an axial cross-sectional view of the rotary axis drive depicted in FIG. 15A.

In another variation of the tool carriage, the tool carriage includes a plurality of rotary axis drives, wherein at least one rotary axis drive includes a motor with a hollow rotor and a planetary gear transmission at least partially disposed within the hollow rotor. For example, as shown in FIGS. 15A and 15B, a rotary axis drive 1500 may include a motor with a hollow rotor shaft 1516 encompassing a planetary gear box inside the motor. As a result, the overall length of the rotary axis drive 1500 along the axis of rotation is reduced, relative to conventional motor-gear train drives in which the gearbox is located outside of the motor. Therefore, the packaging size of the rotary axis drive is greatly reduced while still providing desired torque increase, which may be advantageous for the tool driver by ceding room for additional sensors (e.g., torque/force sensors, encoders, etc.), mechanisms (e.g., couplings), or other components. Reduction of size of the rotary axis drive also may reduce the overall volume of the tool driver and/or overall robotic system (e.g., arm manipulator and tool driver system) to enable increased patient access and reach in the application of robotic surgical systems, and/or may reduce mass and inertia, thereby improving the performance of a robotic system in which the rotary axis drive is implemented.

As shown in the longitudinal cross-sectional view of FIG. 15A, the rotary axis drive 1500 may include a motor (e.g., frameless, brushless DC servomotor) including a housing (e.g., lower housing 1510 and upper housing 1512 in combination) forming an internal volume. Disposed in the internal volume may be the rest of the motor and at least some of the gear train components, such as an annular stator 1514 mounted in the lower housing 1510, an annular rotor magnet 1515 nested within the stator 1514, and a hollow rotor 1516 nested within the annular rotor magnet 1515 such that the rotor 1516 is configured to rotate relative to the stator 1514 given suitable manipulations of the rotor magnet 1515. The hollow rotor 1516 may be supported in the housing at a proximal end by a first radial bearing 1517 and at a distal end by a second radial bearing 1518. Outer races of the first radial bearing 1517 and the second radial bearing 1518 may be coupled (e.g., by press-fit) to the lower housing 1510 and the upper housing 1512, respectively, while the inner races of the first and second radial bearings 1517 and 1518 may be coupled to the rotor shaft. Accordingly, the rotor shaft 1516 may be free to rotate around a longitudinal axis relative to the stator 1510 and housing.

At least one planetary gear stage disposed inside the rotor shaft 1516 may include an annular gear 1522, a sun gear 1516, and a plurality of planet gears 1524 supported by a carrier 1526. The annular gear 1522 for the one or more planetary gear stages is coaxial with the motor and serves as a fixed reference for the planetary gear stages. The annular gear 1522 may include a flange that couples the annular gear to the upper housing 1512, though the annular gear 1522 may additionally or alternatively be fixed to the housing in any suitable manner. The annular gear 1522 may have a hollow shaft extending from the flange, where the internal surface of the hollow shaft has gear teeth and the external surface of the hollow shaft is sized such that there is a physical clearance (i.e., no touching) between the hollow shaft of the annular gear 1522 and the rotor shaft 1516. The sun gear 1516 may be mounted at a proximal or base end of the rotor shaft 1516 (e.g., mounted to a bottom wall 1511 of the rotor shaft) to be centered within and co-axial with the rotor shaft 1516. The sun gear 1516 may rotate coaxially within the rotor shaft 1516, for example, around a supporting member 1512. A plurality of planet gears (e.g., three or more) traveling on a carrier 1526 may be configured to engage with the annular gear 1522 and the sun gear 1516. For example, as shown in FIG. 15B, the planet gears 1524*a*, 1524*b*, and 1524*c* may be about equally distributed around the sun gear 1520 (e.g., arranged about 120 degrees from one another), and simultaneously engage the annular gear 1522 and the sun gear 1520. The sun gear 1520 is an input to the gear train (e.g., by receiving the output or the rotational motion of the rotor 1516), while the planet carrier is the output of the gear train (e.g., by rotating as a result of the movement of the planet gears 1524*a-c* engaging with the sun gear 1520).

A second planetary gear stage may be additionally disposed inside the rotor shaft 1516 and chained with the first planetary gear stage. For example, the second planetary gear stage may include a second sun gear 1530 and a second plurality of planet gears 1534 supported by a second carrier 1536. The second sun gear 1530 may be coupled to the first planet carrier 1526 output of the first planetary gear stage and may be supported by a second sun gear support member 1531. The second plurality of planet gears 534 may be configured to engage the annular gear 1522 and the second sun gear 1530, such that the second carrier 1536 becomes the output of the second planetary gear stage. Third, fourth, and other suitable additional planetary gear stages may further be placed in series with the first and second planetary gear stages in a similar manner.

In the final planetary gear stage, the last planet carrier may be coupled to an output shaft 1550, which is supported by a radial bearing 1540 facilitating rotational motion relative to the annular gear 1522. In some variations, the outer race of the bearing 1540 may be fixed to a counterbore in the annular gear via a clamp (not shown). The radial position of the output shaft 1550 relative to the bearing 1540 may, for example, be fixed by a combination of the second gear support member 1531 urging the output shaft 1550 distally, and a spring washer (not shown) urging the output shaft 1550 proximally. Other support mechanisms (e.g., shims, shim washers, thrust bearings, compression springs, etc.) may be included to support the various planetary gear stage components and/or other components of the motor assembly. For example, the planet gears may be supported on pins retained in place via retaining rings, though screws, bearings, and/or other fasteners may additionally or alternatively be used.

In some variations, a magnet for an on-axis magnetic encoder (e.g., ring magnet or ring-shaped optical encoder) may be coupled near the proximal end of the motor assembly for determining the rotational position of the rotor shaft 1516. For example, such a magnet or encoder 1560 may be disposed on the lower (more proximal) side of the first bearing 1517 for measuring input rotation of the motor assembly. Additionally or alternatively, in some variations, the motor assembly may include one or more sensors (not shown) disposed around the output shaft (e.g., around the support bearing 1540, above the flange of the annular gear 1522), such as a reaction torque sensor, output rotary encoder, etc.

Although the variation depicted in FIG. 15A includes the sun gear as driving input while the annular gear is a fixed reference, in other variations, the various gear components may be driven and fixed in any suitable combination to provide a suitable output of the planetary gear stage. For example, the annular gear may be the driving input while the sun gear is a fixed reference. As another example, the sun gear may be the driving input while the carrier is a fixed reference. As yet another example, the annular gear may be the driving input while the carrier is a fixed reference.

Rotary Axis Drive With Cycloid Transmission

As shown in FIGS. 16A-16E, in another variation of the tool carriage, a tool carriage 1600 may include one or more of rotary axis drives including a cycloid transmission. A cycloid transmission may enable the tool carriage and tool driver to have a low profile in a compact configuration of rotary axis drives (e.g., reduced length of the rotary axis drives measured along the axis of rotation). In some variations, for example, a rotary axis drive including a cycloid transmission as shown in FIG. 16A-16E may have a length of between about 13 mm and 20 mm, or between 15 mm and 17 mm. As described above, benefits of a reduced volume of tool driver and/or overall robotic system are described above may include provision of room for additional sensors, mechanisms, or other components, as well as advantageously enable increased patient access and reach due to reduced system volume, and improved system performance due to reduced mass and inertia.

Figure 16D:
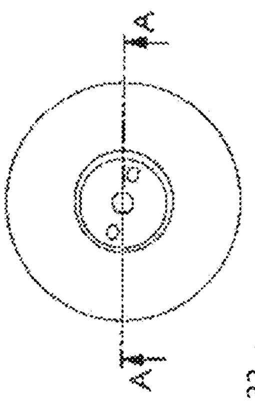
FIG. 16D is a top view of a rotary axis drive with a cycloid-based transmission.
Figure 16E:
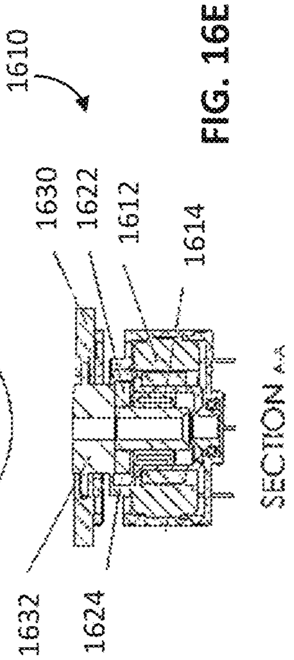
FIG. 16E is a longitudinal cross-sectional view of the rotary axis drive depicted in FIG. 16D, taken along the line A-A.
Figure 16C:
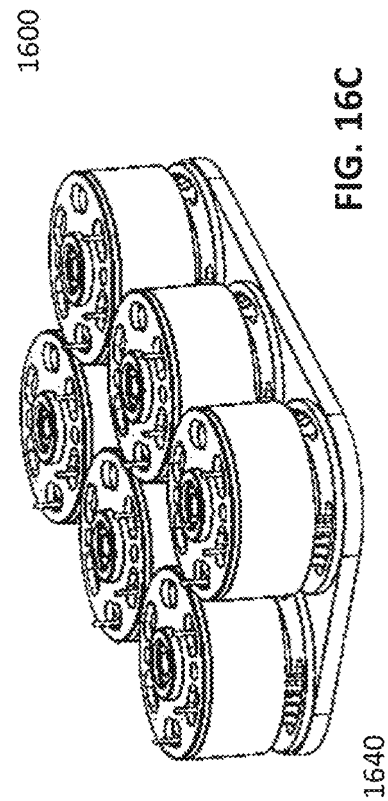
FIGS. 16A-16C are top, side, and perspective views, respectively, of one variation of a tool carriage having rotary axis drives with cycloid-based transmissions.
Figure 16A:
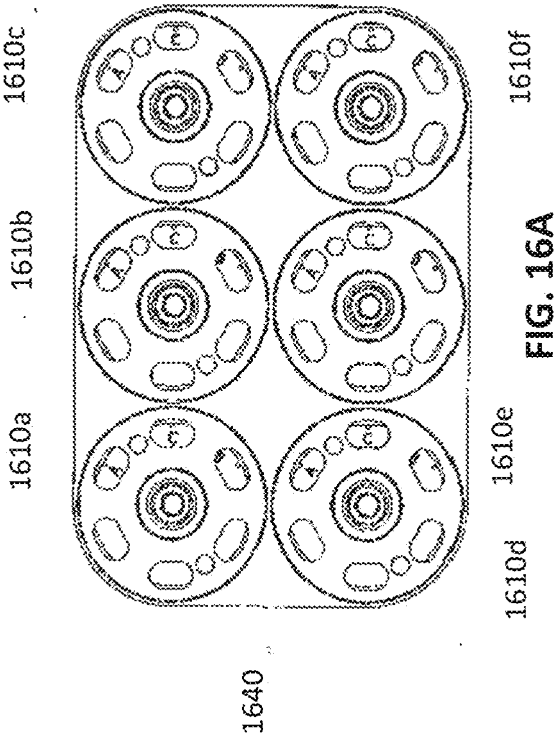
Figure 16B:
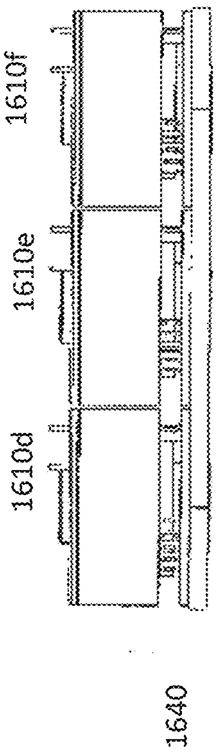

As shown in FIGS. 16A-16C, a tool carriage 1600 may include a plurality of rotary axis drives, such as six rotary axis drives. The rotary axis drives may be staggered or may be arranged in a grid-like fashion as shown in FIG. 16A. Furthermore, the tool carriage 1600 may include any suitable number of rotary axis drives (e.g., fewer than six, or more than six). The rotary axis drives may be mounted on, for example, a bottom housing plate 1640 or other suitable base. As shown in FIG. 16E, at least one of the rotary axis drives 1610 includes a motor 1612 and a cycloid transmission (including a ring gear 1624 and a planet gear 1622 engaged with the ring gear 1624. The motor 1612 may be, for example, a frameless DC servomotor, but may alternatively be any suitable actuator.

The cycloid transmission may be coupled to or integrated with the output of the motor 1612. The cycloid transmission is a single stage reduction transmission that may be used to reduce the profile of the rotary axis drive without sacrifice in gear ratio for increased torque output of the rotary axis drive. The cycloid transmission may include an eccentric, rotating planet gear 1622 engaged with a ring gear 1624, while the motor 1612 may include a rotating rotor 1614. In some variations, the rotor 1614 may be hollow and include a bore, and the planet gear 1622 may be disposed in the bore of the 1614, thereby further reducing the profile of the combined motor 1612 and cycloid transmission.

However, a cycloid transmission typically requires a mechanism to rectify misalignment in a drive coupling due to the rotational movement of the eccentric planet gear 1622 in the cycloid transmission. In order to rectify such misalignment, the drive coupling that couples the output of the cycloid transmission to a tool (or sterile barrier of a tool) may include an Oldham coupling. For example, in some variations, the tool carriage depicted in FIGS. 16A-16C may be configured to actuate a surgical tool coupled to the tool driver through a sterile adapter disposed between the non-sterile drive axes of the tool carriage and the sterile surgical tool. In such variations, as shown in FIG. 16E, the respective drive discs 1630 in the sterile adapter may include an Oldham coupling 1632 for rectifying movement of the planet gear. By incorporating an Oldham coupling in the sterile barrier itself, a separate Oldham coupling and output bearing assembly (typically seen coupled to the output of conventional cycloid transmissions) need not be included, thereby further reducing the height and overall volume of the tool carriage 1600.

Rotary Axis Drive With Torque Sensor

Figure 17A:
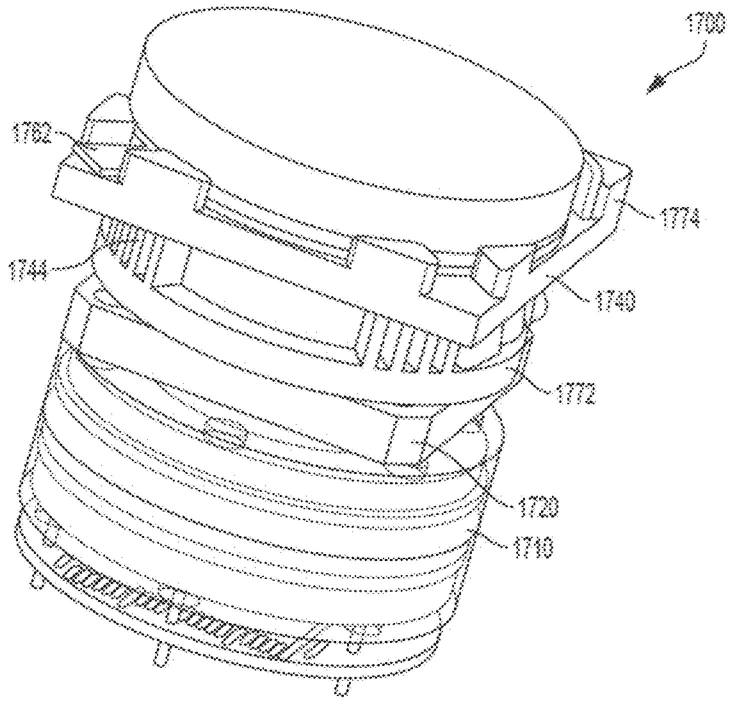
FIGS. 17A and 17B are perspective and longitudinal cross-sectional views, respectively, of one variation of a rotary axis drive with an integrated reaction torque sensor assembly.
Figure 17B:
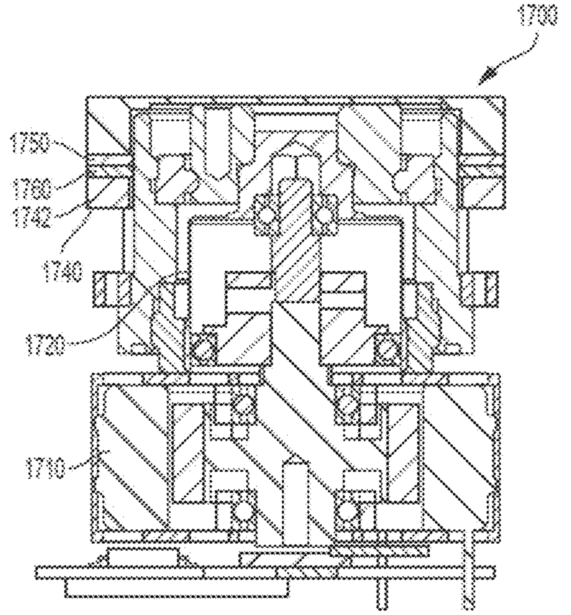

As shown in FIGS. 17A and 17B, in another variation of the tool carriage, the tool carriage may include one or more rotary axis drives 1700 having a motor 1710, a transmission 1720 (e.g., harmonic drive) coupled to an output of the motor 1710, and a torque sensor assembly 1740 which is integrated with the transmission 1720 (e.g., harmonic drive, planetary gear train, etc.) as described below with respect to FIGS. 23A-23F. The torque sensor assembly 1740 may be configured, for example, to measure reaction torque experienced by the rotary axis drive 1700. The rotary axis drive 1700 with integrated torque sensor assembly 1740 may result in a more compact, low-profile tool carriage. Exemplary variations of torque sensor assemblies are further described below.

Figure 19B:
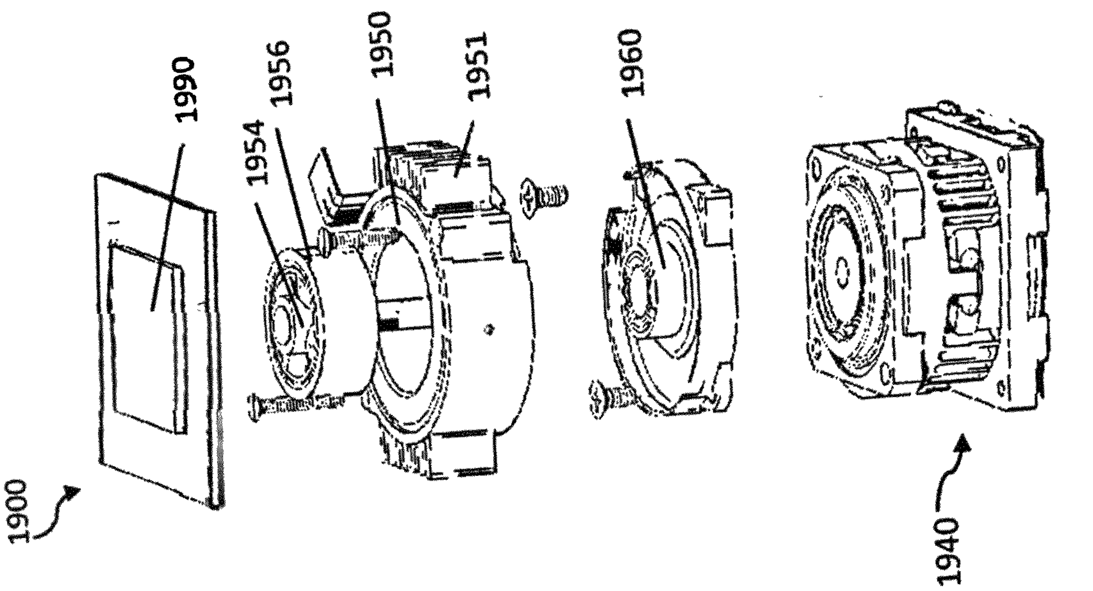
FIGS. 19A and 19B are a longitudinal cross-sectional view and an exploded perspective view, respectively, of another variation of a rotary axis drive with an integrated torque sensor assembly and thermal management features.
Figure 19A:
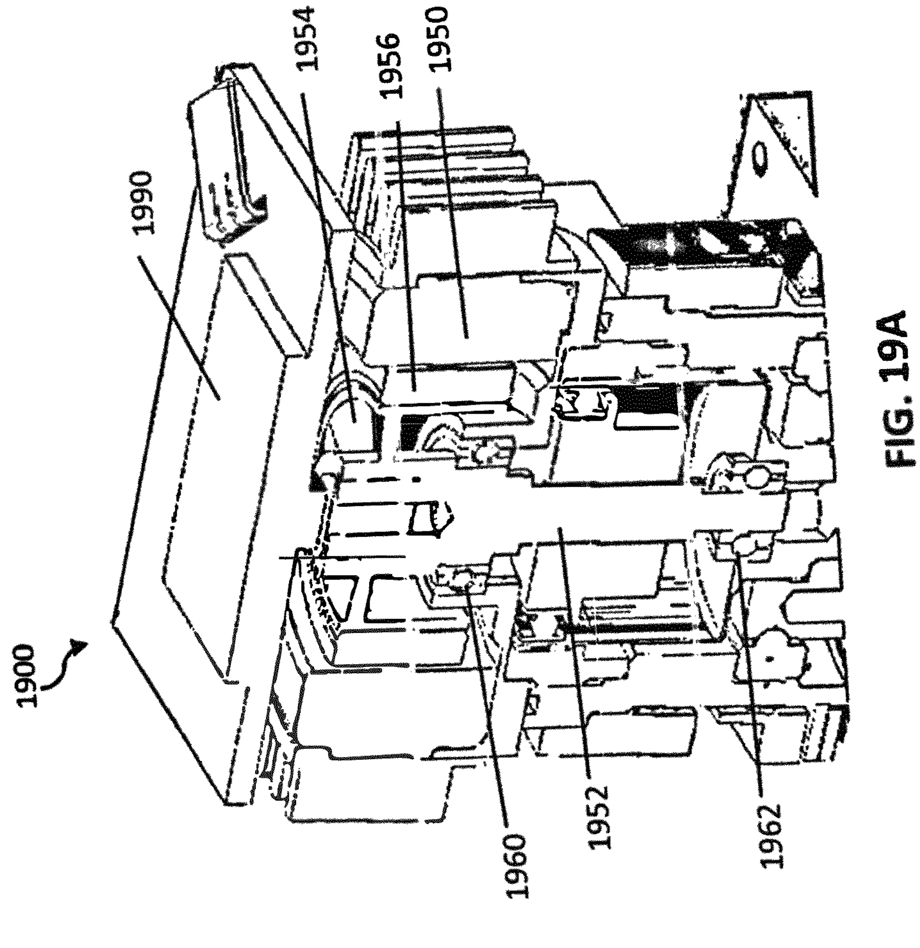

FIGS. 19A and 19B depict another variation of a rotary axis drive 1900 that is similar to rotary axis drive 1700, except rotary axis drive 1900 may include additional features for thermal management purpose. For example, like rotary axis drive 1700, rotary axis drive 1900 may include a motor, a transmission 1960 (e.g., harmonic drive) coupled to an output of the motor, and a torque sensor assembly 1940 similar to torque sensor assembly 1740 described above. The motor may include a stator 1950, a rotor shaft 1952, and a rotor magnet 1956 configured to induce rotation of the rotor shaft 1952 relative to the stator 1950. The rotor shaft 1952 may be supported by a proximal support bearing 1960 and a distal support bearing 1962 positioned as far apart as possible so as to help maintain the axial alignment of rotor shaft 1952 within the motor. Clearance between the rotor magnet and the motor housing may help avoid eddy current losses for the motor. Electronics for control of the rotary axis drive 1900 (e.g., motor driver, power, etc.) may be located on a motor PCB 1990 coupled to the proximal end of the rotary axis drive 1900, or alternatively in any suitable location. Additional features to help increase cooling of the rotary axis drive 1900 may include, for example, a fan 1954 coupled to the rotor shaft to help circulate air within the motor body, fins 1951 on the external surface of the stator 1950, and/or cavities on the stator 1950 or other components of the motor that may receive thermal conductive epoxy.

Figure 20A:
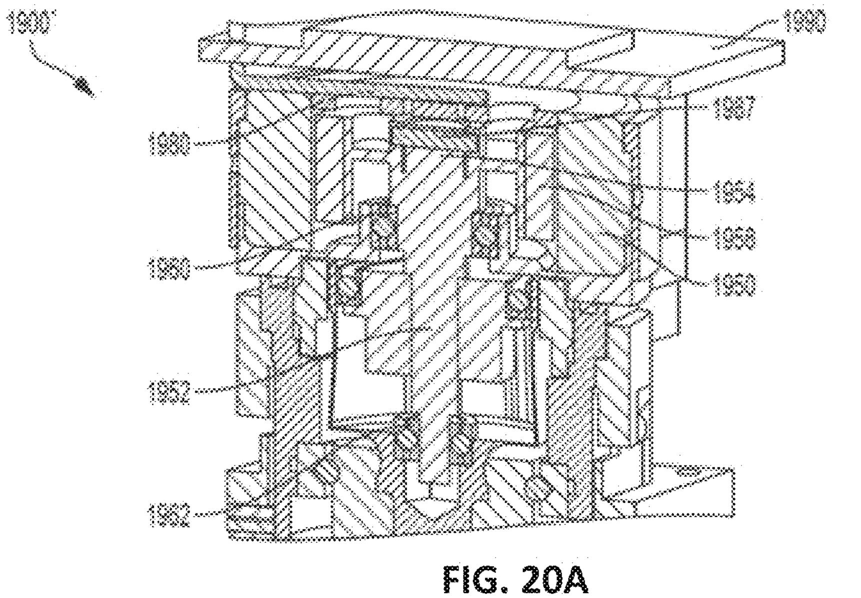
FIGS. 20A and 20B are a longitudinal cross-sectional view and a perspective view, respectively, of another variation of a rotary axis drive with an integrated torque sensor assembly and an input rotary encoder.
Figure 20B:
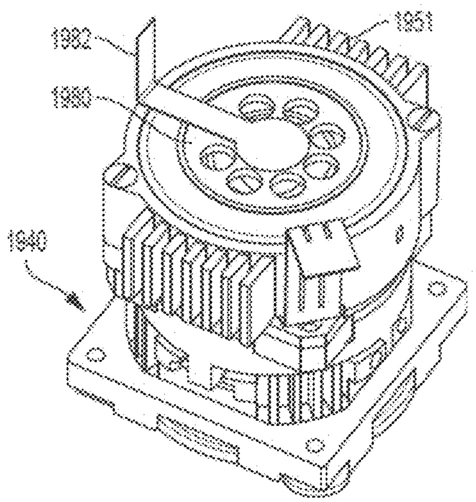
Figure 20C:
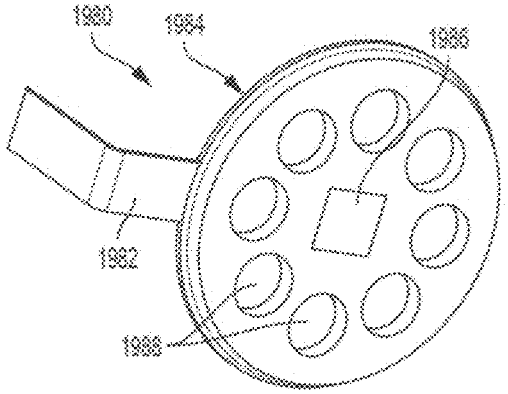
FIG. 20C is a perspective view of the input rotary encoder in the rotary axis drive depicted in FIG. 20A.

In another variation, a rotary axis drive 1900' shown in FIGS. 20A and 20B may be similar to the rotary axis drive 1900, except that the rotary axis drive 1900' further incorporates an input rotary encoder 1980 for determining rotational position of the motor. The encoder 1980 may be disposed at the proximal base of the motor and be connected to the motor PCB 1990 via a flex cable 1982, ribbon cable, or other suitable wiring connection. As shown in FIG. 20C, the encoder 1980 may include an encoder base 1984 supporting an encoder sensor 1986 configured to detect change in magnetic field induced by an encoder magnet (encoder magnet 1987 shown in FIG. 20A) on the base of the rotor shaft 1952 or near the fan 1954. In some variations, there may be a sufficient amount of physical clearance between the encoder magnet 1987 and the proximal bearing 1960 to reduce the influence of the encoder magnet's magnetic field caused by the rotating bearing 1960. The encoder base 1984 may be made of a polymer or other suitable material (e.g., PEEK, ULTEM, etc.) that is suitable for handling high temperatures. Furthermore, the encoder base 1984 may include one or more cutouts 1988, which may provide ventilation and air circulation for cooling purposes.

Figure 37A:
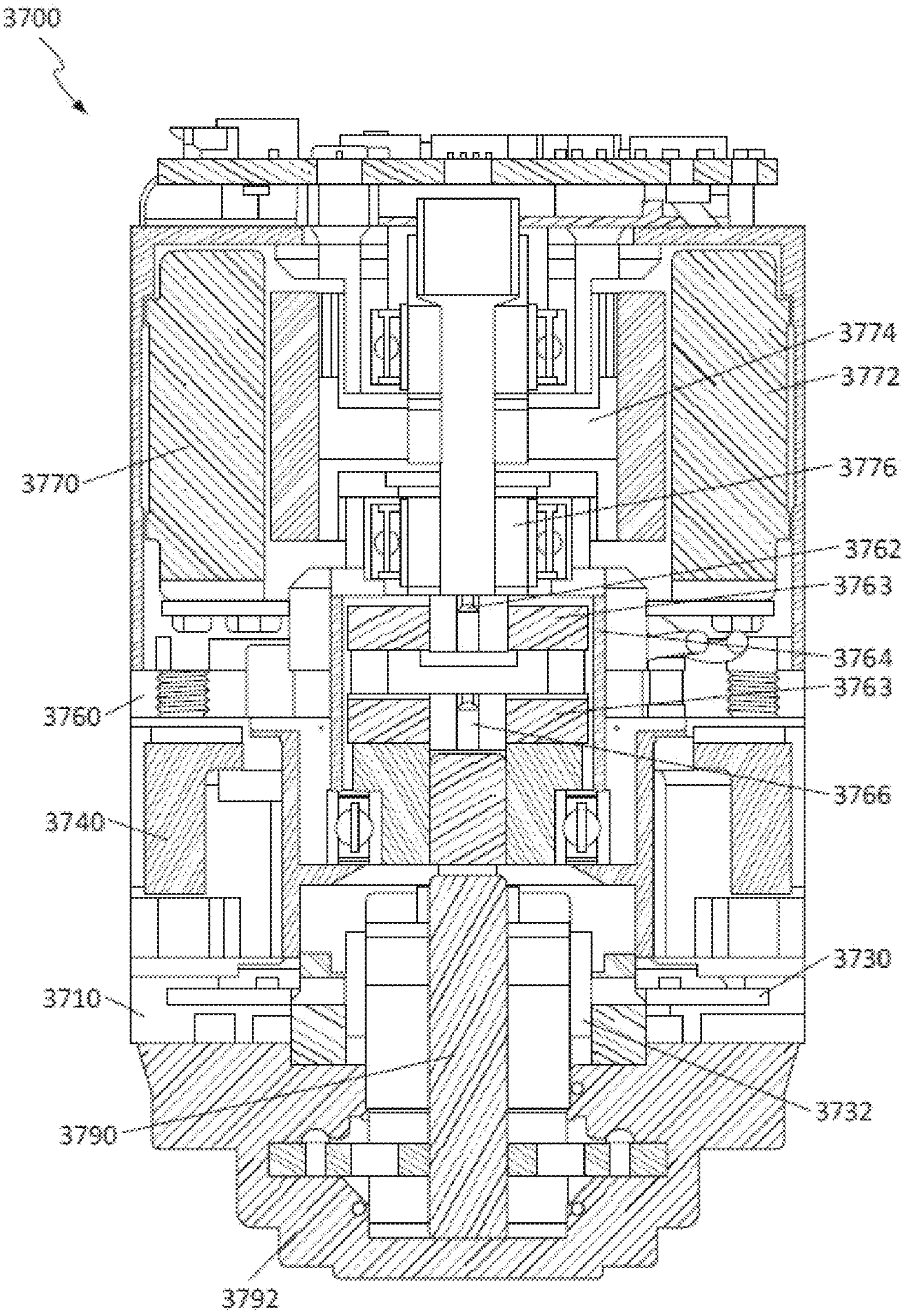
FIGS. 37A and 37B are cross-sectional and perspective cross-sectional views, respectively, of one variation of a rotary axis drive in a tool driver.
Figure 37B:
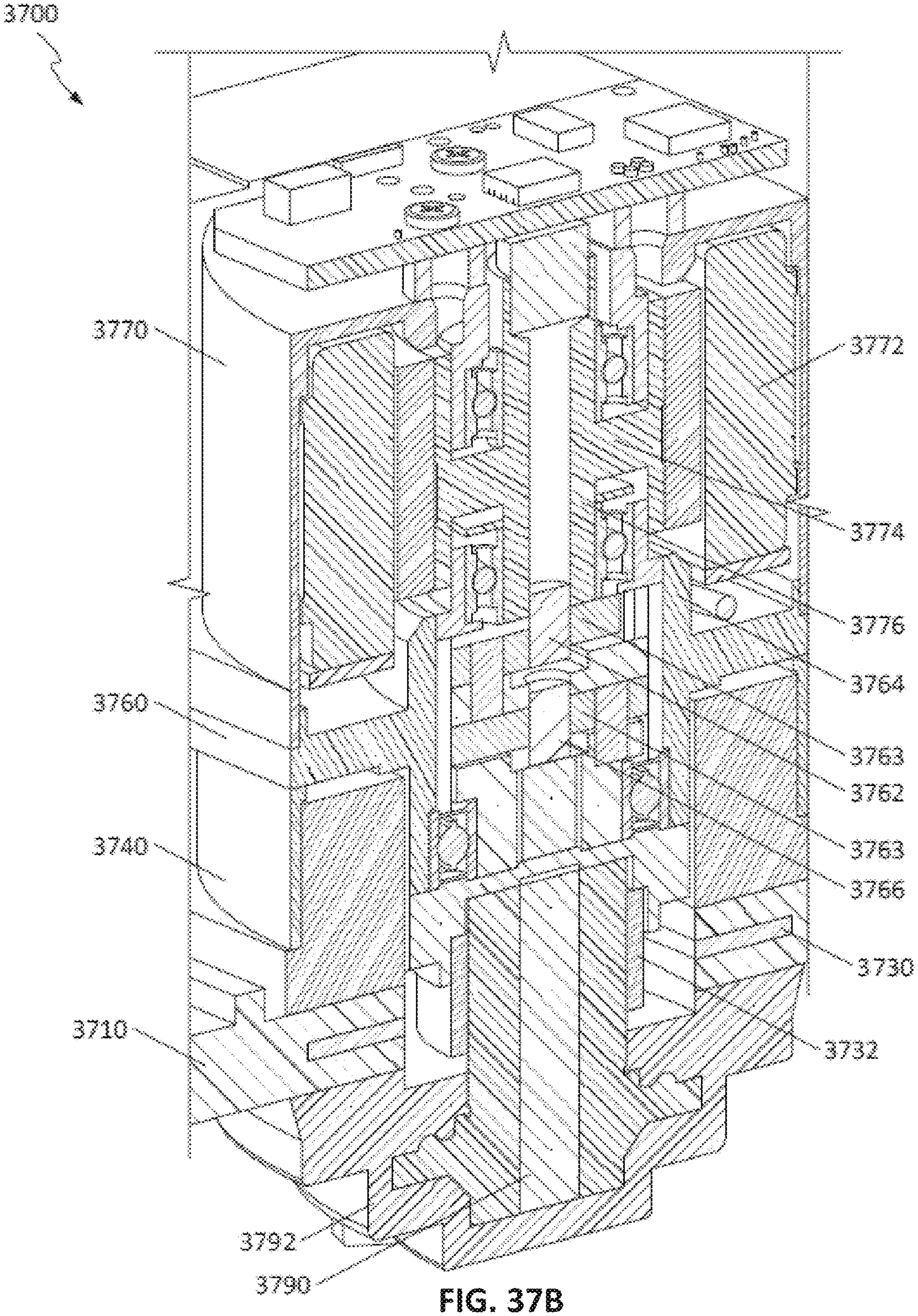

In another variation as shown in FIGS. 37A and 37B, the tool carriage may include one or more rotary axis drives 3700 having a rotary output shaft configured to actuate one or more articulated movements of a surgical tool, such as via an output coupler 3792 coupled to the distal end of the rotary output shaft. The rotary axis drive 3700 may include a motor 3770 having a motor shaft 3776, a gear transmission 3760, and a torque sensor 3740 disposed between the gear transmission and a distal end of the rotary output shaft. The torque sensor 3740 may be configured to measure torque applied to the rotary axis drive 3700, such as reaction torque during actuation. Various other aspects of the rotary axis drive may help enable the torque sensor 3740 to be included proximal to the distal end of the rotary output shaft (e.g., proximal to the output coupler 3792), as described below.

For example, the motor 3770 may include a hollow motor shaft 3776, and the gear transmission 3760 may be at least partially disposed within the motor shaft to reduce longitudinal length of the rotary axis drive attributable to the gear transmission 3760. For example, as shown in FIGS. 37A and 37B, the motor 3770 may include a rotor 3774 configured to rotate relative to a stator 3772. The central axis or motor shaft of the rotor 3774 may include a lumen configured to receive at least a portion of the gear transmission 3760, such as an input shaft of the gear transmission. In some variations, the gear transmission 3760 is a planetary gear train, and at least a portion of an input sun gear 3762 (e.g., a shaft of the gear 3762) may be disposed within the lumen of the motor shaft 3776, such as via press-fit, epoxy, etc. Thus, the input sun gear 2562 rotates as the rotor 3774 and the motor shaft 3776 rotate. The gear transmission 3760 increases the torque provided by the motor 3770, such as due to gear ratios accommodated by the planetary gears 3763, outer ring gear 3763, and output sun gear 3766. The output of the gear transmission (e.g., shaft of output sun gear 3766) may be coupled to the rotary output shaft 3790, such that the resulting torque is communicated to the output coupler 3792. In other variations, more of the gear transmission 3760 may be disposed within the motor shaft (e.g., similar to that described with reference to FIGS. 15A and 15B) to further reduce length of the rotary axis drive.

The rotary axis drive may, in some variations, further include an encoder 3730 configured to measure a rotational position of the rotary output shaft. For example, the encoder 3730 may include one or more Hall effect sensors configured to measure changes in magnetic field generated by an encoder magnet 3732 disposed on the rotary output shaft 3790. As the rotary output shaft 3790 changes in rotational position, the encoder 3730 may generate a signal from which rotational position may be determined. As shown in FIG. 37A, the encoder may be disposed in a recess of the carriage base 3710, so as to not add additional length to the rotary axis drive 3700 when mounted in the carriage base 3710.

In some variations, at least a portion of the rotary output shaft 3790 may be configured to move axially along the axis of rotation of the rotary output shaft. For example, the rotary output shaft 3790 may include or be coupled to a spring-loaded, axially movable component similar to that described above with reference to FIGS. 8B and 8C. In these variations, the encoder magnet 3732 may be disposed on the axially-movable component such that the encoder magnet 3732 moves axially along with the axial movements of the rotary output shaft 3790. Accordingly the encoder 3730 may be further configured to measure an axial position of the rotary output shaft along the axis of rotation, based on changes in the magnetic field generated by the encoder magnet 3732.

Carriage Sensors

In addition to or alternative to the various sensors briefly described above, any one or more rotary axis drives in the tool carriage may include other suitable sensor assemblies for measuring torque, reaction torque, position, or other metrics. Such metrics may be used, for example, for tracking position and orientation of the various degrees of freedom of an end effector on the surgical tool, and/or as force or torque feedback in control algorithms.

Reaction Torque Sensor

Figure 25A:
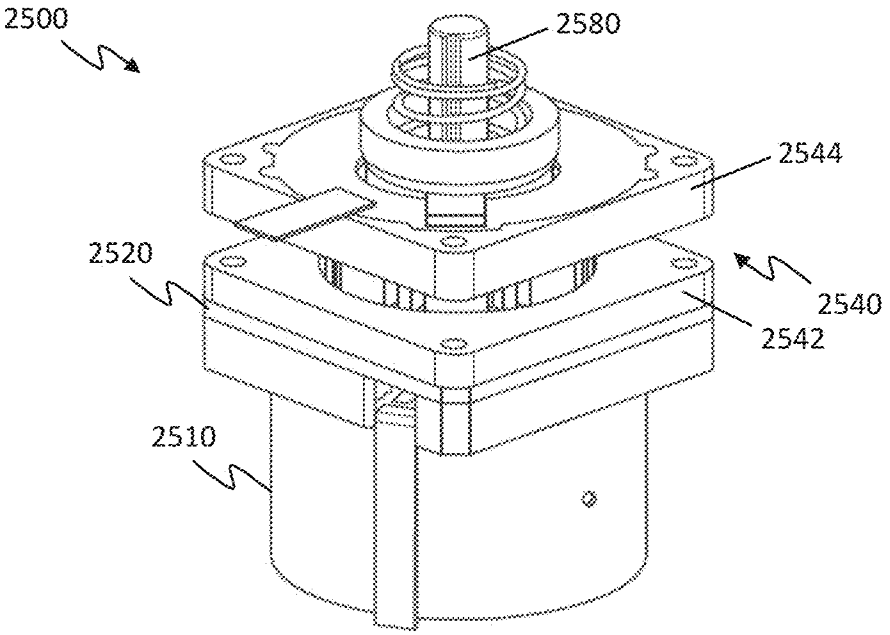
FIGS. 25A and 25B are perspective and cross-sectional views, respectively, of a rotary axis drive with another variation of a torque sensor.
Figure 25B:
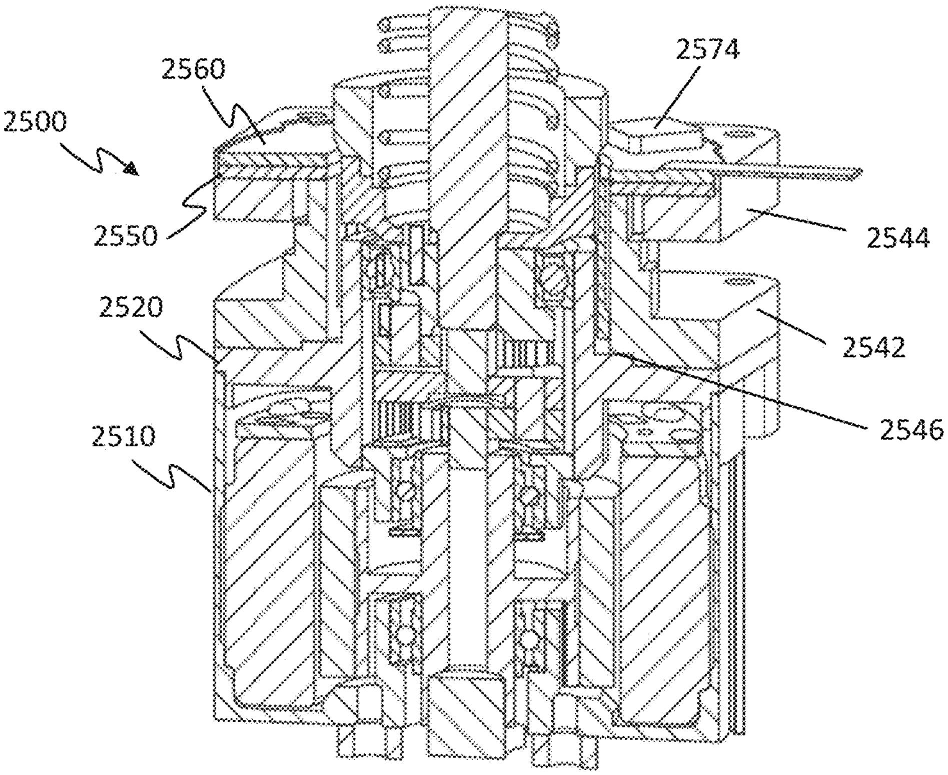

In some variations, one or more rotary axis drives may include an integrated torque sensor assembly for measuring torque on the rotary axis drive output (e.g., reaction torque). As shown in FIGS. 25A and 25B, a rotary axis drive may include, for example, a motor 2510 and a torque sensor assembly 2500 coupled to the motor. The torque sensor assembly 2500 may include a frame 2540 having a proximal frame portion 2542 and a distal frame portion 2544. The torque sensor assembly 2500 may further include a first patterned conductive surface (e.g., on a first conductive plate 2550) and a second patterned conductive surface (e.g., on a second conductive plate 2560) facing the first patterned conductive surface. One patterned conductive surface may be referenced to (e.g., registered to, fixed relative to, etc.) the proximal frame portion 2542, and the other patterned conductive surface may be referenced to the distal frame portion 2544. Generally, as further described below, the torque sensor assembly may be configured to provide a torque measurement based on a differential capacitance between the first and patterned conductive surfaces.

Generally, the torque sensor may provide an accurate measurement of reaction torque when mounted on a rotary axis drive, and in a manner that adds little to no additional volume to the rotary axis drive (thereby contributing to a compact envelope or package size of a tool driver with multiple rotary axis drives). For example, at least in part because the frame is more flexible in rotation than in other degrees of freedom (e.g., axial compression or tension), the torque sensor is robust against cross loads, mechanical misalignment and thermal deformations that interfere with an accurate measurement of reaction torque. The torque sensor frame may be mounted and/or sized (as further described below) in such a way as to require little additional volume, thereby enabling reaction torque measurement in a compact volume.

Figure 26A:
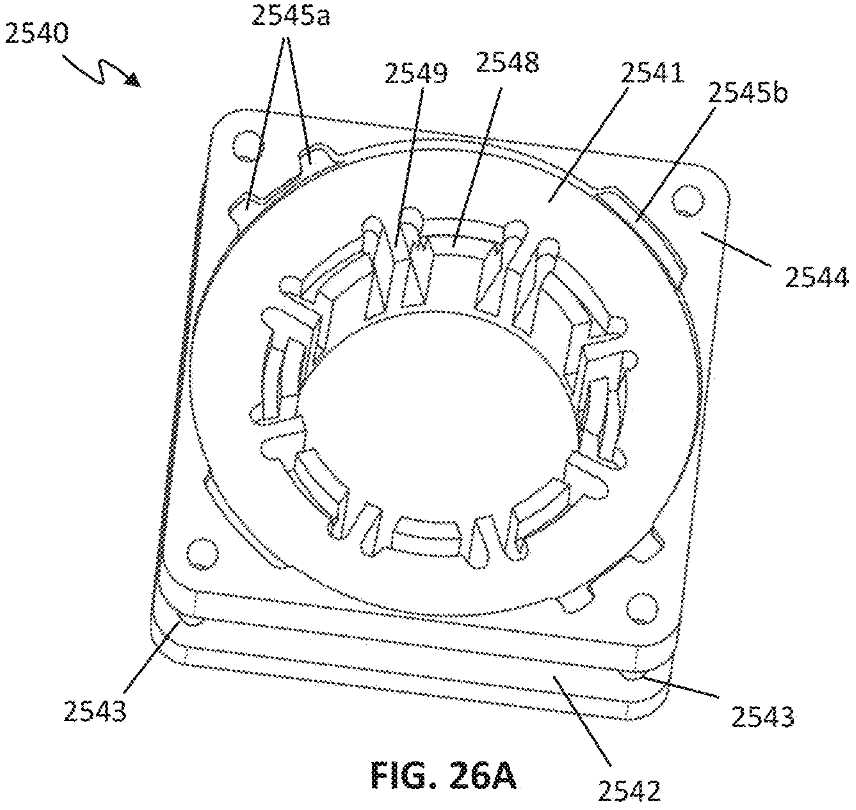
FIG. 26A is a perspective view of a frame in the torque sensor assembly depicted in FIGS. 25A and 25B.
Figure 26B:
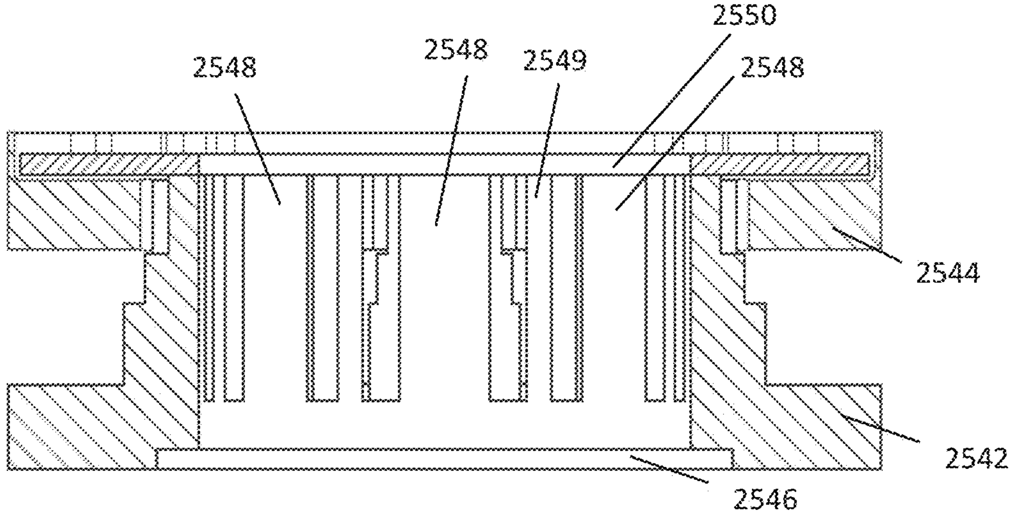
FIG. 26B is a side cross-sectional view of the frame depicted in FIG. 26A with a conductive plate.

As shown in FIG. 26A, the frame 2540 may have a proximal frame portion 2542 and a distal frame portion 2544. The proximal frame portion 2542 may be configured to couple to a portion of the rotary axis drive (e.g., a gear transmission 2520 as shown in FIG. 25A, a distal end of a housing of the motor 2510, etc.). For example, the proximal frame portion 2542 may be configured to couple to a portion of the rotary axis drive via one or more fasteners (not shown) passing through one or more mounting holes 2543. Additionally or alternatively, the proximal frame portion 2542 may be coupled to a portion of the rotary axis drive via an interlocking fit. For example, as shown in FIGS. 25B and 26B, the proximal frame portion 2542 may include one or more cutouts 2546 defining a recess (e.g., square, circular, or any suitable shape) that interlocks in a corresponding and complementary manner (e.g., mechanical key) with an external projection of the transmission 2520 (or other portion of the rotary axis drive). The distal frame portion 2544 may be configured to couple to an actuated object, such that the frame 2540 may experience reaction torque (and relative rotational movement between the proximal and distal frame portions) as the rotary axis drive actuates.

As shown in FIG. 26A, the frame 2540 may further include a plurality of members (e.g., longitudinal ribs or other connecting members). At least some of the members may connect the proximal and distal frame portions. For example, the flexure members 2549 may connect the proximal frame portion 2542 and the distal frame portion 2544 and provide some amount of torsional flexibility such that the frame 2540 acts as a torsional spring. In some variations, aspects of the frame 2540 may be changed to vary the overall torsional rigidity of the frame 2540 (e.g., the spring's resistance against relative twisting of the proximal frame portion 2542 and the distal frame portion 2544). For example, the flexure members 2549 may be varied in cross-sectional shape (e.g., round, square, etc.) and/or thickness (e.g., diameter, width, etc.) in order to increase or decrease the torsional rigidity of the frame 2540. As another example, the orientation of the flexure members 2549 may be varied (e.g., longitudinal, helical, angled, lattice-like, etc.) in order to increase or decrease the torsional rigidity of the frame 2540. As yet another example, the material of the flexure members 2549 and/or other portions of the frame 2540 may be varied in order to increase or decrease the torsional rigidity of the frame 2540.

In some variations, the frame of the torque sensor may be configured to twist up to (e.g., without being stopped by mechanical stoppers) a maximum value that is below about 0.5 degrees, such as between about 0.1 degrees and about 0.5 degrees, between about 0.15 and about 0.45 degrees, or between about 0.2 and 0.4 degrees, etc. For example, the frame may be configured to twist up to about 0.25 degrees in either direction. In some variations, the torque sensor may be configured to have a resolution or precision of torque measurement of within about 1 mNm or less, such as a resolution or precision within about 0.25 mNm and about 0.75 mNm, etc. For example, the torque sensor may be configured to have a resolution or precision of about 0.5 mNm.

In some variations, at least some of the members may function to position at least one of the conductive surfaces relative to a portion of the frame 2540. For example, in the variation shown in FIG. 26B, the anchoring members 2548 may be coupled to the first conductive plate 2550, such that the first conductive plate 2550 is referenced to the proximal frame portion 2542. The first conductive plate 2550 may be coupled to the anchoring members 2548 via epoxy or any suitable manner. In some variations, the anchoring members 2548 may be longer than the flexure members 2549 such that the first conductive plate 2550 (when coupled to the anchoring members) is spaced apart from a clearance surface 2541 (shown in FIG. 26A) on the distal frame portion 2544. Accordingly, the first conductive plate 2550 moves in tandem with the proximal frame portion 2542, and independently from the distal frame portion 2544.

Figure 26C:
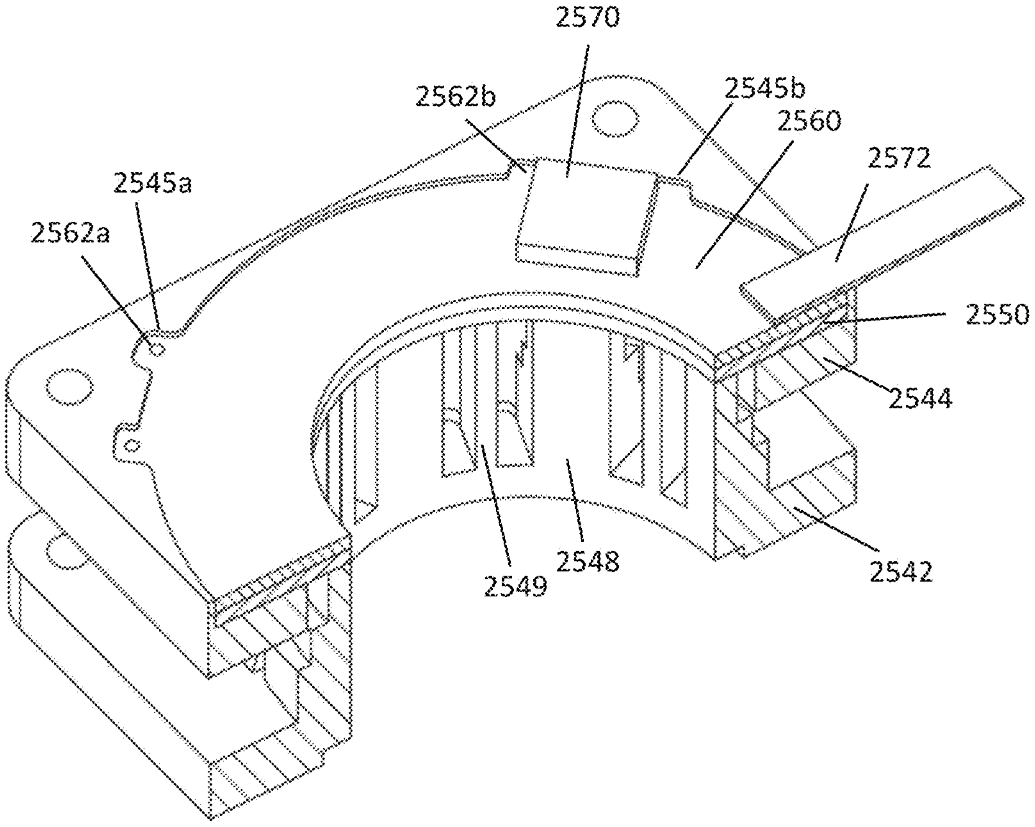
FIG. 26C is a perspective cross-sectional view of the torque sensor assembly depicted in FIGS. 25A and 25B.

The second conductive plate 2560 may be referenced to the distal frame portion 2543. For example, as shown in FIG. 26A, the distal frame portion 2543 may include one or more cutouts or recesses 2545*a* and/or 2545*b*. The cutouts may be generally rectangular, square, trapezoidal, or any suitable shape. As shown in FIG. 26C, the second conductive plate 2560 may include one or more tabs 2562*a* and/or 2562*b* that are shaped to interlock and engage in a corresponding and complementary manner (e.g., mechanical key) with the cutouts or recesses 2545*a* and/or 2545*b*, respectively, of the distal frame portion 2543. Accordingly, the second conductive plate 2560 moves in tandem with the distal frame portion 2543, and independently from the proximal frame portion 2542.

Thus, in the variation shown in FIGS. 26A-26C, the first conductive plate 2550 (the more proximal conductive plate relative to the motor 2510 as shown in FIG. 25B) may be referenced to the proximal frame portion 2542, while the second conductive plate 2560 (the more distal conductive plate relative to the motor 2510 as shown in FIG. 25B) may be referenced to the distal frame portion 2544. Accordingly, as the proximal and distal frame portions move in relative torsional motion, the first and second conductive plates also move in relative rotational motion.

Figure 27A:
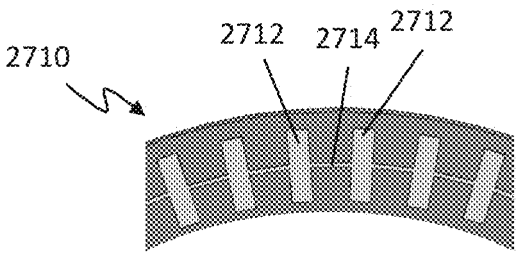
FIGS. 27A and 27B are detailed schematics of conductive regions on a ground conductive plate and an active conductive plate in a torque sensor.
Figure 27B:
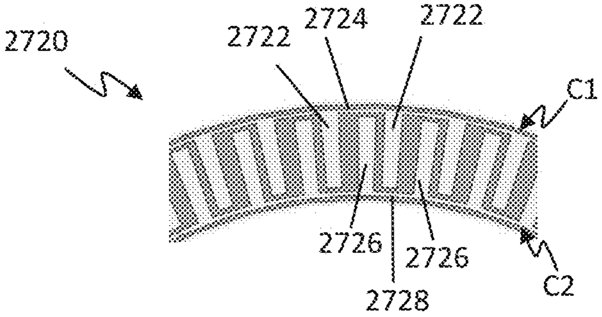

The first and second conductive plates may be generally ring-shaped, but may be any suitable shape. As described above, the first and second conductive plates have facing patterned conductive surfaces. As shown in FIG. 27A, one of the conductive plates may be a "ground" conductive plate 2710 including one or more conductive regions 2712 that are connected via one or more conductive traces 2714, such that the conductive regions 2712 form a common electrical ground. As shown in FIG. 27B, the other conductive plate may be an "active" conductive plate 2720 including a first plurality of conductive regions 2722 and a second plurality of conductive regions 2726. The first plurality of conductive regions 2722 may be conductively coupled with one or more conductive traces 2724 (e.g., an inner ring traversing the inner circumference of the active conductive plate 2720) such that the first plurality of conductive regions 2722 and the traces 2724 form a first signal channel C1. Similarly, the second plurality of conductive regions 2726 may be conductively coupled with one or more conductive traces 2728 (e.g., an outer ring traversing the outer circumference of the active conductive plate 2720) such that the second plurality of conductive regions 2724 and the traces 2728 form a second signal channel C2. The conductive regions 2722 of the first channel C1 may be interleaved with the conductive regions 2726 of the second channel C2. The conductive regions of the ground and active conductive plates are shown are generally linearly-shaped or rectangular (e.g., in the shape of "strips" or "fingers"), though in other variations, the conductive regions may curvilinear (e.g., sine waves or other curved lines) or any suitable shape. The conductive regions on each respective conductive plate may be substantially of the same surface area and arranged in a radially-symmetric manner, which may contribute to capacitance readings that have the same resolution (and thus sensitivity, etc.) regardless of rotational position.

Figure 27C:
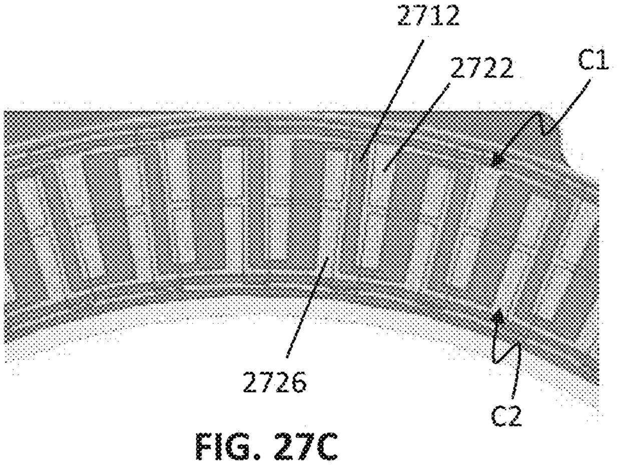
FIG. 27C is a detailed schematic of overlaid conductive regions of the ground and active conductive plates depicted in FIGS. 27A and 27B.

FIG. 27C illustrates how the conductive regions of the ground conductive plate and the active conductive plate may be positioned when the patterned conductive surfaces are facing one another in nominal relative rotational positions. Each of the conductive regions on the ground conductive plate may be facing at least one of the conductive regions on the active conductive plate. For example, the outlined conductive region 2712 of the ground plate may face (or overlap with) at least a portion of a conductive region associated with signal channel C1 (e.g., conductive region 2722) of the active plate and at least a portion of a conductive region associated with signal channel C2 (e.g., conductive region 2726) of the active plate. In some variations, when the torque sensor is in a nominal position (e.g., producing a "zero" torque reading), the conductive region 2712 of the ground plate may face about half of the conductive region 2722 and about half of the conductive region 2726 of the active plate. In the arrangement of facing patterned conductive surfaces, relative rotational movement of ground conductive plate and the active conductive plate causes both a shift in the amount of overlapping area between the "ground" conductive region 2712 and the "active" conductive regions 2722 and 2726, and a shift in which particular conductive regions are overlapping. Accordingly, relative rotation of the ground conductive plate and the active conductive plate may result in difference capacitance signals in the first signal channel C1 and the second signal channel C2. The measurable change in capacitance, or differential capacitance, may be correlated to a measurable change in relative position. In some variations, the measurable change in relative position may be correlated to the change in capacitance signal $c_1$ from the signal channel C1 and capacitance signal $c_2$ from the signal channel C2 according to the differential capacitance relationship of position $\sim(c_1-c_2)/(c_1+c_2)$. In other words, the capacitance values (or changes in capacitance values) may be analyzed to determine direction and magnitude of relative rotational movement between the ground and active conductive plates.

With reference to FIGS. 26A-26C, in some variations, the first conductive plate 2550 (more proximal relative to the motor) may be a ground conductive plate that is registered to the proximal frame portion 2542, and the second conductive plate 2560 (more distal relative to the motor) may be an active conductive plate that is registered to the distal frame portion 2544. Accordingly, as the frame 2540 moves with relative rotational motion between the proximal and distal frame portions (e.g., due to reaction torque as the rotary axis drive actuates), the first and second conductive plates experience relative rotational motion, thereby resulting in measurable differential capacitance between the first and second conductive plates. Signals from the signal channels C1 and C2 on the second conductive plate 2560 may be processed by electronics 2572 on the plate 2560 and/or passed out of the sensor via cable 2572. In other variations, the first conductive plate 2550 may be an active conductive plate and the second conductive plate 2560 may be a ground conductive plate.

Furthermore, in some variations, the torque sensor readings may be calibrated against environmental factors affecting capacitive signals, such as temperature and/or humidity. For example, temperature and/or humidity compensation may be achieved by summing the readings from the two signal channels C1 and C2. Additionally or alternatively, an on-board temperature sensor and/or an on-board humidity sensor may be used to compensate for temperature and/or humidity changes (e.g., according to a known or predetermined calibration curve for the sensor). Furthermore, in some variations, the sensor may additionally or alternatively include one or more reference conductive pads to directly provide at least one signal for calibrating the torque sensor against environment factors.

In some variations, in contrast to the variation shown in FIGS. 26A-26C, the conductive plate that is more proximal (relative to the motor) may be registered to the distal frame portion, while the conductive plate that is more distal (relative to the motor) may be registered to the proximal frame portion. For example, as shown in FIGS. 28A-28D and further described below, a torque sensor 2800 may include a first conductive plate 2850 (more proximal relative to the motor) that is registered to the distal frame portion, and a second conductive plate 2960 (more distal relative to the motor) that is registered to the proximal frame portion via a coupling ring 2880.

Figure 28A:
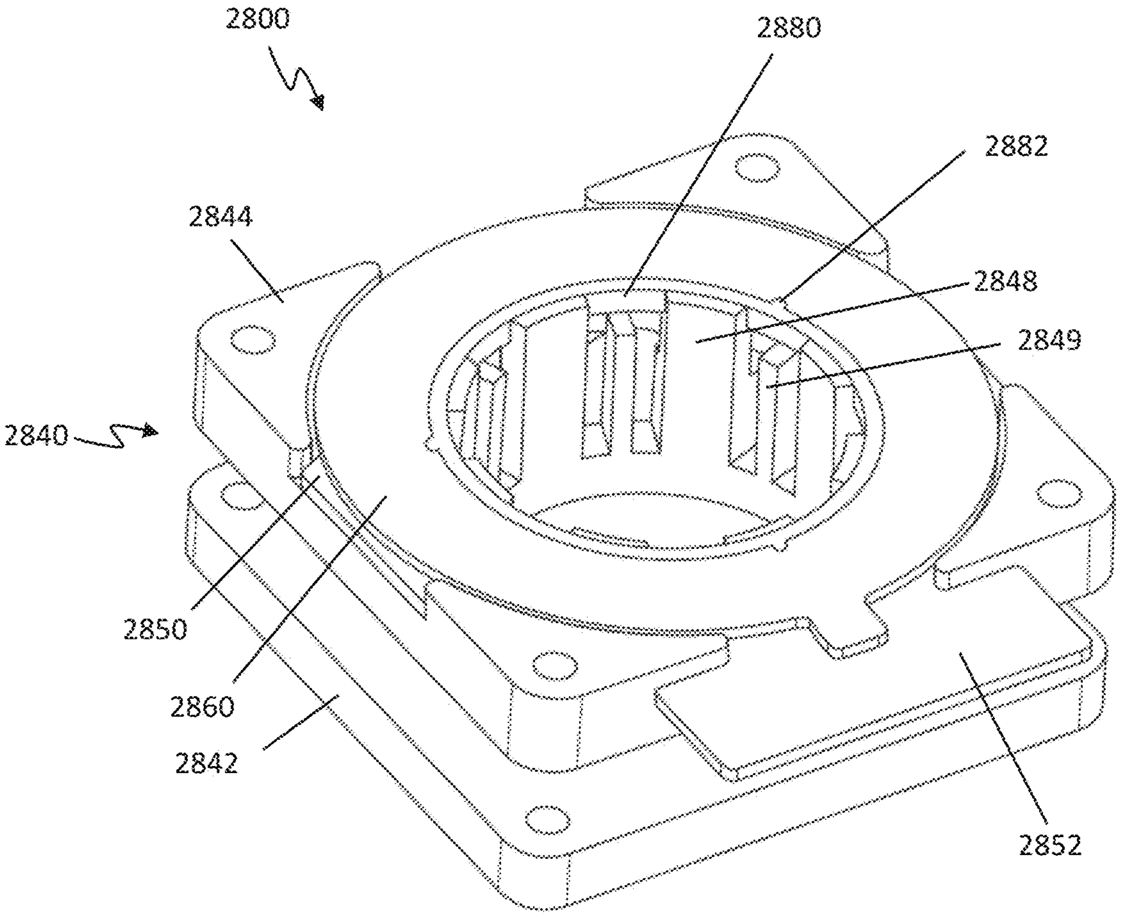
FIG. 28A is a perspective view of another variation of a torque sensor.
Figure 28B:
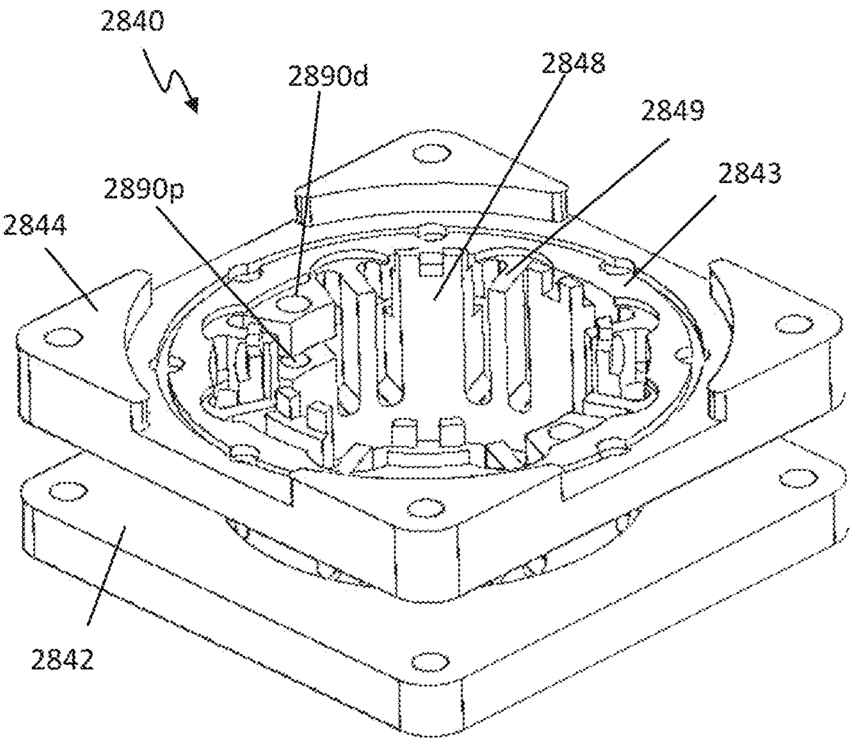
FIG. 28B is a perspective view of a frame in the torque sensor depicted in FIG. 28A.

FIG. 28B illustrates a variation of a frame 2840 that is substantially similar to the frame 2540 described above with reference to FIG. 26A, except as described below. The frame 2840 includes a proximal frame portion 2842 and a distal frame portion 2844, with a plurality of flexure members 2849 and a plurality of anchoring members 2848. The distal frame portion 2844 is configured to couple to the first conductive plate 2850 (more proximal relative to the motor). For example, the first conductive plate 2850 may be configured to rest on a plate mount surface 2843 on the distal frame portion 2844, and may include one or more tabs that interlock and engage with one or more cutouts on the distal frame portion 2844 in a corresponding and complementary manner (e.g., mechanical key), similar to that described above. The proximal frame portion 2842 is configured to couple to the second conductive plate 2860 (more distal relative to the motor). For example, as shown in FIG. 28A, a coupling ring 2880 may couple to anchoring members 2848 (e.g., with epoxy or in another suitable manner) and to the second conductive plate 2860 (e.g., with interlocking parts between the tabs 2882 on the coupling ring and correspond cutouts on the second conductive plate 2860, similar to a mechanical key).

Figure 28C:
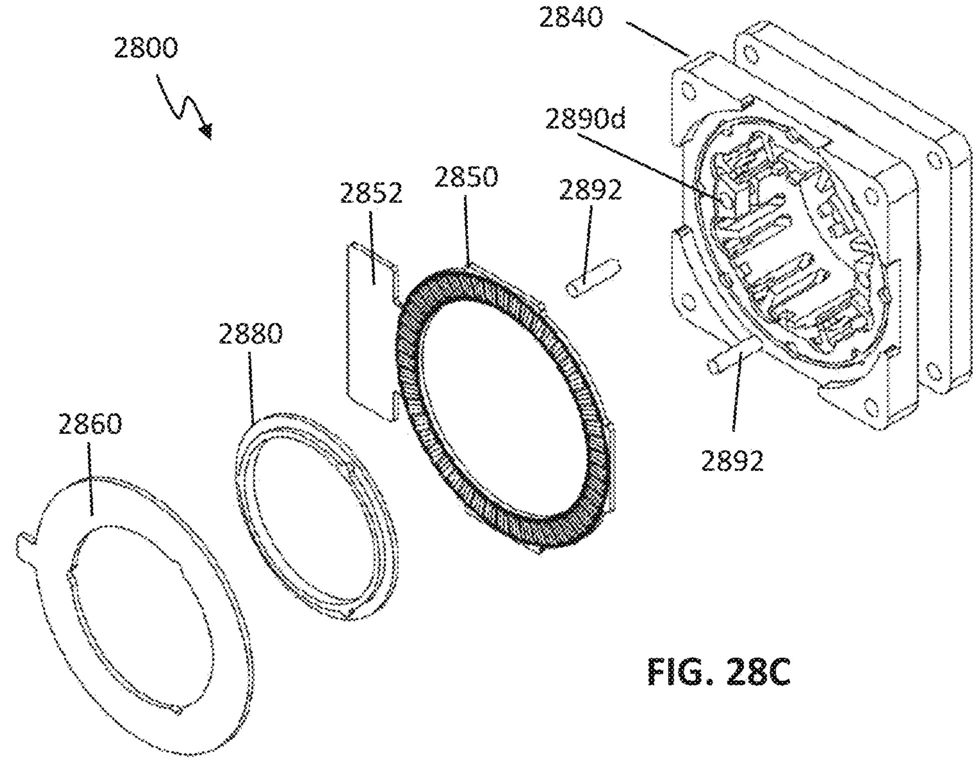
FIGS. 28C and 28D are exploded views of the torque sensor depicted in FIG. 28A.
Figure 28D:
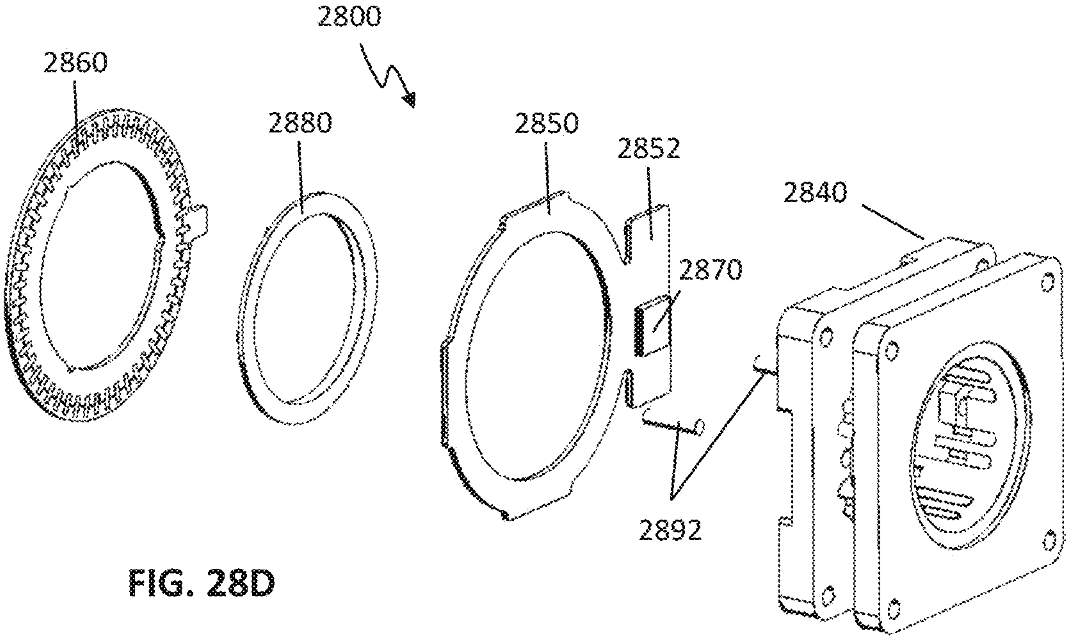

Exploded front and rear perspective views of the torque sensor 2800 are shown in FIGS. 28C and 28D, respectively. Although these figures depict the first conductive plate 2850 as being an active conductive plate (with a mount portion 2852 providing on-board mounting of electronics 2870) and the second conductive plate 2860 as being a ground conductive plate, it should be understood that in other variations, the first conductive plate 2850 may be a ground conductive plate and the second conductive plate 2860 may be an active conductive plate.

In another variation, as shown in FIGS. 23A-23D, a reaction torque sensor 2300 may be integrated into a rotary axis drive for measuring torque on the rotary axis drive output. The torque sensor 2300 may, for example, include a frame 2340, and at least a first conductive plate 2350 and a second conductive plate 2360 adjacent to and facing the first conductive plate 2350 in a similar manner as that described above with reference to FIGS. 27A-27C.

Figure 23A:
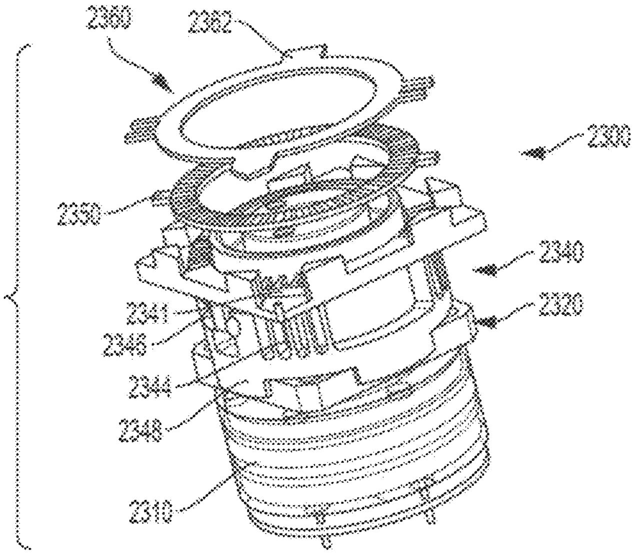
FIG. 23A is an exploded view of one variation of a torque sensor assembly.
Figure 23B:
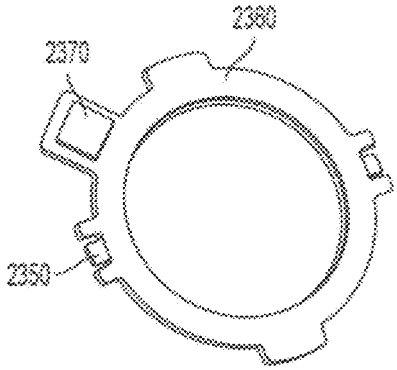
FIG. 23B is a schematic illustration of first and second conductive plates in the torque sensor assembly depicted in FIG. 23A.
Figure 23C:
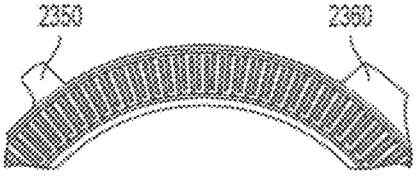
FIG. 23C is a detailed view of the overlap between the first and second plates in the torque sensor assembly depicted in FIG. 23A.
Figure 23D:
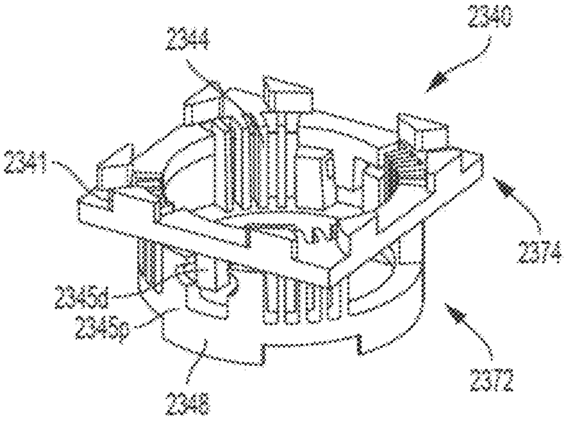
FIG. 23D is a perspective view of a frame in the torque sensor assembly depicted in FIG. 23A.

As shown best in FIG. 23D, the frame 2340 may include a proximal frame portion 2372, a distal frame portion 2374, and a plurality of members 2344 (e.g., longitudinal ribs or other connecting members) connecting the proximal and distal frame portions. The members 2344 preferably provide the frame 2340 with some amount of torsional flexibility such that the frame 2340 acts as a torsional spring. Alternatively, the frame 2340 may omit the members 2344 (e.g., be substantially similar to a sleeve). As shown in FIG. 23A, the frame 2340 may be coupled to a transmission 2320 on a motor assembly 2310 or other portion of the rotary axis drive. For example, the proximal frame portion 2372 may include one or more cutouts defining a recess that interlocks with the external shape of the transmission 2320 (e.g., square, or other suitable polygonal shape), such as with tabs 2348 engaging the square sides of the transmission 2320. Alternatively, the frame 2340 may be coupled to the external surface of the transmission 2320 or other suitable reference structure (e.g., motor housing) in any other suitable manner (e.g., fasteners). On the other end of the frame 2340, the distal frame portion 2374 may be configured to receive the first conductive plate 2350 and the second conductive plate 2360. Generally, the frame 2340 may be made of an electromagnetic shielding material (e.g., aluminum) that helps shield the sensor from noise.

Figure 23E:
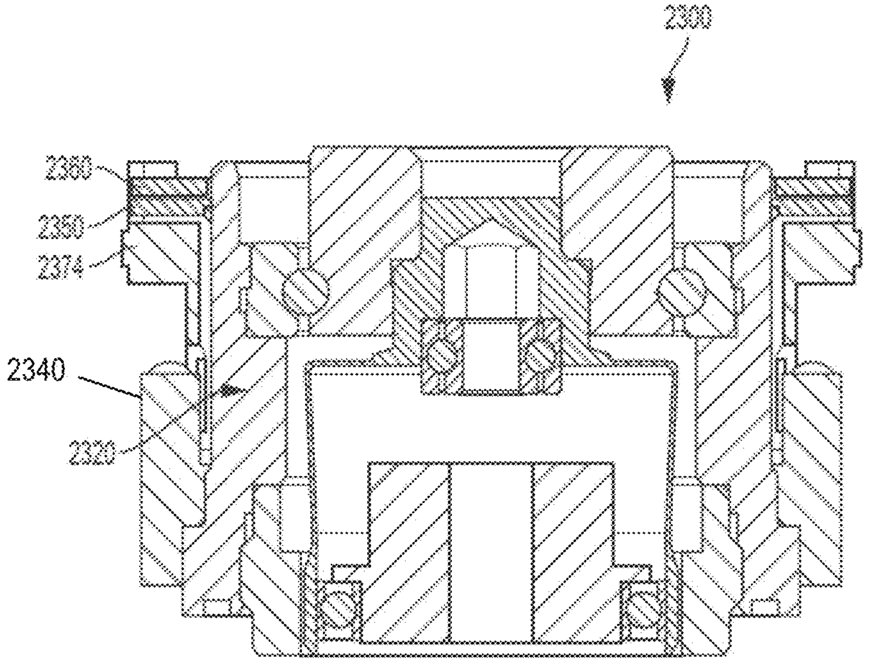
FIGS. 23E and 23F are longitudinal cross-sectional views of two variations of the reaction torque sensor assembly implemented on a rotary axis drive, such as for a tool carriage.
Figure 23F:
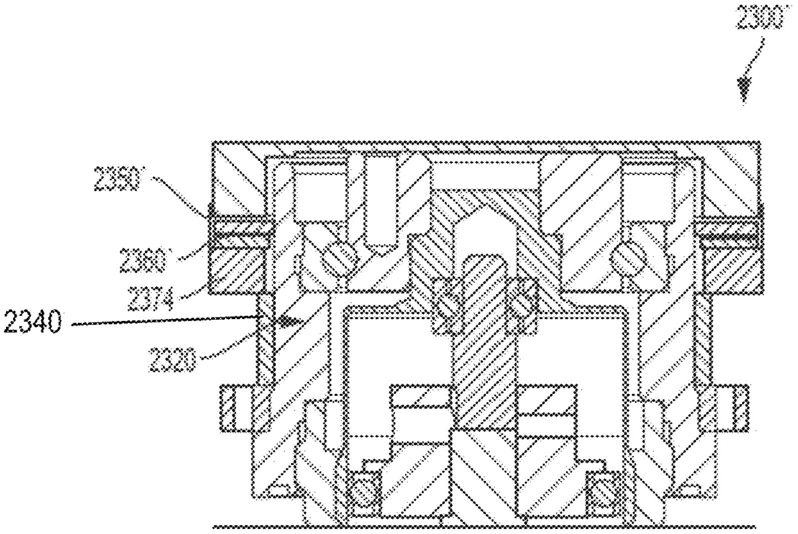

As shown in FIGS. 23A, 23E, and 23F, in some variations, the frame 2340 may "wrap around" or be mounted over the transmission 2320, and the frame 2340 may be sized to have an outer diameter that is no larger (or not significantly larger) than the motor assembly 2310 and a length that is no longer (or not significantly longer) than the transmission 2320. Accordingly, the torque sensor assembly 2300 may advantageously be combined with a motor and transmission assembly in a manner that avoids adding extra length and/or width to the overall package size of the motor and transmission assembly.

As shown in FIGS. 23B and 23C, the first and second conductive plates 2350 and 2360, respectively, may be ring-shaped so as to be arranged around the transmission 2320, and include patterned conductive regions. First and second conductive plates may, for example, be ground and active conductive pads, similar to that described above with reference to FIGS. 27A-27C. The patterned conductive faces, as shown in FIGS. 23A and 23C, may be adjacent and facing one another when received in the frame 2340. The first and second conductive plates 2350 and 2360 may be arranged in either order on the frame 240. For example, as shown in FIG. 23E, the first conductive plate 2350 may be more proximal on the torque sensor assembly 2300 than the second conductive plate 2360. Alternatively, as shown in FIG. 23F, the first conductive plate 2350' may be more distal on the torque sensor assembly 2300' than the second conductive plate 2360'.

The first conductive plate 2350 may be configured to couple to an external surface of the transmission, while the second conductive plate 2360 may be configured to fixedly engage with the distal frame portion 2374. For example, as shown in FIG. 23E, the first conductive plate 2350 may be coupled to an external surface of the transmission 2320 (e.g., at a distal end of the transmission 2320) such that the first conductive plate 2350 rotates (if at all) with the portion of the transmission 2320 to which it is attached. Additionally, in this example, the second conductive plate 2360 may be fixedly engaged with the distal frame portion 2374, such as with radially extending tabs 2362 that complementarily engage with cutouts 2341 on the distal frame portion 2374. Alternatively, the first conductive plate 2350 and the second conductive plate 2360 may be coupled to the transmission 2320 and the distal frame portion 2374, respectively, with epoxy, other fasteners, or other suitable method to enable the first conductive plate 2350 to move with the transmission 2320 and the second conductive plate 2360 to move with the distal frame portion 2374.

As a result of the mounting arrangement of the first and second conductive plates, generally, the first conductive plate 2350 may be free to rotate relative to the distal frame portion 2374, while the second conductive plate 2360 does not rotate relative to the distal frame portion 2374. Accordingly, the first conductive plate 2350 may rotate relative to the second conductive plate 2360. Sensor electronics 2370 mounted on, or otherwise coupled to, one of the conductive plates may provide differential measurement of the capacitance between the first and second conductive plates 2350 and 2360. The degree of relative rotation of the conductive plates may be inferred from the differential measurement of the capacitance, and subsequently mapped to a measurement of reaction torque experienced by the frame 2340. For example, when the sensor assembly is mounted on a rotary axis drive assembly of a motor assembly 2310 and transmission 2320 (e.g., as shown in FIGS. 23A, 23E, and 23F) as described above, the sensor assembly may provide a measurement of reaction torque experienced by the rotary axis drive, as reflected by the relative rotation of (i) second conductive plate 2360 and the distal frame portion 2374 and (ii) the first conductive plate 2350, the proximal frame portion 2372, and the transmission 2320 or other reference portion of the rotary axis drive.

Other variations of above-described components (e.g., conductive pads) and other components may be combined with different variations of sensor frames, etc. described herein in any suitable combination.

Figure 29A:
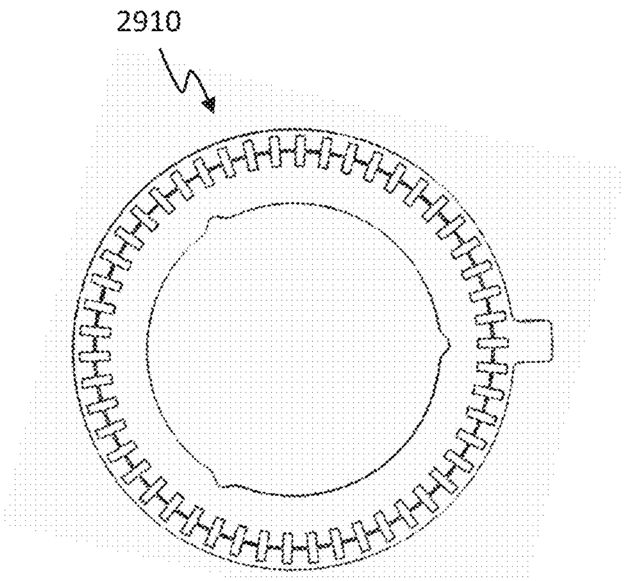
FIGS. 29A and 29B are overall and detailed views of one variation of a ground conductive plate in a torque sensor.
Figure 29B:
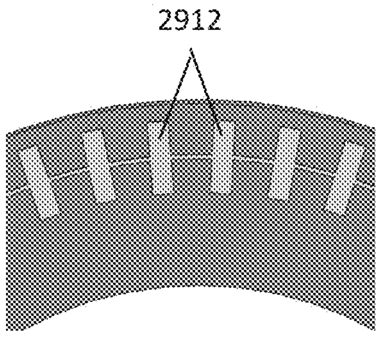
Figure 30A:
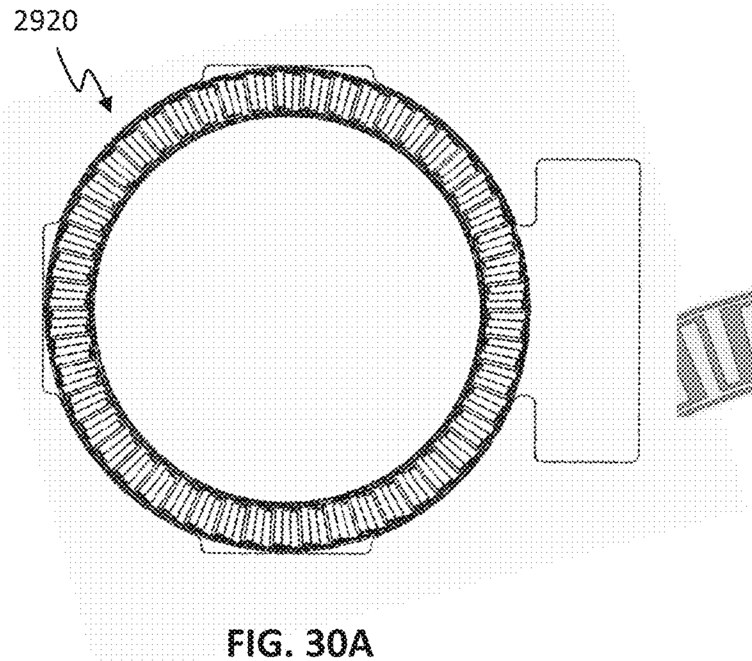
FIGS. 30A and 30B are overall and detailed views of one variation of an active conductive plate in a torque sensor.
Figure 30B:
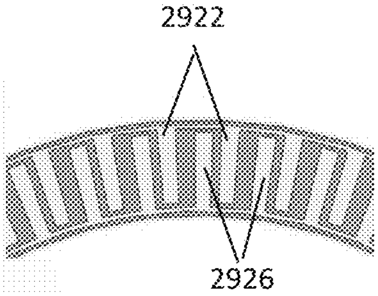

For example, FIGS. 29A and 29B illustrate overall and detailed views of one variation of a ground conductive pad 2910, and FIGS. 30A and 30B illustrate overall and detailed views of one variation of an active conductive pad 2920. Different geometric parameters may be adjusted, for example, to reduce undesirable parasitic capacitance or other edge effects, and thus reduce noise and/or improve sensitivity. For example, generally, the distance between conductive regions may be increased to reduce parasitic capacitance. For example, distance between the conductive regions 2712 on the ground conductive plate 2910 may be increased to a suitable separation distance.

Figure 31A:
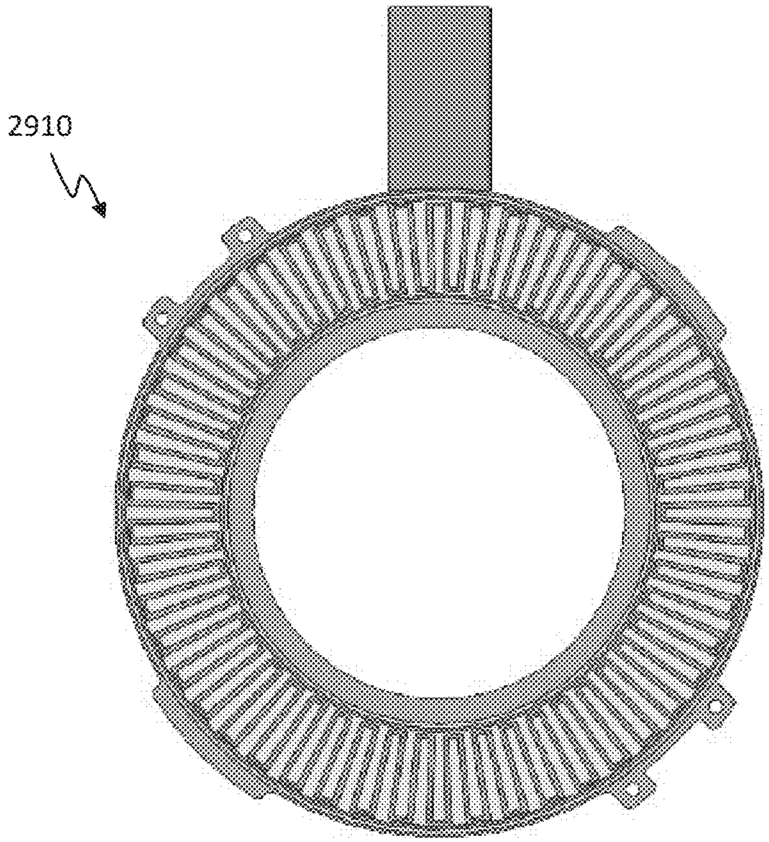
FIGS. 31A and 31B are overall and detailed views of another variation of an active conductive plate in a torque sensor.
Figure 31B:
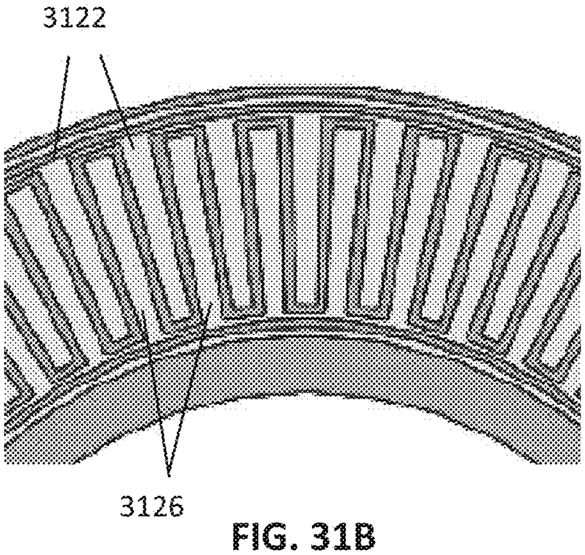

Furthermore, generally, larger conductive regions may experience reduced edge effects. For example, FIGS. 31A and 31B illustrate overall and detailed views of another variation of an active conductive pad. Wider and/or longer conductive regions 3122 (forming a first signal channel) and conductive regions 3126 (forming a second signal channel) provide greater capacitive area and thus may achieve improved performance for the torque sensor with less noise.

Figure 33A:
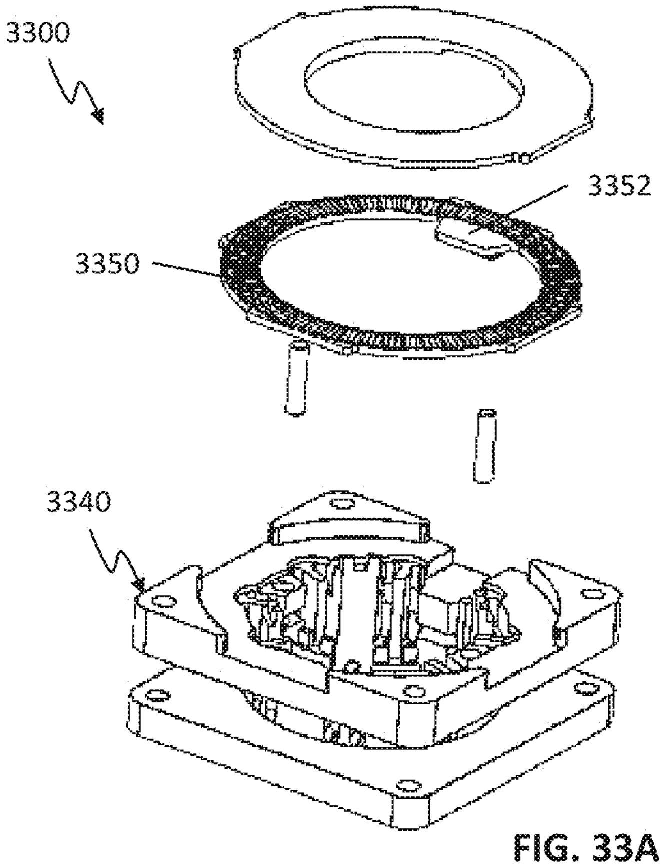
FIGS. 33A and 33B are exploded views of another variation of a torque sensor with a radially inward-projecting electronics mount portion.
Figure 33B:
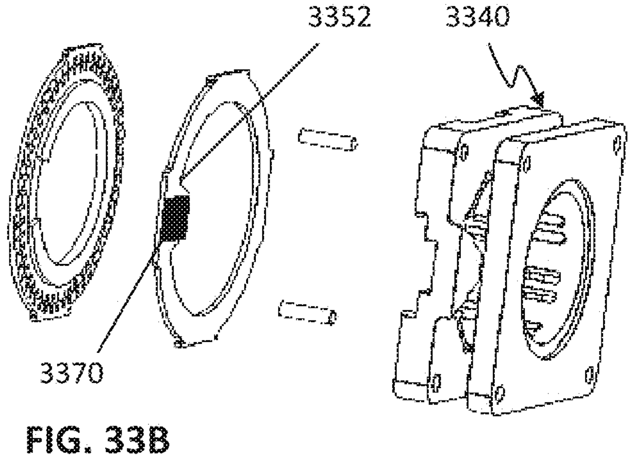

Additionally or alternatively, the geometry and/or dimensions of at least some parts of the conductive plates may be selected to further modify the overall volume occupied by the torque sensor. For example, the conductive board 2850 shown in the variation of FIG. 28A includes an electronics mount portion 2852 that extends radially outward from the footprint or envelope of the frame 2840. In another variation as shown in FIGS. 32A and 32B, the conductive board 3250 may be similar to the conductive board 2850 except that its electronics mount portion 3252 (with electronics 3270 disposed thereon) is oriented orthogonal to the rest of the conductive board 3250, thereby reducing the overall envelope of volume occupied by the torque sensor 3200. In yet another variation, as shown in FIGS. 33A and 33B, the conductive board 3350 may be similar to the conductive board 2850 except that its electronics mount portion 3352 (with electronics 3370 disposed thereon) extends radially inward, thereby keeping the electronics mount portion 3352 within the overall footprint or envelope of the frame 3340 (and reducing the overall envelope of volume occupied by the torque sensor 3300). Alternatively, in some variations, the electronics may be disposed on the ring portion of a conductive board (e.g., electronics 2570 on conductive board 2550 as shown in FIG. 26C).

Additionally or alternatively, in some variations, the torque sensor may further include one or more stopper mechanisms that limits the extent of twisting that the frame may undergo, thereby preventing excessive torqueing of the sensor assembly that may damage the sensor. The stopper mechanism may be a mechanical stopper. For example, as shown in FIG. 23A, the frame 2340 may include at least one ball 2346 (e.g., steel or other suitable metal or non-compliant plastic, etc.) disposed between a member 2345*d* (labeled in FIG. 23D for clarity) extending from the distal frame portion 2374 and at least one member 2345*p* (labeled in FIG. 23D for clarity) extending from the proximal frame portion 2372, where the members 2345*d* and 2345*p* move toward each other when the frame 2340 is twisted or torqued. The ball 2346 may be sized to provide physical interference between the members 2345*d* and 2345*p*, thereby limiting the amount of twisting that the frame 2340 may undergo. Any suitable number of balls 2346 or similar pins may be included. In other variations, a U-shaped piece or stopper of other suitable shape may be interspersed between features of the distal frame portion 2374 and features of the proximal frame portion 2372 for physically limiting the extent of possible torque of the frame 2340.

As another example of a mechanical stopper mechanism, one of the proximal and distal frame portions may include an anchoring hole and the other of the proximal and distal frame portions may include a clearance hole. For example, as shown in FIG. 28B, the proximal frame portion 2842 may include one or more anchoring holes 2890*p* each sized to receive and couple to a pin, such as via press fit or other interference fit, epoxy, etc. The distal frame portion 2844 may include one or more clearance holes 2890*d* each nominally (e.g., in a sensor rest state) aligned with a respective anchoring hole. The clearance holes may be slightly larger in diameter than the pin, so as to permit some twisting of the frame 2840, but provide physical interference between the pin and side wall of the clearance hole in the event of frame twist of a certain degree, thereby limiting the amount of twisting that the frame 2340 may undergo. As shown in FIGS. 29C and 29D, the torque sensor may include two pins 2892 on opposite sides of the frame 2840 (e.g., equally distributed around the sensor so provide balanced load in the event of over-torqueing). However, it should be understand that the torque sensor may include more or fewer pins 2892.

Capacitive Rotary Encoder

Figure 22A:
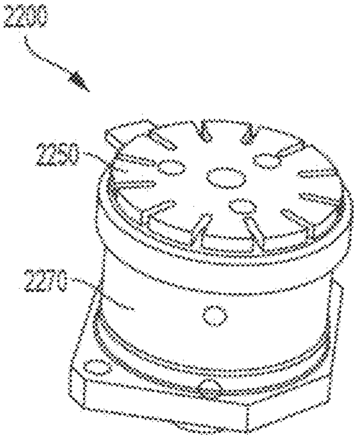
FIGS. 22A and 22B are perspective assembly and exploded views, respectively, of a capacitive absolute rotary encoder.
Figure 22C:
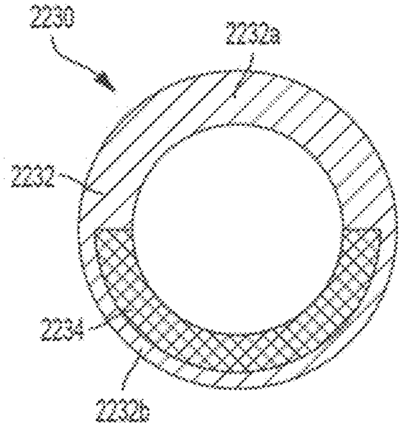
FIGS. 22C and 22D are examples of conductive plates in the encoder depicted in FIGS. 22A and 22B.
Figure 22B:
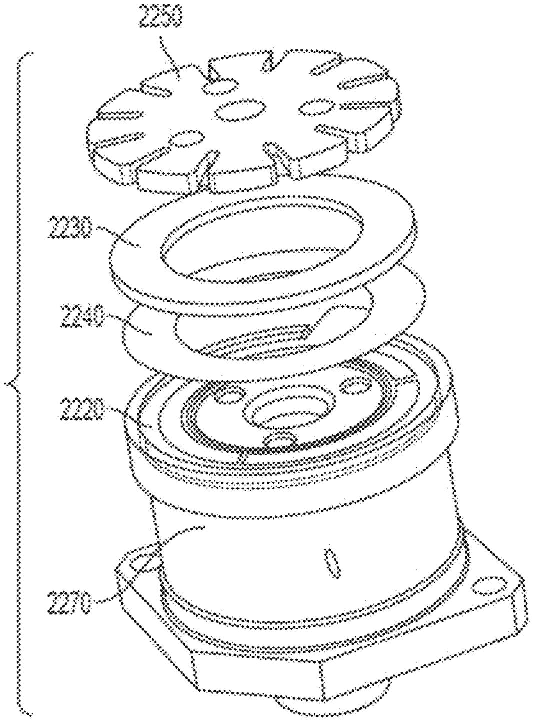
Figure 22D:
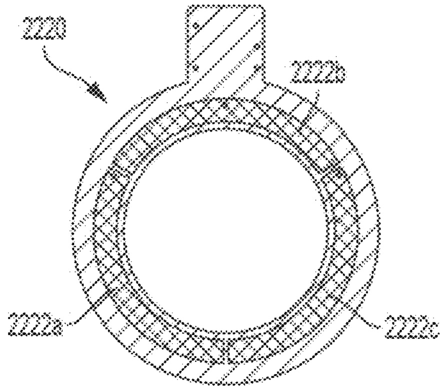

In some variations, one or more rotary axis drives may include a capacitive absolute rotary encoder assembly for determining the rotational position of the motor output. For example, as shown in FIG. 22A, the encoder assembly 2200 may be disposed at the distal output of a gear transmission 2270 (e.g., harmonic, planetary, etc.), or alternatively the output of a motor assembly (without a transmission). As shown in FIGS. 22B-22D, the encoder assembly 2200 may include a first conductive plate 2220 with at least three conductive regions 2222*a*, 2222*b*, and 2222*c* radially distributed around the first conductive plate 2220 and a second conductive plate 2230 having a conductive region 2232 and a ground region 2234.

For example, in one variation, the first and second conductive plates may be generally annular plates. The three conductive regions 2222*a*, 2222*b*, and 2222*c* may be equally distributed around the first conductive plate 2220. The conductive region 2232 on the second conductive plate 2230 may be generally arcuate, with a semi-circular measurement region 2232*a*. However, the measurement region 2232*a* may be any suitable shape covering a portion of the second conductive plate. The two ends of the semi-circular measurement region 2232*a* may be connected by a peripheral capacitive strip 2232*b*, or other capacitive region.

As shown in FIG. 22B, the first conductive plate 2220 may be configured to be fixedly coupled to a reference point (e.g., housing or other exterior surface of the transmission 2270, or a structure coupled to the housing or other exterior surface of the transmission 2270), with the conductive regions 2222*a-c* facing outward. The second conductive plate 2230 may be axially aligned with the first conductive plate 2220, with the conductive region 2232 and ground region 2234 facing the conductive regions 2222*a-c* of the first conductive plate 2220. The second conductive plate 2230 may be fixedly coupled to the rotary output of the transmission 2270 such that the second conductive plate 2230 rotates with the output of the transmission 2270. For example, the second conductive plate 2230 may couple to a top plate 2250 (e.g., with fasteners, epoxy, etc.) that is mounted to the rotary output of a transmission 2270 (or alternatively, directly to a rotary output of a motor assembly, or to a dummy gear coupled to the rotary output of a motor assembly, etc.), such as with fasteners.

Figure 22E:
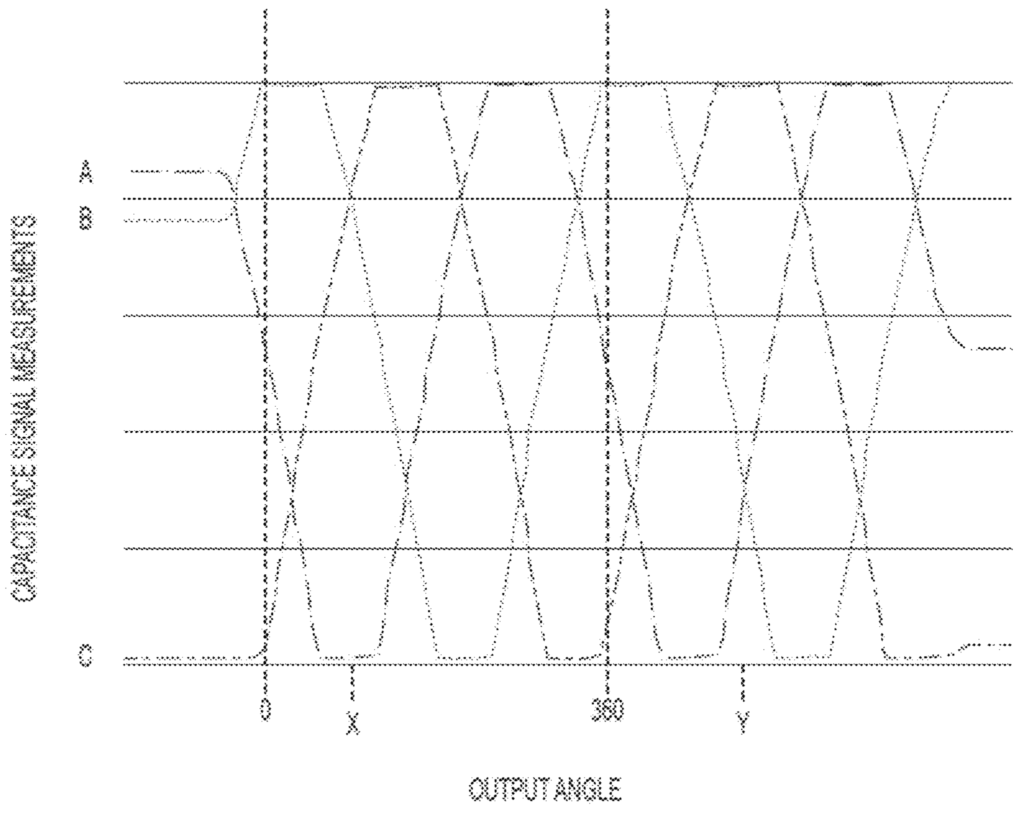
FIG. 22E is a plot of capacitive signals mapped to output angle for one exemplary variation of the encoder depicted in FIGS. 22A and 22B.

As a result of the mounting arrangement of the first and second conductive plates 2220 and 2230, the second conductive plate 2230 may rotate (with the rotary output of the transmission 2270) relative to the first conductive plate 2220. As this relative rotation occurs, different combinations of the conductive regions 2222*a*, 2222*b*, and 2222*c* on the first conductive plate 2220 are overlapped with the measurement region 2232*a* on the second conductive plate 2230, and to different extents. Generally, the set of capacitive measurements from each conductive region 2222*a*, 2222*b*, and 2222*c* may be used to determine the angular orientation of the second conductive plate 2230 relative to the first conductive plate 2220, which provides a determination of the angular position of the output of the transmission 2270. For example, FIG. 22E shows a plot of signals from each of three conductive regions: signal A corresponding to a conductive region 2222*a*, signal B corresponding to a conductive region 2222*b*, and signal C corresponding to a conductive region 2222*c*. A second conductive plate 2230 having a generally semi-circular measurement region 2232*a* may rotate relative to the first conductive plate 2220 in the same direction. For each angular position of the second conductive plate 2230 relative to the first conductive plate 2220, there is a unique combination of areas of overlapping conductive regions between the first and second conductive plates. For example, as shown in FIG. 22E, at output angular position X, signal A is about zero (suggesting no overlap between the conductive region 2222*a* and the measurement region 2232*a*), and signals B and Care about 80% of maximum signal (suggesting about 80% of each of conductive region 2222*b* and conductive region 2222*c* are overlapped with measurement region 2232*a*). As another example, at output angular position Y, signal C is at about maximum signal (suggesting the entirety of conductive region 2222*c* is overlapped with measurement region 2232*a*), and signals A and B are about 30% of maximum signal (suggesting about 30% of each of conductive region 2222*a* and conductive region 2222*b* are overlapped with measurement region 2232*a*). The signals A, B, and C may be mapped to a unique absolute output angle according to the plot in FIG. 22E for this exemplary set of first and second conductive plates 2220 and 2230. For other variations of first and second conductive plates with different numbers and shapes of capacitive regions, different plots may be generated but utilized in the same manner to determine relative orientation of the first and second conductive plates (and thus output angle of the transmission, when the second conductive plate is coupled to the transmission output).

In some variations, the first conductive plate 2220 may include at least three conductive regions 2222*a-c* in combination with the second conductive plate 2230 having a semi-circular measurement region 2232*a*. If the first conductive plate 2220 includes only two conductive regions, its bilateral symmetry results in a non-unique mapping between capacitive signal measurements and output angle; that is, there may be two possible output angles for each possible combination of signal measurements. However, three conductive regions permits a unique mapping (i.e., 1:1) between sets of capacitive signal measurements and output angles. In some variations, more than three conductive regions may be included in the first conductive plate 2220. Furthermore, the size and shape of the conductive regions on the first conductive plate 2220 may vary suitably depending on the size and shape of the measurement region 2232*a* on the second conductive plate 2230.

Furthermore, in some variations, a bearing 2240 may be interspersed between the first conductive plate 2220 and the second conductive plate 2230 to reduce friction between the relatively rotating first and second conductive plates. As shown in FIG. 22B, for example, the bearing 2240 may be a thin, annular-shaped sheet made of a suitable bearing material. For example, the bearing 2240 may be made of a material (e.g., polytetrafluoroethylene, or TEFLON) that is low-friction and does not interfere with the capacitance measurement between the first and second conductive plates. The bearing 2240 may further be made of a material that is lightweight and durable against wear and tear.

Accordingly, generally, the capacitive absolute rotary encoder 2200 described above may be used in combination with a rotary axis drive in a tool carriage or other suitable motor or transmission assembly, to measure rotational output position. The encoder 2200 is low-profile and compact, such that may not contribute additional height or length to a motor or transmission assembly. Accordingly, the capacitive absolute rotary encoder 2200 may advantageously be combined with a motor and transmission assembly in a manner that avoids adding extra length and/or width to the overall package size of the motor and transmission assembly. Furthermore, the capacitive absolute rotary encoder 2200 may advantageously be made of a relatively low number of parts, thereby facilitating simple manufacturing and assembly. In applications described herein, the capacitive absolute rotary encoder 2200 may be easy to mount directly to a geared transmission (e.g., with top plate 2250, etc.).

Combined Reaction Torque Sensor and Capacitive Rotary Encoder

Figure 24A:
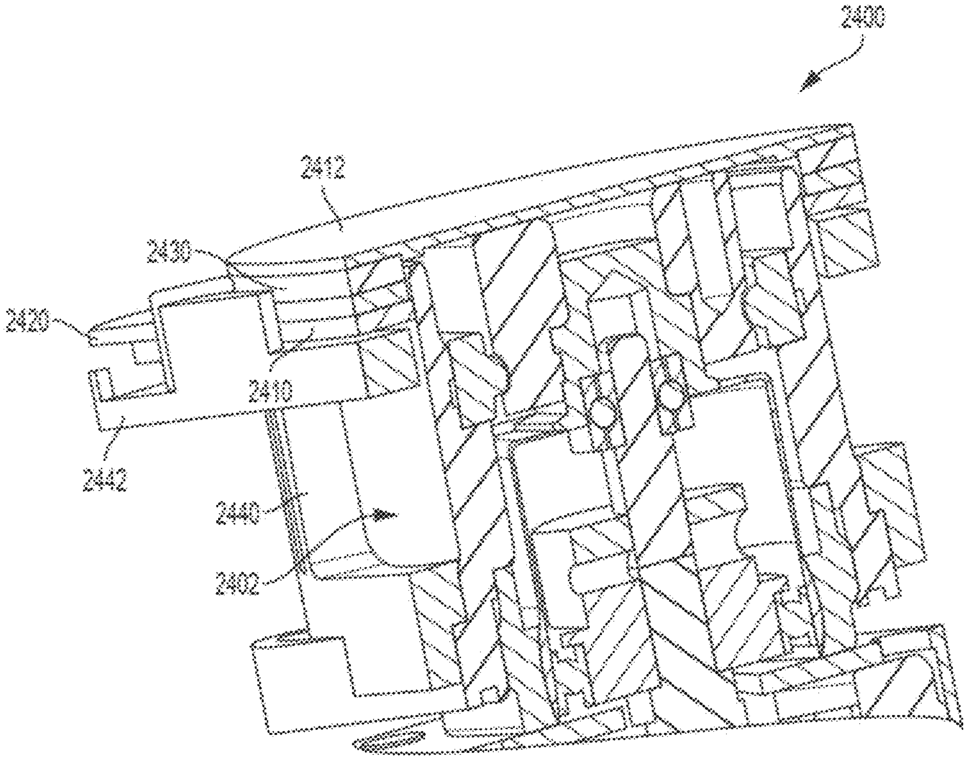
FIG. 24A is a perspective longitudinal cross-sectional view of a combined sensor assembly including one variation of a reaction torque assembly combined with one variation of a capacitive absolute rotary encoder.
Figure 24B:
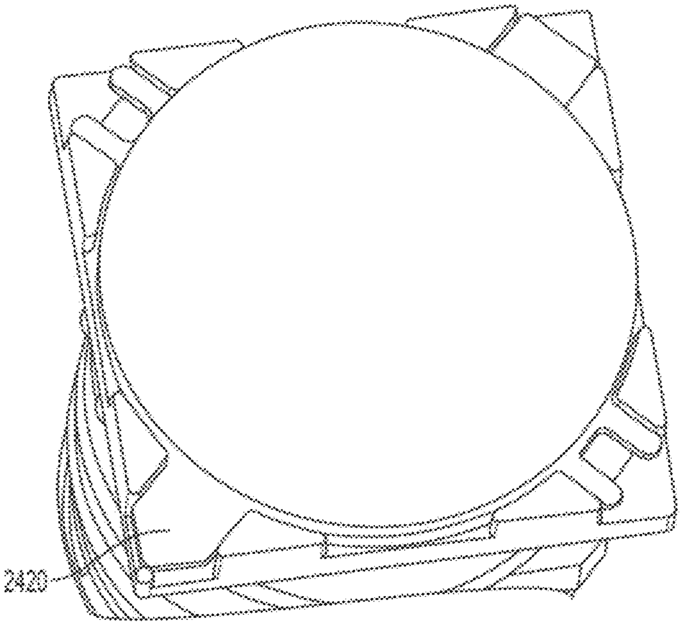
FIG. 24B is a top view of the combined sensor assembly depicted in FIG. 24A.

In some variations, the above-described reaction torque sensor assembly 2300 and the capacitive absolute rotary encoder 2200 may be combined on a rotary axis drive or other motor or transmission assembly. For example, as shown in FIGS. 24A and 24B, components of the reaction torque assembly 2300 and the capacitive absolute rotary encoder 2200 may be stacked together and mounted on a transmission 2402. A frame 2440 with a distal frame portion 2442 may be coupled to the transmission 2402 (similar to frame 2340 described with reference to FIGS. 23A-23F). A first capacitive plate 2410 is disposed in the distal frame portion 2442 and coupled to the exterior surface of the transmission 2402 (similar to first capacitive plate 2350 described with reference to FIGS. 23A-23F). A second capacitive plate 2420 is fixedly engaged with the distal frame portion 2442 (similar to second capacitive plate 2360 described with reference to FIGS. 23A-23F) and is configured with conductive regions (similar to first conductive plate 2220 described with reference to FIGS. 22A-22E). A third capacitive plate 2430 (similar to second conductive plate 2230 described with reference to FIGS. 22A-22E) is coupled to the output of the transmission 2402, such as via mounting plate 2412. Accordingly, the conductive plates 2410 and 2420 may function in combination similar to the reaction torque assembly 2300 described above, while the conductive plates 2420 and 2430 may function in combination similar to the capacitive absolute rotary encoder 2200 described above. As such, the conductive plate 2420 may be a common active board that is shared between the torque sensor assembly and the capacitive absolute rotary encoder.

Furthermore, generally, a rotary encoder (e.g., the capacitive absolute rotary encoder 2200 described above) may be used to measure output position of a motor assembly or transmission coupled to a motor assembly, in combination with another rotary encoder used to measure input position of the motor assembly (e.g., at the rotor). In such variations, the input encoder may in some circumstances be used to compensate for errors from the output encoder (or uncertainty due to a lower resolution of the output encoder, etc.). For example, the input encoder may have a higher resolution than the output encoder. If the output encoder reports an erroneous measurement, the input encoder may be used to determine an output position (due to known gear ratios, etc. in the motor and transmission assembly) as long as the output encoder error is within one rotation of the motor.

Although variations of the linear axis drives, rotary axis drives, sensors, and other components are described above with respect to either a combined axis drive carriage variation or a rotary axis drive carriage variation, it should be understood that other variations of the tool carriage are possible by combining any one or more of the above-described linear axis drives with any one or more of the above-described rotary axis drives to achieve a suitable set of axis drives for actuating a surgical tool or instrument, and/or any of the above-described sensors or other components. For example, any of the rotary axis drives discussed above with respect to the combined axis drive carriage variation may be utilized in a rotary axis drive carriage variation, and vice versa. Furthermore, any of the sensors described above (e.g., encoders, torque sensors, etc.) may be used in any suitable combination with any of the linear axis drive or rotary axis drive variations discussed herein.

Controls

Generally, commands may be provided to the various drives in the tool driver (e.g., actuation of linear or rotary axis drives in the carriage, actuation of the tool carriage on the base, etc.) via software to control movement of a surgical tool coupled to the tool driver and the tool's end effector. In some variations, the software may further control the tool driver to compensate for physical changes in the components of the tool driver and/or tool. For example, as the tool driver actuates a surgical tool shaft to rotate around a longitudinal axis by driving a cable inside the tool shaft, the length of the cable inside the tool shaft changes (e.g., shortens). This change in length may cause a change in the tension force that the cable experiences, thereby putting unnecessary wear and tear on the cable. To compensate for this change in cable length, a tool driver control system may command the relevant motor drives to rotate in a direction corresponding to increasing cable slack or cable length, thereby releasing tension when the tool shaft is axially rolled around a rotation axis. Accordingly, throughout rotation of the tool shaft, a tool driver control system may maintain a substantially constant tension on each driven cable.

Furthermore, in some variations, the tool driver may utilize a known reference or "home" configuration or position of an end effector (of a tool attached to the tool driver), such as to enable calibration of the tool and/or to permit the robotic system to track the configuration or position of the end effector (e.g., the extent to which jaws are closed or open, the angle of a knife blade, etc.). For example, in one variation, the tool driver may include position sensors (e.g., absolute position encoders) on the drive cables running from the actuated drives (e.g., linear or rotary axis drives), where a reference or "home" position may be saved upon startup (e.g., power on) or calibration of the system, after sterilization of the tool driver (e.g., in an autoclave), or during any suitable phase of use of the tool driver. The position sensors may track position of the cables relative to the reference position. Alternatively, upon startup or calibration, the cables may be driven to a pre-saved reference position of the cables (e.g., stored in persistent memory), or in some variations, a modified or updated pre-saved reference position to compensate for slippage or creep over time as the cable relax with use and strain.

As another example, one or more sensors (e.g., capacitive, distance, etc.) may be disposed on a surface of the cannula of the tool driver such that when the tool is inserted in the cannula and the drive cable is tightened beyond the point of removing cable slack, the one or more sensors detect contact occurring between at least a portion of the tool and the surface of the cannula. For example, after cable slack is removed, further movement of the cable may induce the end effector or other inserted portion of the tool to move within the cannula and contact an interior surface of the cannula. A sensor disposed on the contacted interior surface of the cannula may detect this contact and save the current tool configuration as a reference or "home" configuration from which to track future positions of the cable and end effector.

As another example, pulleys directing cables from the tool driver (e.g., within a surgical tool) may be radially asymmetrical (e.g., non-circular) so as to enable a specific mapping between cable position or force and the resulting end effector pose. For example, given a known position and/or set of forces on a driving cable, the mapping based on one or more pulleys may be used to calculate the corresponding pose of the end effector of the tool.

Furthermore, the system may save a reference position for each of a plurality of uses, which may provide information on which to base expectations for future performance. For example, if a current detected reference position is significantly different from an average of previously detected and stored reference positions, then the system may generate an alert or warning that the tool driver and/or tool is not operating as expected (e.g., indicate the need for calibration or replacement of the tool driver and/or tool). As another example, a set of previous stored reference positions may be used to determine an expected pattern of wear and tear (e.g., normal range of creep of cables) in the tool driver and/or tool, and if a current detected reference position significant deviates from the expected pattern, then the system may generate a warning and/or evaluate the data and provide suggestions for repair and other methods of correction or compensation.

Wireless Communication

In some variations, the tool driver may include a wireless connection for power and/or signal communication to and from various components of the tool drive. Wireless connections may be desirable, for example, when the tool driver is used for robotic surgery because surgical procedures generally require a sterile environment, and wireless connections may reduce or eliminate the need for finding a sterile way to use physical, wired connections to power and/or communicate signals to and from the tool driver system. For example, wireless interfaces may be useful or desirable in surgical and other environments in which fluid, contaminants, or biological, chemical, and/or radiological agents may be found.

Figure 21A:
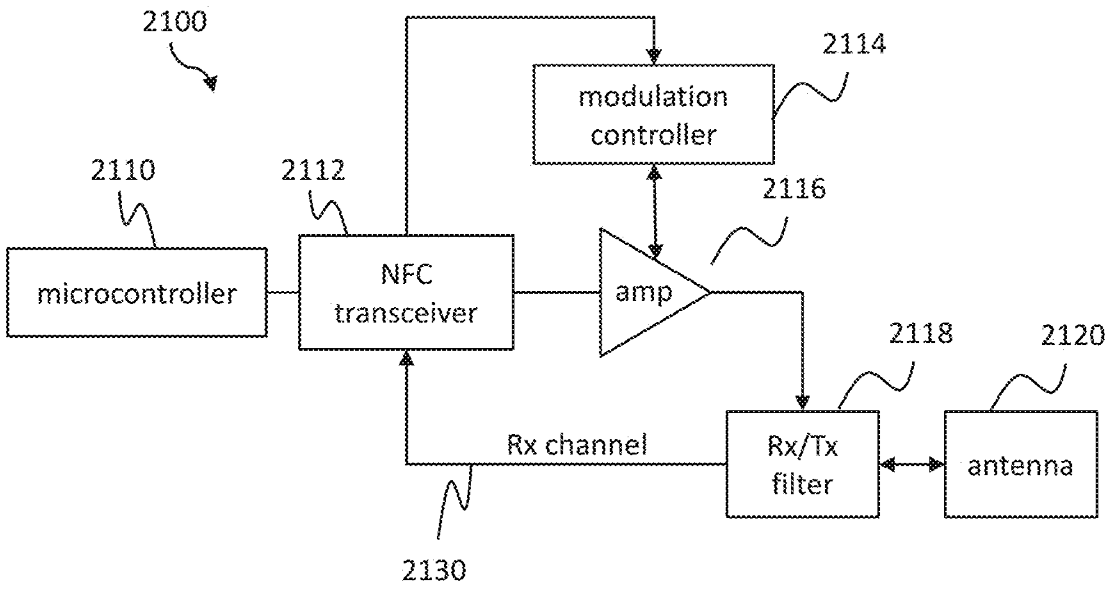
FIG. 21A is a schematic illustration of a wireless tool driver interface.

For example, as shown in FIG. 21A, a tool driver wireless interface 2100 may be provided for transferring power and/or signal communications to and from the tool driver. A microcontroller 2110 or microprocessor (e.g., located in a robotic arm to which the tool driver is attached, or other suitable control center) may be configured to generate and control signals. The signals may be communicated to a near-field communication (NFC) transceiver 2112 that is coupled to the microcontroller 2110. The electrical signals may flow from the NFC transceiver 2112 to a modulation controller 2114 and/or amplifier 2116 for conditioning the signals. Thereafter, the signals and power may flow from the amplifier 2116 to a receive (Rx) and transmit (Tx) filter 2118, and then to one or more antennas 2120 located on the tool driver. For example, as shown in FIG. 4B depicting one variation of a combined linear and rotary axis drive carriage, the carriage may include a wireless antenna PCB 482 near the rotary axis drives 430*a* and 430*b*, or any suitable location on the tool carriage. As another example, as shown in FIG. 10C depicting one variation of a rotary axis drive carriage, the carriage may include a wireless antenna PCB 1090 located in a PCB slot 1016 in the housing body 1012, or any suitable location on the tool carriage. Furthermore, there may also be provided an Rx channel 2130 from the Rx/Tx filter traveling back to the NFC transceiver 2112. In some variations, at least some portions of these communications (e.g., between the Rx/Tx filter 2118 and the antenna 2120) may be wired with a physical connection.

Figure 21B:
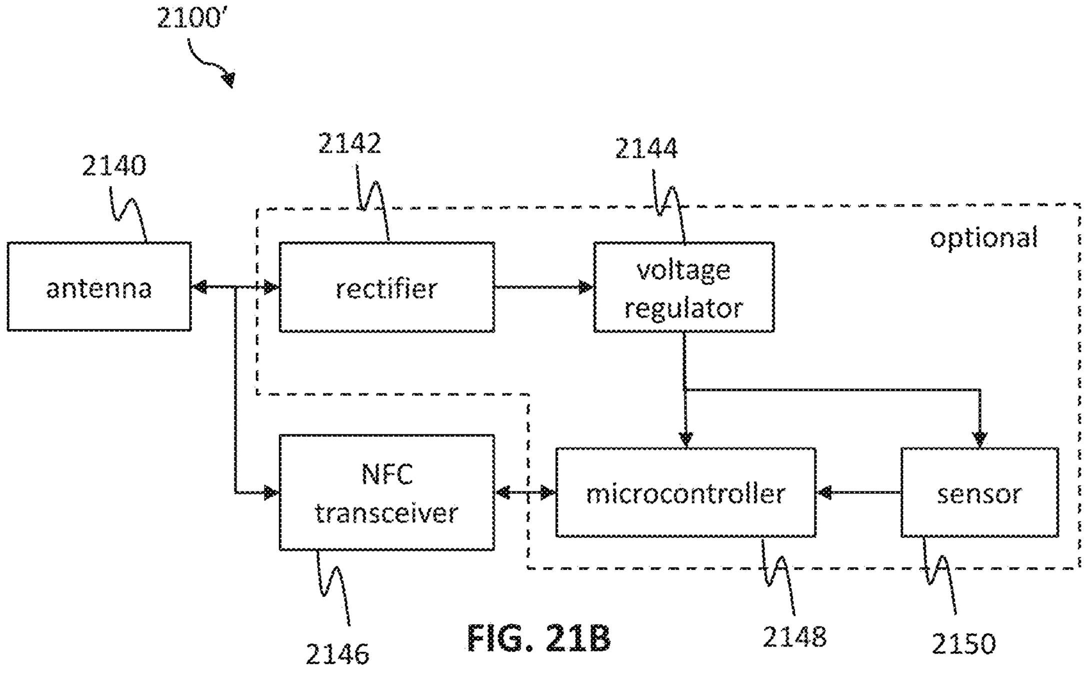
FIG. 21B is a schematic illustration of a wireless tool interface.

As another example, a surgical tool engaged with the tool driver may utilize a wireless connection scheme 2100' with a tool antenna 2140 to communicate through a wireless communication protocol with an antenna in a robotic arm (or other supporting system used in conjunction with the tool driver). Such a tool may be in mechanical connection with a distal end of a robotic arm, but lack a physical electronic plug or other connection. Instead, as shown in FIG. 21B for example, the tool antenna 2140 may connect electronically to one or more of a rectifier 2142, a voltage regulator 2144, an NFC transceiver 2146, a microcontroller 2148 or microprocessor, one or more sensors 2150, one or more motors, and/or other electrical components. Such a wireless scheme may enable communication of command and control signals and power between the tool and other parts of a robotic surgical system (e.g., tool driver, robotic arm, control console, etc.).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; many modifications, combinations, and variations are possible in view of the above teachings. The embodiments were chosen and described in order to best explain the principles of the invention and its practical applications, and they thereby enable others skilled in the art to best utilize the invention and various embodiments with various modifications and/or in various combinations as are suited to the particular use contemplated.

The invention claimed is:

1. A tool driver for use in robotic surgery, comprising:

a tool carriage configured to receive a surgical tool, wherein the tool carriage comprises:

at least one motor drive for actuating one or more articulated movements of the surgical tool, the at least one motor drive comprises a linear axis drive having a series of gears comprising a motor drive gear mounted to an output of the motor drive, a ball screw gear mounted to an input of a ball screw and an idler gear that engages with the motor drive gear and the ball screw gear; and a first magnetic sensor configured to detect an angular orientation experienced by the motor drive gear and a second magnetic sensor configured to detect an angular orientation experienced by the ball screw gear to determine a position of the surgical tool or the tool carriage.

2. The tool driver of claim 1 wherein the first magnetic sensor and the second magnetic sensor comprise an absolute multi-turn encoder.

3. The tool driver of claim 1 wherein the idler gear comprises a first idler gear engaged with the motor drive gear and a second idler gear engaged with the ball screw gear, and the first idler gear and the second idler gear have a different number of teeth.

4. The tool driver of claim 1 wherein the first magnetic sensor comprises a magnet and the second magnetic sensor comprises a Hall effect sensor.

5. The tool driver of claim 1 wherein the linear axis drive further comprises a linearly traveling component and a linear position of the linearly traveling component is determined based on a number of teeth of the motor drive gear and the ball screw gear to determine a linear position of the surgical tool or the tool carriage.

6. The tool driver of claim 1 wherein the motor drive gear and the ball screw gear have different gear ratios.

7. The tool driver of claim 1 wherein the first magnetic sensor and the second magnetic sensor are further configured to detect a rotational position of an output of the motor drive to determine a linear position of the surgical tool coupled to the tool carriage.

8. The tool driver of claim 1 wherein the first magnetic sensor and the second magnetic sensor are contained on a printed circuit board mounted near the series of gears such that the first magnetic sensor is aligned with a rotational axis of the motor drive gear and the second magnetic sensor is aligned with a rotational axis of the ball screw gear.

9. The tool driver of claim 1 wherein the motor drive is coupled to an input driving mechanism of the surgical tool and the first magnetic sensor and the second magnetic sensor track a linear position of the surgical tool.

10. The tool driver of claim 1 wherein the motor drive is coupled to an input driving mechanism of the tool carriage and the first magnetic sensor and the second magnetic sensor track a linear position of the tool carriage.

11. A tool driver for use in robotic surgery, comprising:

a tool carriage configured to receive a surgical tool, wherein the tool carriage comprises a plurality of motor drive modules configured to actuate one or more articulated movements of the surgical tool, at least one motor drive module of the plurality of motor drive modules comprises a linear axis drive having a series of gears in a side by side arrangement, the series of gears comprising a motor drive gear mounted to an output of the motor drive module, a ball screw gear mounted to an input of a ball screw and an idler gear between the motor drive gear and the ball screw gear; and a magnetic sensor configured to detect a movement experienced by the motor drive gear and the ball screw gear for determining a position of the surgical tool or the tool carriage.

12. The tool driver of claim 11 wherein the magnetic sensor is an absolute multi-turn encoder.

13. The tool driver of claim 11 wherein the magnetic sensor detects an angular orientation of the motor drive gear and the ball screw gear in the linear axis drive to determine a linear position of the surgical tool coupled to the tool carriage.

14. The tool driver of claim 11 wherein the magnetic sensor comprises a magnet and a Hall effect sensor operable to detect a relative angular orientation of the motor drive gear and the ball screw gear in the linear axis drive.

15. The tool driver of claim 11 wherein the idler gear comprises a split idler gear having a first idler gear and a second idler gear, and the magnetic sensor comprises a first sensor for detecting an angular orientation of the motor drive gear and a second sensor for detecting an angular orientation of the ball screw gear.

16. The tool driver of claim 11 wherein the motor drive gear and the ball screw gear have different gear ratios.

17. The tool driver of claim 11 wherein the magnetic sensor is further configured to detect a rotational position of an output of the motor drive module to determine a linear position of the surgical tool coupled to the tool carriage.

18. The tool driver of claim 11 wherein the magnetic sensor comprises a first sensor and a second sensor contained on a printed circuit board mounted near the series of gears such that the first sensor is aligned with a rotational axis of the motor drive gear and the second sensor is aligned with a rotational axis of the ball screw gear.

19. The tool driver of claim 11 wherein the magnetic sensor determines a position of the surgical tool.

20. The tool driver of claim 11 wherein the magnetic sensor determines a position of the tool carriage.

* * * * *